(12) United States Patent
Newberry

(10) Patent No.: US 11,675,434 B2
(45) Date of Patent: *Jun. 13, 2023

(54) SYSTEM AND METHOD FOR MOTION DETECTION USING A PPG SENSOR

(71) Applicant: Trilinear BioVentures, LLC, Huntsville, AL (US)

(72) Inventor: Robert Newberry, New Hope, AL (US)

(73) Assignee: TRILINEAR BIOVENTURES, LLC, Huntsville, AL (US)

(*) Notice: Subject to any disclaimer, the term of this patent is extended or adjusted under 35 U.S.C. 154(b) by 0 days.

This patent is subject to a terminal disclaimer.

(21) Appl. No.: 16/570,612

(22) Filed: Sep. 13, 2019

(65) Prior Publication Data

US 2020/0004336 A1    Jan. 2, 2020

Related U.S. Application Data

(63) Continuation of application No. 16/103,876, filed on Aug. 14, 2018, now Pat. No. 10,466,783.

(60) Provisional application No. 62/675,151, filed on May 22, 2018, provisional application No. 62/643,643, filed on Mar. 15, 2018.

(51) Int. Cl.
*G06F 3/01* (2006.01)
*G06F 3/03* (2006.01)
*A61B 5/00* (2006.01)
*A61B 5/389* (2021.01)
(Continued)

(52) U.S. Cl.
CPC ............ *G06F 3/014* (2013.01); *A61B 5/0075* (2013.01); *A61B 5/389* (2021.01); *A61B 5/6825* (2013.01); *A61B 5/725* (2013.01); *A61B 5/7475* (2013.01); *G06F 3/015* (2013.01); *G06F 3/017* (2013.01);
(Continued)

(58) Field of Classification Search
CPC ...................................................... G06F 3/014
See application file for complete search history.

(56) References Cited

U.S. PATENT DOCUMENTS 4,913,150 A    4/1990   Cheung et al.
5,115,133 A    5/1992   Knudson
(Continued)

FOREIGN PATENT DOCUMENTS

CN   102609627 A   7/2012
CN   103777752 A   5/2014
(Continued)

OTHER PUBLICATIONS

PCT/US2019/015298, International Search Report and Written Opinion (dated Apr. 23, 2019).
(Continued)

*Primary Examiner* — William Boddie
*Assistant Examiner* — Andrew B Schnirel
(74) *Attorney, Agent, or Firm* — Polsinelli PC

(57) ABSTRACT

A photoplethysmography (PPG) circuit obtains PPG signals at one or more wavelengths. The PPG signal is processed to identify motion artifacts. The motion artifacts are correlated with predetermined PPG signal patterns associated with movement of a body part or a control command for a user device. The PPG signals may thus be used to detect movement of the body part or determine a control command. A user device may be controlled in response to the determined control command.

19 Claims, 41 Drawing Sheets

(51) Int. Cl.
*G06V 40/20* (2022.01)
*G06F 1/16* (2006.01)

(52) U.S. Cl.
CPC ............ *G06F 3/0304* (2013.01); *G06V 40/28* (2022.01); *G06F 1/163* (2013.01)

(56) References Cited

U.S. PATENT DOCUMENTS

| | | | |
|---|---|---|---|
| 5,269,310 A | 12/1993 | Jones et al. | |
| 5,358,703 A | 10/1994 | Lai | |
| 5,515,847 A | 5/1996 | Braig et al. | |
| 5,673,692 A | 10/1997 | Schulze et al. | |
| 5,823,966 A | 10/1998 | Buchert | |
| 5,947,911 A | 9/1999 | Wong et al. | |
| 5,983,121 A | 11/1999 | Tsuchiya | |
| 6,087,087 A | 7/2000 | Yonetani et al. | |
| 6,280,390 B1 | 8/2001 | Akselrod et al. | |
| 6,285,896 B1 | 9/2001 | Tobler et al. | |
| 6,305,804 B1 | 10/2001 | Rice et al. | |
| 6,537,225 B1 | 3/2003 | Mills | |
| 6,694,180 B1 | 2/2004 | Boesen | |
| 6,719,705 B2 | 4/2004 | Mills | |
| 6,819,950 B2 | 11/2004 | Mills | |
| 6,921,367 B2 | 7/2005 | Mills | |
| 6,985,763 B2 | 1/2006 | Boas et al. | |
| 7,154,592 B2 | 12/2006 | Reynolds et al. | |
| 7,167,736 B2 | 1/2007 | Winther | |
| 7,171,251 B2 | 1/2007 | Sarussi et al. | |
| 7,179,228 B2 | 2/2007 | Banet | |
| 7,209,775 B2 | 4/2007 | Bae et al. | |
| 7,291,497 B2 | 11/2007 | Holmes et al. | |
| 7,371,562 B2 | 5/2008 | Cunningham et al. | |
| 7,608,045 B2 | 10/2009 | Mills | |
| 7,647,083 B2 | 1/2010 | Al-Ali et al. | |
| 7,761,127 B2 | 7/2010 | Al-Ali et al. | |
| 7,763,472 B2 | 7/2010 | Doctor et al. | |
| 7,764,982 B2 | 7/2010 | Dalke et al. | |
| 7,941,199 B2 | 5/2011 | Kiani | |
| 8,224,411 B2 | 7/2012 | Al-Ali et al. | |
| 8,255,027 B2 | 8/2012 | Al-Ali et al. | |
| 8,328,420 B2 | 12/2012 | Abreu | |
| 8,385,996 B2 | 2/2013 | Smith et al. | |
| 8,401,605 B2 | 3/2013 | Huiku | |
| 8,483,787 B2 | 7/2013 | Al-Ali et al. | |
| 8,494,507 B1 | 7/2013 | Tedesco et al. | |
| 8,597,274 B2 | 12/2013 | Sloan et al. | |
| 8,652,040 B2 | 2/2014 | Leboeuf et al. | |
| 8,676,284 B2 | 3/2014 | He | |
| 8,730,047 B2 | 5/2014 | Ridder et al. | |
| 8,868,149 B2 | 10/2014 | Eisen et al. | |
| 8,888,701 B2 | 11/2014 | Leboeuf et al. | |
| 8,906,693 B2 | 12/2014 | Schultz et al. | |
| 8,923,918 B2 | 12/2014 | Kreger et al. | |
| 8,961,932 B2 | 2/2015 | Silverman | |
| 9,022,973 B2 | 5/2015 | Sexton et al. | |
| 9,131,882 B2 | 9/2015 | Al-Ali et al. | |
| 9,149,216 B1 | 10/2015 | Eisen et al. | |
| 9,149,646 B2 | 10/2015 | Keswarpu et al. | |
| 9,387,033 B2 | 7/2016 | Yodfat et al. | |
| 9,442,092 B2 | 9/2016 | Lane | |
| 9,521,970 B2 | 12/2016 | Hoppe et al. | |
| 9,554,738 B1 | 1/2017 | Gulati et al. | |
| 9,642,578 B2 | 5/2017 | Newberry | |
| 9,668,701 B2 | 6/2017 | Maarek | |
| 9,713,428 B2 | 7/2017 | Chon et al. | |
| 9,739,663 B2 | 8/2017 | Halder et al. | |
| 9,820,656 B2 | 11/2017 | Olivier | |
| 9,839,381 B1 | 12/2017 | Weber et al. | |
| 9,924,895 B2 | 3/2018 | Rawicz et al. | |
| 9,939,899 B2 | 4/2018 | Allec et al. | |
| 9,949,675 B2 | 4/2018 | Miller | |
| 9,999,355 B2 | 6/2018 | Kirenko | |
| 10,028,682 B2 | 7/2018 | Thiele | |
| D824,937 S | 8/2018 | Sparandara et al. | |
| 10,099,554 B2 | 10/2018 | Steeg et al. | |
| 10,130,285 B1 | 11/2018 | Singamsetty et al. | |
| 10,153,796 B2 | 12/2018 | Fung et al. | |
| 10,181,021 B2 | 1/2019 | Venkatraman et al. | |
| 10,206,619 B1 | 2/2019 | Lee et al. | |
| 10,215,698 B2 | 2/2019 | Han et al. | |
| 10,227,063 B2 | 3/2019 | Abreu | |
| 10,232,156 B2 | 3/2019 | Netzel et al. | |
| 10,278,591 B2 | 5/2019 | Gil | |
| D850,316 S | 6/2019 | Ennis et al. | |
| 10,314,500 B2 | 6/2019 | Olivier | |
| 10,322,728 B1 | 6/2019 | Porikli et al. | |
| 10,342,495 B2 | 7/2019 | Melkoniemi et al. | |
| 10,349,847 B2 | 7/2019 | Kwon et al. | |
| 10,420,470 B2 | 9/2019 | Kwon et al. | |
| 10,420,491 B2 | 9/2019 | Rajan et al. | |
| 10,433,726 B2 | 10/2019 | Ramesh et al. | |
| 10,433,738 B2 | 10/2019 | Thomas et al. | |
| 10,433,739 B2 | 10/2019 | Weekly et al. | |
| 10,463,283 B2 | 11/2019 | Ferber et al. | |
| 2002/0049389 A1 | 4/2002 | Abreu | |
| 2003/0036685 A1 | 2/2003 | Goodman | |
| 2003/0166996 A1 | 9/2003 | Kim et al. | |
| 2003/0212336 A1 | 11/2003 | Lee et al. | |
| 2003/0229276 A1 | 12/2003 | Sarussi et al. | |
| 2004/0078219 A1 | 4/2004 | Kaylor et al. | |
| 2004/0100376 A1 | 5/2004 | Lye et al. | |
| 2004/0157341 A1 | 8/2004 | Reynolds et al. | |
| 2004/0225207 A1* | 11/2004 | Bae | A61B 5/0002 600/340 |
| 2005/0101841 A9 | 5/2005 | Kaylor et al. | |
| 2005/0209516 A1 | 9/2005 | Fraden | |
| 2005/0228244 A1 | 10/2005 | Banet | |
| 2005/0228299 A1 | 10/2005 | Banet | |
| 2005/0245831 A1 | 11/2005 | Banet | |
| 2006/0009698 A1 | 1/2006 | Banet | |
| 2006/0094942 A1 | 5/2006 | Winther | |
| 2006/0287589 A1 | 12/2006 | Wobermin et al. | |
| 2007/0202605 A1 | 8/2007 | Doctor et al. | |
| 2007/0203405 A1 | 8/2007 | Shimomura | |
| 2007/0260132 A1 | 11/2007 | Sterling | |
| 2008/0146890 A1 | 6/2008 | Leboeuf et al. | |
| 2008/0165017 A1 | 7/2008 | Schwartz | |
| 2008/0208019 A1 | 8/2008 | Nitzan | |
| 2008/0241199 A1 | 10/2008 | Silverman | |
| 2009/0043178 A1 | 2/2009 | Belotserkovsky | |
| 2009/0048525 A1 | 2/2009 | Rogers et al. | |
| 2009/0096748 A1 | 4/2009 | Wu | |
| 2009/0156988 A1 | 6/2009 | Ferren et al. | |
| 2009/0174578 A1* | 7/2009 | Taki | G01B 11/03 341/20 |
| 2009/0187167 A1 | 7/2009 | Sexton et al. | |
| 2009/0287120 A1 | 11/2009 | Ferren et al. | |
| 2009/0326353 A1 | 12/2009 | Watson et al. | |
| 2010/0049020 A1 | 2/2010 | Dalke et al. | |
| 2010/0191080 A1 | 7/2010 | Mills | |
| 2010/0274101 A1 | 10/2010 | Lin et al. | |
| 2010/0274144 A1 | 10/2010 | Hu et al. | |
| 2010/0331631 A1 | 12/2010 | Maclaughlin | |
| 2011/0082355 A1 | 4/2011 | Eisen et al. | |
| 2011/0106050 A1 | 5/2011 | Yodfat et al. | |
| 2011/0137141 A1 | 6/2011 | Razoumov et al. | |
| 2011/0160697 A1 | 6/2011 | Yodfat et al. | |
| 2011/0166553 A1 | 7/2011 | Holmes et al. | |
| 2011/0224518 A1 | 9/2011 | Tindi et al. | |
| 2011/0237464 A1 | 9/2011 | Cunningham et al. | |
| 2011/0275978 A1 | 11/2011 | Hyde et al. | |
| 2012/0010683 A1 | 1/2012 | Keswarpu et al. | |
| 2012/0029363 A1 | 2/2012 | Lund | |
| 2012/0095302 A1 | 4/2012 | Adhikari | |
| 2012/0131507 A1 | 5/2012 | Sparandara et al. | |
| 2012/0136054 A1 | 5/2012 | Schultz et al. | |
| 2012/0156933 A1 | 6/2012 | Kreger et al. | |
| 2012/0203077 A1 | 8/2012 | He et al. | |
| 2012/0238844 A1 | 9/2012 | Grata et al. | |
| 2012/0330126 A1 | 12/2012 | Hoppe et al. | |
| 2013/0030259 A1 | 1/2013 | Thomsen et al. | |
| 2013/0060098 A1 | 3/2013 | Thomsen et al. | |
| 2013/0066174 A1 | 3/2013 | Addison et al. | |
| 2013/0066176 A1 | 3/2013 | Addison et al. | |

(56) References Cited

U.S. PATENT DOCUMENTS

| | | | |
|---|---|---|---|
| 2013/0110311 A1 | 5/2013 | Ver Steeg et al. | |
| 2013/0310669 A1 | 11/2013 | Nitzan | |
| 2014/0046160 A1 | 2/2014 | Terashima et al. | |
| 2014/0058272 A1* | 2/2014 | Naing | A61B 5/7207 600/479 |
| 2014/0100432 A1 | 4/2014 | Golda et al. | |
| 2014/0112940 A1 | 4/2014 | Lane | |
| 2014/0142403 A1 | 5/2014 | Brumback et al. | |
| 2014/0194342 A1 | 7/2014 | Zhang et al. | |
| 2014/0228649 A1 | 8/2014 | Rayner et al. | |
| 2014/0243648 A1 | 8/2014 | Dubielczyk | |
| 2014/0253709 A1 | 9/2014 | Bresch et al. | |
| 2014/0275852 A1 | 9/2014 | Hong et al. | |
| 2014/0276098 A1 | 9/2014 | Bresch et al. | |
| 2014/0297313 A1 | 10/2014 | Condurso et al. | |
| 2014/0316226 A1 | 10/2014 | Ferber et al. | |
| 2015/0066238 A1 | 3/2015 | Todd et al. | |
| 2015/0088007 A1 | 3/2015 | Bardy et al. | |
| 2015/0094914 A1 | 4/2015 | Abreu | |
| 2015/0105638 A1 | 4/2015 | Eisen et al. | |
| 2015/0109617 A1 | 4/2015 | Gilbert et al. | |
| 2015/0148622 A1 | 5/2015 | Moyer et al. | |
| 2015/0148635 A1 | 5/2015 | Benaron | |
| 2015/0150453 A1 | 6/2015 | Abreu | |
| 2015/0182172 A1 | 7/2015 | Shelley et al. | |
| 2015/0215443 A1 | 7/2015 | Heo et al. | |
| 2015/0229341 A1 | 8/2015 | Fung et al. | |
| 2015/0250404 A1 | 9/2015 | Maarek | |
| 2015/0282747 A1 | 10/2015 | Thiele | |
| 2015/0327784 A1 | 11/2015 | Lading et al. | |
| 2015/0366471 A1 | 12/2015 | Leboeuf et al. | |
| 2015/0366504 A1 | 12/2015 | Connor | |
| 2015/0370320 A1* | 12/2015 | Connor | A61B 5/1126 345/173 |
| 2016/0018257 A1 | 1/2016 | Mirov et al. | |
| 2016/0058308 A1 | 3/2016 | Robinson | |
| 2016/0058312 A1 | 3/2016 | Han et al. | |
| 2016/0058347 A1 | 3/2016 | Reichgott et al. | |
| 2016/0065840 A1 | 3/2016 | Kim et al. | |
| 2016/0066863 A1 | 3/2016 | Thaveeprungsrporn et al. | |
| 2016/0084869 A1 | 3/2016 | Yuen et al. | |
| 2016/0091980 A1 | 3/2016 | Baranski et al. | |
| 2016/0100781 A1 | 4/2016 | Bechtel et al. | |
| 2016/0120482 A1 | 5/2016 | Kirenko et al. | |
| 2016/0142407 A1 | 5/2016 | Chun et al. | |
| 2016/0206247 A1 | 7/2016 | Morland et al. | |
| 2016/0249820 A1 | 9/2016 | Puig et al. | |
| 2016/0259407 A1 | 9/2016 | Schick | |
| 2016/0262707 A1 | 9/2016 | Devries | |
| 2016/0317096 A1 | 11/2016 | Adams et al. | |
| 2016/0367154 A1 | 12/2016 | Gladshtein et al. | |
| 2016/0374575 A1 | 12/2016 | Kim et al. | |
| 2017/0014035 A1* | 1/2017 | Newberry | A61B 5/02416 |
| 2017/0014041 A1 | 1/2017 | Stut et al. | |
| 2017/0027521 A1 | 2/2017 | Geva et al. | |
| 2017/0031453 A1 | 2/2017 | Presura | |
| 2017/0039045 A1 | 2/2017 | Abrahami et al. | |
| 2017/0050518 A1 | 2/2017 | Steeg et al. | |
| 2017/0071550 A1 | 3/2017 | Newberry | |
| 2017/0090567 A1 | 3/2017 | Allec et al. | |
| 2017/0091436 A1 | 3/2017 | Cao et al. | |
| 2017/0161577 A1 | 6/2017 | Lee et al. | |
| 2017/0172477 A1 | 6/2017 | Adusumilli et al. | |
| 2017/0215811 A1 | 8/2017 | Newberry | |
| 2017/0220752 A1 | 8/2017 | Murphy et al. | |
| 2017/0231490 A1 | 8/2017 | Toth et al. | |
| 2017/0256110 A1 | 9/2017 | Divincent et al. | |
| 2017/0311825 A1 | 11/2017 | Weekly et al. | |
| 2017/0347894 A1 | 12/2017 | Bhushan et al. | |
| 2017/0347899 A1 | 12/2017 | Bhushan et al. | |
| 2018/0117291 A1 | 5/2018 | Netzel et al. | |
| 2018/0140210 A1 | 5/2018 | Jelfs et al. | |
| 2018/0140237 A1 | 5/2018 | Rajan et al. | |
| 2018/0177416 A1 | 6/2018 | Church et al. | |
| 2018/0177440 A1 | 6/2018 | Jelfs et al. | |
| 2018/0200433 A1 | 7/2018 | Cirit | |
| 2018/0264242 A1 | 9/2018 | Hoffman et al. | |
| 2018/0353137 A1 | 12/2018 | Balajadia et al. | |
| 2018/0358119 A1 | 12/2018 | Bhushan et al. | |
| 2019/0046039 A1 | 2/2019 | Ramesh et al. | |
| 2019/0050622 A1 | 2/2019 | Cabibihan et al. | |
| 2019/0086331 A1 | 3/2019 | Han | |
| 2019/0099114 A1 | 4/2019 | Radian et al. | |
| 2019/0110745 A1 | 4/2019 | Linnes et al. | |
| 2019/0125963 A1 | 5/2019 | Mou et al. | |
| 2019/0125964 A1 | 5/2019 | Mou et al. | |
| 2019/0133471 A1 | 5/2019 | Olson et al. | |
| 2019/0192085 A1 | 6/2019 | Krishna et al. | |
| 2019/0192086 A1 | 6/2019 | Krishna et al. | |
| 2019/0251238 A1 | 8/2019 | Venkatraman et al. | |
| 2019/0286233 A1* | 9/2019 | Newberry | G06F 3/015 |
| 2019/0349367 A1* | 11/2019 | Chang | H04W 4/02 |
| 2019/0358387 A1 | 11/2019 | Elbadry et al. | |

FOREIGN PATENT DOCUMENTS

| | | | |
|---|---|---|---|
| CN | 105433931 A | 3/2016 | |
| EP | 3488776 A1 | 5/2019 | |
| WO | 2004047630 A1 | 6/2004 | |
| WO | 2007013054 A1 | 2/2007 | |
| WO | 2008006150 A1 | 1/2008 | |
| WO | 2010128852 A3 | 11/2010 | |
| WO | 2010147968 A1 | 12/2010 | |
| WO | 2012108895 A1 | 8/2012 | |
| WO | 2013052318 A1 | 4/2013 | |
| WO | 2013127564 A1 | 9/2013 | |
| WO | 2014163583 A1 | 10/2014 | |
| WO | 2015143197 A1 | 9/2015 | |
| WO | 2015200148 A1 | 12/2015 | |
| WO | WO 2017/001250 | * 6/2016 | A61B 5/024 |
| WO | 2017001249 A1 | 1/2017 | |
| WO | 2018206875 A1 | 11/2018 | |
| WO | 2019030700 A1 | 2/2019 | |
| WO | 2019118053 A1 | 6/2019 | |

OTHER PUBLICATIONS

PCT/US2019/015298, International Preliminary Reporton Patentability (dated Mar. 4, 2020).

* cited by examiner

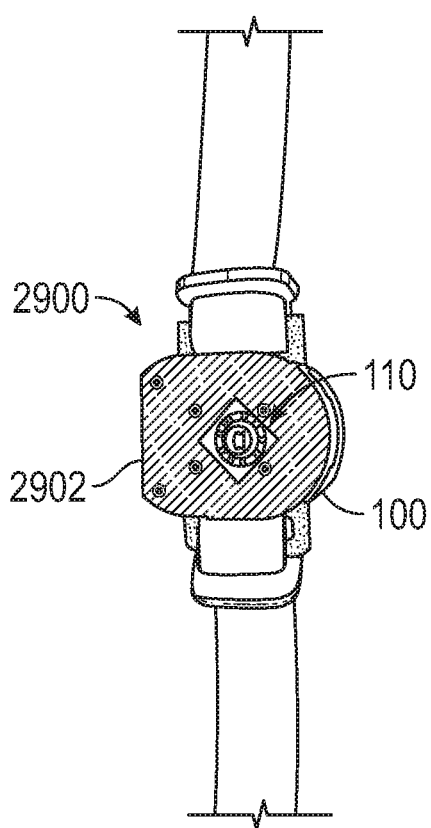 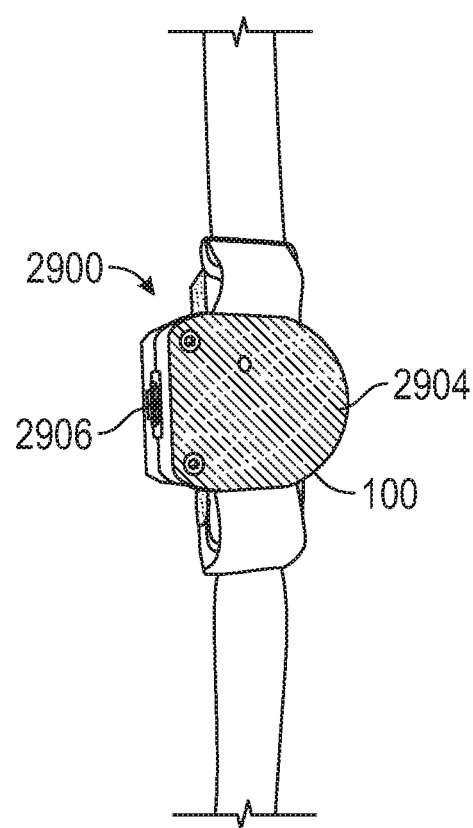
FIG. 29A　　　　　FIG. 29B
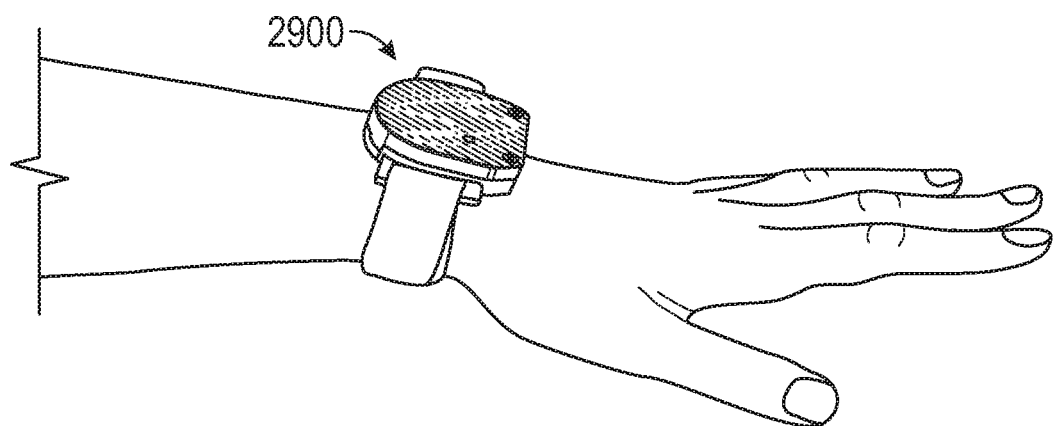
FIG. 29C

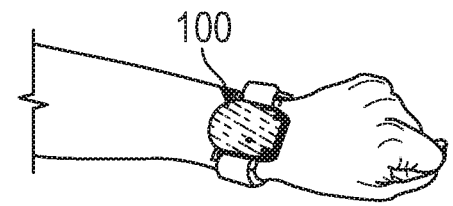
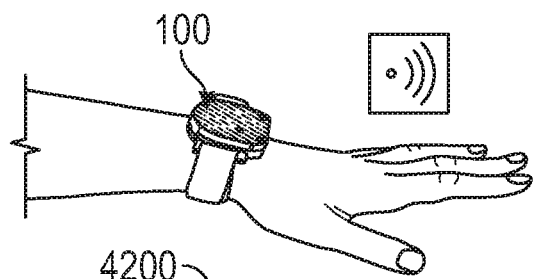
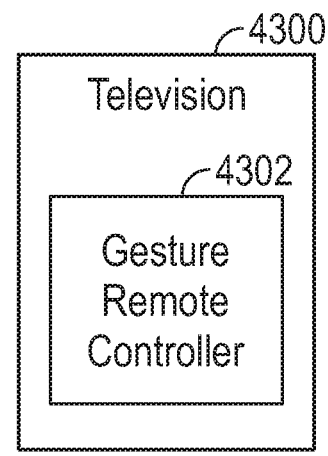
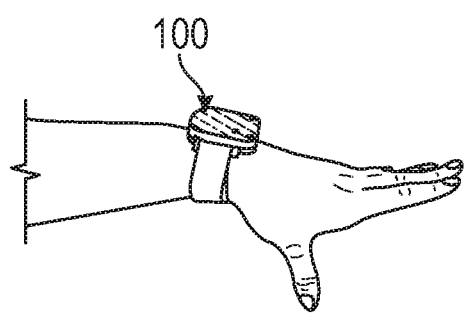
FIG. 43

SYSTEM AND METHOD FOR MOTION DETECTION USING A PPG SENSOR

CROSS REFERENCE TO RELATED APPLICATIONS

The present application is a continuation of U.S. patent application Ser. No. 16/103,876 entitled "SYSTEM AND METHOD FOR MOTION DETECTION USING A PPG SENSOR" filed Aug. 14, 2018, which claims priority under 35 U.S.C. § 119 to U.S. Provisional Application No. 62/675,151 entitled, "SYSTEM AND METHOD OF A BIOSENSOR FOR DETECTION OF VASODILATION," filed May 22, 2018 and to U.S. Provisional Application No. 62/643,643 entitled, "SYSTEM AND METHOD FOR MOVEMENT DETECTION USING A PPG SENSOR," filed Mar. 15, 2018 which are hereby incorporated by reference herein in their entirety.

FIELD

This application relates to a system and method of non-invasive detection of neural stimulation or movement, and in particular to a system and method for monitoring neural stimulation or movement using photoplethysmography (PPG) methods.

BACKGROUND

Photoplethysmography (PPG) involves obtaining a volumetric measurement of tissue and/or vessels in response to blood flow. One current non-invasive method is known for measuring the oxygen saturation of blood using pulse oximeters. With each cardiac cycle the heart pumps blood through vessels creating a pressure pulse. This pressure pulse distends the arteries and arterioles in the subcutaneous tissue. When the heart pumps blood to the body and the lungs during systole, the amount of blood that reaches the capillaries in the skin surface increases, resulting in more light absorption. The blood then travels back to the heart through the venous network, leading to a decrease of blood volume in the capillaries and less light absorption. The pressure pulse may also be detected in veins, e.g., from the venous plexus. In PPG, a light source is directed at skin tissue and reflected light is detected by a photodetector to generate a PPG signal. The change in blood volume during a pressure pulse affects the amount of light reflected to a photodetector. As such, the pressure pulse appears as a peak in the PPG signal. The measured PPG waveform therefore comprises a pulsatile (often called "AC") physiological waveform that reflects cardiac synchronous changes in the blood volume with each heartbeat, which is superimposed on a much larger slowly varying quasi-static ("DC") baseline.

Heretofore, photoplethysmography was used primarily in pulse oximeters to detect a heart rate and oxygen saturation levels. In pulse oximetry, the subject's skin at a 'measurement location' is illuminated with two distinct wavelengths of light and the relative absorbance at each of the wavelengths is determined. For example, a wavelength in the visible red spectrum (for example, at 660 nm) has an extinction coefficient of hemoglobin that exceeds the extinction coefficient of oxihemoglobin. At a wavelength in the near infrared spectrum (for example, at 940 nm), the extinction coefficient of oxihemoglobin exceeds the extinction coefficient of hemoglobin. The pulse oximeter filters the absorbance of the pulsatile fraction of the blood, i.e. that due to arterial blood (AC components), from the constant absorbance by nonpulsatile venous or capillary blood and other tissue pigments (DC components), to eliminate the effect of tissue absorbance to measure the oxygen saturation of arterial blood. PPG techniques have also been described for measuring other blood constituents, such as in U.S. Pat. No. 9,642,578, entitled, "System and Method for Health Monitoring using a Non-Invasive, Multiband Biosensor," issued on May 9, 2017, and incorporated by reference herein in its entirety. In general, when detecting such blood constituents, motion artifacts in the PPG signals are ignored or filtered from the signals.

In one or more embodiments described herein, the PPG signal is used to non-invasively detect movement and/or neural stimulation of a body part of a user.

SUMMARY

According to a first aspect, a biosensor includes a memory configured to store a database including a plurality of predetermined patterns and associated device control commands. The biosensor further includes a sensor configured for positioning over an area of tissue of a user and configured to obtain an optical signal, wherein the optical signal includes a spectral response around a first wavelength of light reflected from the area of the tissue of the user. A processing device is configured to process the optical signal at the first wavelength to identify a first motion artifact at a first time interval and correlate the first motion artifact to a first predetermined pattern of the plurality of predetermined patterns in the database and determine a first device control command associated with the first predetermined pattern using the database. The processing device may further process the optical signal at the first wavelength to identify a second motion artifact at a second time interval and correlate the second motion artifact to a second predetermined pattern of the plurality of predetermined patterns in the database and determine a second device control command associated with the second predetermined pattern using the database.

According to second aspect, a wearable device includes a sensor configured for positioning over an area of tissue of a user and configured to obtain an optical signal, wherein the optical signal includes a spectral response around a first wavelength of light reflected from the area of the tissue of the user. The wearable device further includes a processing circuit in communication with the sensor and configured to determine a heart rate signal from the optical signal; determine a quality factor of the heart rate signal; and when the quality factor exceeds a predetermined threshold, identify a first motion artifact at a first time interval in the optical signal and a second motion artifact at a second time interval in the optical signal. The processing circuit is further configured to compare the first and second motion artifacts to a plurality of predetermined patterns in a database, wherein each of the plurality of predetermined patterns is associated with a control command correlate the first motion artifact to a first predetermined pattern of the plurality of predetermined patterns in the database and determine a first device control command associated with the first predetermined pattern using the database, and correlate the second motion artifact to a second predetermined pattern of the plurality of predetermined patterns in the database and determine a second device control command associated with the second predetermined pattern using the database.

According to a third aspect, a biosensor includes a sensor configured to obtain an optical signal, wherein the optical signal includes a spectral response around a wavelength of light detected from tissue of a user. The biosensor further includes a processing device configured to identify a fluctuation in the optical signal, wherein the fluctuation in the optical signal reflects neural activity or vasodilation of vessels in the tissue of the user and correlate the fluctuation in the optical signal to a predetermined signal pattern, wherein the predetermined signal pattern is associated with an intended movement of a body part due to a mental initiating of movement with little to no actual movement of the body part. The processing device is further configured to determine a control command associated with the intended movement of the body part and control operation of a device in response to the control command.

In one or more of the above aspects, the first and second device control commands are input to a user device or vehicle, and the associated device control commands include at least one of: selection of a key on a virtual keyboard, selection of an icon on a GUI, control movement of a cursor on a display of the user device, or control movement of the vehicle In one or more of the above aspects, the first motion artifact reflects changes in blood flow through vessels in the area of the tissue due to movement of a first body part at the first time interval and wherein the second motion artifact reflects changes in blood flow through vessels in the area of the tissue due to the movement of a second body part at the second time interval.

In one or more of the above aspects, the database further includes motion data of a body part associated with each of the plurality of predetermined patterns. The processing device is further configured to obtain first motion data for the first body part associated with the first predetermined PPG signal pattern and obtain second motion data for a second moving body part associated with the second predetermined PPG signal pattern. The first motion data includes an identification of the first body part, a direction of movement of the first body part and a speed of the movement of the first body part, and the second motion data includes an identification of the second moving body part, a direction of movement of the second body part and a speed of the movement of the second body part.

In one or more of the above aspects, the biosensor may obtain a direct current (DC) level or maximum amplitude of the motion artifact and determine a force of movement of the body part using the DC level or the maximum amplitude level.

In one or more of the above aspects, the sensor is included in a band configured for positioning over the area of the tissue of a wrist or arm of the user and comprises a photodetector configured to detect light from the area of the tissue of the wrist or arm of the user and at least one light source configured to emit light at the first wavelength.

In one or more of the above aspects, the processing device is a neural network processing device and an input vector is generated using the PPG signal.

In one or more of the above aspects, the biosensor further includes a transmitter configured to transmit the first and second device control commands to a user device or vehicle.

In one or more of the above aspects, the processing circuit is further configured to control the wearable device in response to the first and second device control commands.

In one or more of the above aspects, the processing circuit is further configured to initiate a training mode for customization of the first predetermined pattern in a database; request movement of a first body part of the user; obtain an optical signal of the user during the requested movement of the first body part; identify a motion artifact in the optical signal due to the requested movement of the body part; and update the first predetermined pattern in the database using the motion artifact in the optical signal.

In one or more of the above aspects, the processing circuit is further configured to generate a request to reposition the wearable device when the quality factor of the heart rate signal is not within the predetermined threshold.

BRIEF DESCRIPTION OF THE DRAWINGS

FIG. 29A illustrates a perspective view of an embodiment of a bottom portion of a wristband including an integrated biosensor.

FIG. 29B illustrates a perspective view of an embodiment of a top portion of the wristband including the biosensor.

FIG. 29C illustrates a perspective view of an embodiment of the wristband including the biosensor positioned on a wrist of a user.

FIG. 43 illustrates a schematic block diagram of another embodiment of the biosensor configured to control a device using PPG signals.

DETAILED DESCRIPTION

The word "exemplary" or "embodiment" is used herein to mean "serving as an example, instance, or illustration." Any implementation or aspect described herein as "exemplary" or as an "embodiment" is not necessarily to be construed as preferred or advantageous over other aspects of the disclosure. Likewise, the term "aspects" does not require that all aspects of the disclosure include the discussed feature, advantage, or mode of operation.

Embodiments will now be described in detail with reference to the accompanying drawings. In the following description, numerous specific details are set forth in order to provide a thorough understanding of the aspects described herein. It will be apparent, however, to one skilled in the art, that these and other aspects may be practiced without some or all of these specific details. In addition, well known steps in a method of a process may be omitted from flow diagrams presented herein in order not to obscure the aspects of the disclosure. Similarly, well known components in a device may be omitted from figures and descriptions thereof presented herein in order not to obscure the aspects of the disclosure.

Overview

In an embodiment, a biosensor includes an optical or photoplethysmography (PPG) circuit configured to transmit light at one or more wavelengths directed at skin tissue of a user or patient. The user/patient may include any living organism, human or non-human. The PPG circuit detects light reflected from the skin tissue of the user or transmitted through the skin tissue and generates one or more spectral responses at one or more wavelengths. A processing circuit integrated in the biosensor or in communication with the biosensor processes the spectral data to obtain a user's vitals, concentrations of substances in blood flow and/or other health information. Alternatively, or in addition thereto, the spectral responses at one or more wavelengths are analyzed to detect motion data. For example, the PPG waveforms may be analyzed to detect a movement of a user, such as a user's hand or a finger, as described in more detail herein. The movement recognition may then be used for providing instructions and control of an input device (such as a keyboard, touchpad or mouse) or can be used for any electronic system needing man-machine interaction.

Embodiment—Biosensor

Figure 1:
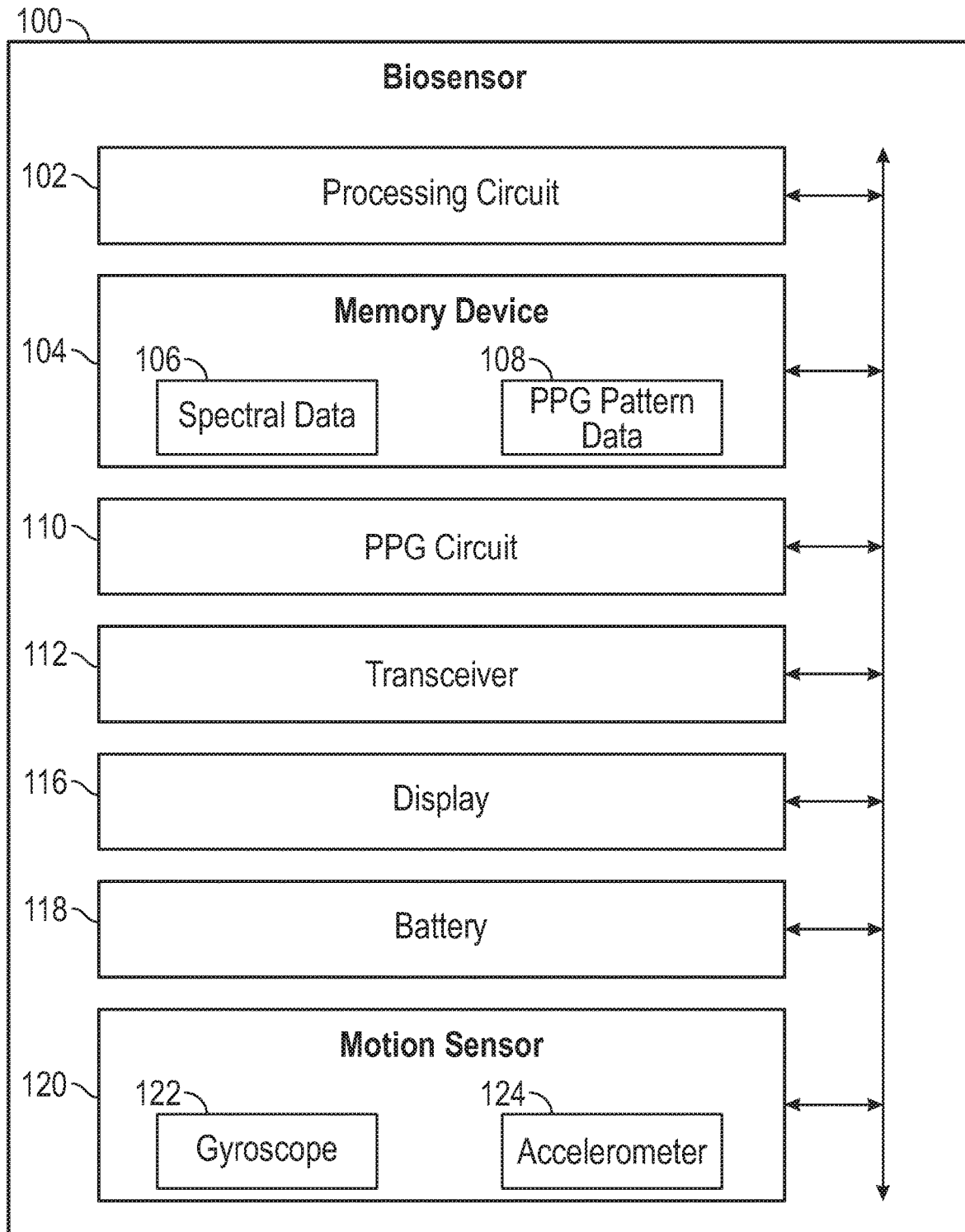
FIG. 1 illustrates a schematic block diagram of exemplary components in an embodiment of the biosensor.

FIG. 1 illustrates a schematic block diagram of exemplary components in an embodiment of the biosensor 100. The biosensor 100 may include one or more processing circuits 102 communicatively coupled to a memory device 104. In one aspect, the memory device 104 may include one or more non-transitory processor readable memories that store instructions which when executed by the one or more processing circuits 102, causes the one or more processing circuits 102 to perform one or more functions described herein. The processing circuit 102 may be co-located with one or more of the other circuits of the biosensor 100 in a same physical circuit board or located separately in a different circuit board or encasement. The processing circuit 102 may also be communicatively coupled wirelessly or wired to a user device, central control module and/or server. The memory device may store motion patterns 106 and/or PPG data 108 obtained by the biosensor 100.

The biosensor 100 may include a temperature sensor 114 configured to detect a temperature of a user. For example, the temperature sensor 114 may include an array of sensors (e.g., 16×16 pixels) to detect a temperature of skin tissue of a user. The temperature sensor 114 may be used to calibrate the PPG circuit 110. The biosensor 100 may include a display 116 to display biosensor data or a control user interface for the biosensor 100.

The biosensor 100 further includes a transceiver 112. The transceiver 112 may include a wireless or wired transceiver configured to communicate with or with one or more devices over a LAN, MAN and/or WAN. In one aspect, the wireless transceiver may include a Bluetooth enabled (BLE) transceiver or IEEE 802.11ah, Zigbee, IEEE 802.15-11 or WLAN (such as an IEEE 802.11 standard protocol) compliant transceiver. In another aspect, the wireless transceiver may operate using RFID, short range radio frequency, infrared link, or other short range wireless communication protocol. In another aspect, the wireless transceiver may also include or alternatively include an interface for communicating over a cellular network. The transceiver 112 may also include a wired transceiver interface, e.g., a USB port or other type of wired connection, for communication with one or more other devices over a LAN, MAN and/or WAN. The transceiver 112 may include a wireless or wired transceiver configured to communicate with a vehicle or its components over a controller area network (CAN), Local Interconnect Network (LIN), Flex Ray, Media Oriented Systems Transport (MOST), (On-Board Diagnostics II), Ethernet or using another type of network or protocol. The biosensor 100 may transmit using the transceiver 112 over a wide area network, such as a cellular network, to a third party service provider, such as a health care provider or emergency service provider, or to a remote user device. The biosensor 100 may be battery operated and include a battery 118, such as a lithium ion battery.

The biosensor 100 may further include one or more motion sensors 120. For example, motion sensors 120 may include a gyroscope 122 and/or an accelerometer 124 or other motion sensing device. For example, the accelerometer 124 may be a three-axis accelerometer that measures linear acceleration in up to three-dimensions (for example, x-axis, y-axis, and z-axis). The gyroscope 122 may be a three-axis gyroscope that measures rotational data, such as rotational movement and/or angular velocity, in up to three-dimensions (for example, yaw, pitch, and roll). In some embodiments, accelerometer 124 may be a microelectromechanical system (MEMS) accelerometer, and gyroscope 122 may be an MEMS gyroscope. The processing circuit 102 may receive motion sensor data from the gyroscope 122 or accelerometer 124 to track acceleration, rotation, position, or orientation information of the biosensor 100 in six degrees of freedom through three-dimensional space. The motion sensor may thus provide motion data relating to movement of the biosensor in three-dimensional (3D) space in relation to a portion of the user or to a control plane.

In some embodiments, the biosensor 100 may include other types of sensors in addition to the gyroscope 122 or accelerometer 124. For example, the biosensor 100 may include an altimeter or barometer, or other types of location sensors, such as a GPS sensor. The motion sensors 120 are configured to detect movement and direction of movement, e.g. with respect to a reference plane or a portion of the user. The biosensor 100 may be implemented in a watch, in a patch, in a band, in an earpiece, in a helmet, in a headband, necklace, or in other form factors. The biosensor 100 is positioned adjacent to the skin on an arm, wrist, hand, ankle, foot, or other body part.

Embodiment—PPG Circuit

Figure 2:
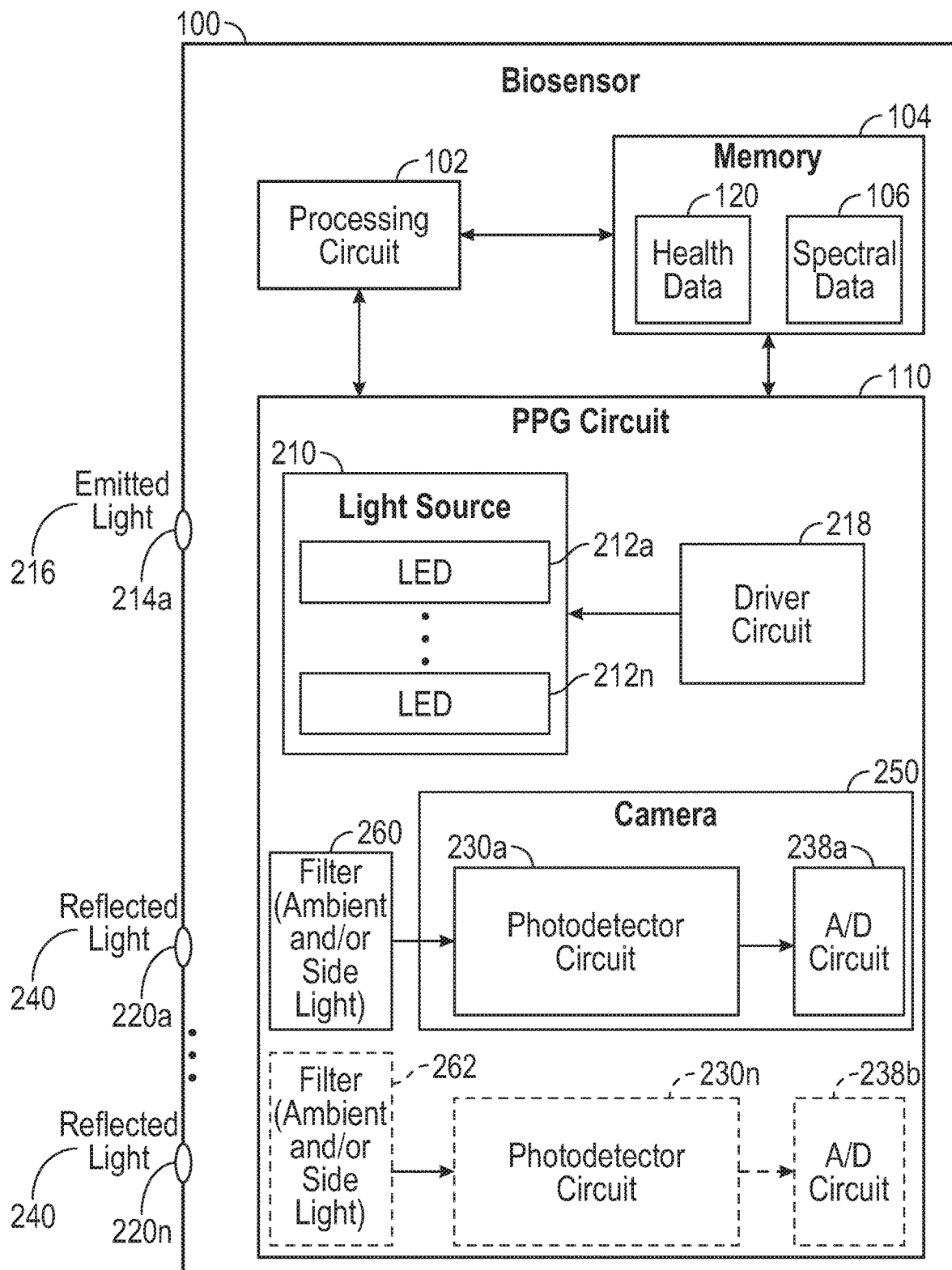
FIG. 2 illustrates a schematic block diagram of an embodiment of the PPG circuit in more detail.

FIG. 2 illustrates a schematic block diagram of an embodiment of the PPG circuit 110 in more detail. The PPG circuit 110 includes a light source 210 configured to emit a plurality of wavelengths of light across various spectrums. The plurality of LEDs 212a-n are configured to emit light in one or more spectrums, including infrared (IR) light, ultraviolet (UV) light, near IR light or visible light, in response to driver circuit 218. For example, the biosensor 100 may include a first LED 212a that emits visible light and a second LED 212b that emits infrared light and a third LED 212c that emits UV light, etc. In another embodiment, one or more of the light sources 212a-n may include tunable LEDs or lasers operable to emit light over one or more frequencies or ranges of frequencies or spectrums in response to driver circuit 218.

In an embodiment, the driver circuit 218 is configured to control the one or more LEDs 212a-n to generate light at one or more frequencies for predetermined periods of time. The driver circuit 218 may control the LEDs 212a-n to operate concurrently or consecutively. The driver circuit 218 is configured to control a power level, emission period and frequency of emission of the LEDs 212a-n. The biosensor 100 is thus configured to emit one or more wavelengths of light in one or more spectrums that is directed at the surface or epidermal layer of the skin tissue of a user. The emitted light 216 passes through at least one aperture 214 directed at the surface or epidermal layer of the skin tissue of a user.

The PPG circuit 110 further includes one or more photodetector circuits 230a-n. The photodetector circuits 230 may be implemented as part of a camera 250. For example, a first photodetector circuit 230 may be configured to detect visible light and the second photodetector circuit 230 may be configured to detect IR light. Alternatively, one or more of the photodetectors 230a-n may be configured to detect light across multiple spectrums. When multiple photodetectors 230 are implemented, the detected signals obtained from each of the photodetectors may be added or averaged. Alternatively, a detected light signal with more optimal signal to noise ration may be selected from the multiple photodetector circuits 230a-n.

The first photodetector circuit 230 and the second photodetector circuit 230 may also include a first filter 260 and a second filter 262 configured to filter ambient light and/or scattered light. For example, in some embodiments, only light reflected at an approximately perpendicular angle to the skin surface of the user is desired to pass through the filters. The first photodetector circuit 230 and the second photodetector circuit 230n are coupled to a first A/D circuit 238a and a second A/D circuit 238b. Alternatively, a single A/D circuit 238 may be coupled to each of the photodetector circuits 230a-n.

In another embodiment, a single photodetector circuit 230 may be implemented operable to detect light over multiple spectrums or frequency ranges. The one or more photodetector circuits 230 include one or more types of spectrometers or photodiodes or other type of circuit configured to detect an intensity of light as a function of wavelength to obtain a spectral response. In use, the one or more photodetector circuits 230 detect the intensity of reflected light 240 from skin tissue of a user that enters one or more apertures 220a-n of the biosensor 100. In another example, the one or more photodetector circuits 230 detect the intensity of light due to transmissive absorption (e.g., light transmitted through tissues, such as a fingertip or ear lobe). The one or more photodetector circuits 230a-n then obtain a spectral response of the reflected or transmissive light by measuring an intensity of the light at one or more wavelengths.

In another embodiment, the light source 210 may include a broad spectrum light source, such as a white light to infrared (IR) or near IR LED, that emits light with wavelengths across multiple spectrums, e.g. from 350 nm to 2500 nm. Broad spectrum light sources with different ranges may be implemented. In an aspect, a broad spectrum light source is implemented with a range across 100 nm wavelengths to 2000 nm range of wavelengths in the visible, IR and/or UV frequencies. For example, a broadband tungsten light source for spectroscopy may be used. The spectral response of the reflected light 240 is then measured across the wavelengths in the broad spectrum, e.g. from 350 nm to 2500 nm, concurrently. In an aspect, a charge coupled device (CCD) spectrometer may be configured in the photodetector circuit 230 to measure the spectral response of the detected light over the broad spectrum.

The PPG circuit 110 may also include a digital signal processing (DSP) circuit or filters or amplifiers to process the spectral data. The spectral data may then be processed by the processing circuit 102 to obtain health data of a user. The spectral data may alternatively or in additionally be transmitted by the biosensor 100 to a central control module for processing to obtain health data of a user.

Figure 3:
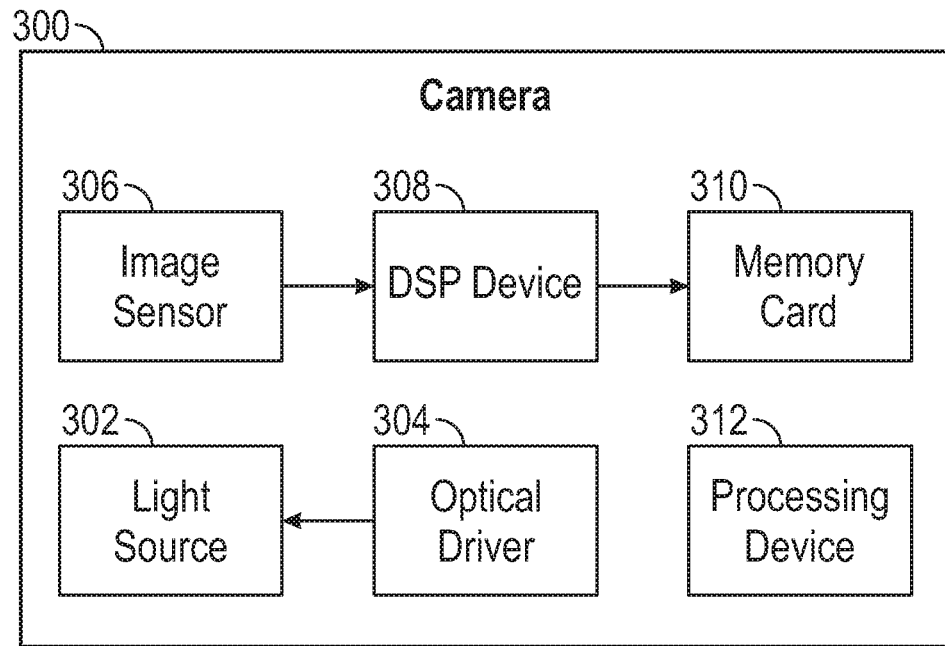
FIG. 3 illustrates a schematic block diagram of another embodiment of a PPG circuit implemented within a camera.

FIG. 3 illustrates a schematic block diagram of another embodiment of a PPG circuit 110 implemented within a camera 300. In an embodiment, the camera includes a light source 302 configured to emit light in one or more of the visible, IR and/or UV spectrum. In one embodiment, an optical driver 304 is configured to control the light source 302. In a health monitoring mode, the optical driver 304 controls the light source to emit light at predetermined wavelengths to detect health data. The health data may include one or more of: heart rate, respiration rate, heart rate variability, vasodilation, etc. The health data may also include concentration levels of substances in blood flow such as $SpO_2$, nitric oxide (NO), liver enzymes such as P450, or other blood substances. The camera 300 further includes an image sensor 306 (such as a photodetector) that is sensitive to UV, visible and/or IR light. A digital signal processing (DSP) device 308 receives the pixel intensity levels for an array of pixels (such as 1024×1068) at each channel (RGB, IR, UV, etc.) for each frame. For example, in a motion detection or a health monitoring mode, the image sensor 306 and DSP device 308 process IR and UV channels as well as RGB channels. The UV and IR light may be filtered when not in a health monitoring mode or motion detection mode. A memory card 1210 stores the image data for each frame. A processing device 312 is configured to process the image data for the frames to determine PPG signals at one or more wavelengths. In another embodiment, the image data may be transmitted to another control module for analysis. The camera 300 may be implemented in a user device, such as a smart phone, laptop, smart tablet, watch, bracelet, button, webcam, video camera in a vehicle, etc.

In an embodiment herein, detection of light in UV range may be implemented in the camera, e.g. from ambient light or a custom LED. Derivation of a PPG signal from light reflected in the UV range from a body part has been found to have advantages over light in the visible and IR range. For example, UV light reflected from a face may be used to derive a PPG signal. The UV light provides an improved PPG signal for detection of heart rate, respiration rate, $SpO_2$ and nitric oxide (NO) levels as well as motion detection.

Embodiment—Motion Detection Using a PPG Signal

In one aspect, the biosensor 100 receives reflected light or transmissive light from skin tissue to obtain a spectral response, e.g. a PPG signal, around a wavelength. The spectral response includes a spectral curve that illustrates an intensity or power or energy at the wavelength in a spectral region of the detected light. Pattern classification and recognition algorithms are used in conjunction with predetermined PPG patterns to obtain motion data, e.g. an identification of a moving body part and type of motion of the body part. For example, a first PPG pattern may correspond to a rotation of a hand while a second PPG pattern may correspond to a vertical movement of an index finger. One or more of the predetermined PPG patterns are recognized in the detected PPG signal. The moving body part and the type of movement (horizontal, vertical, extension, retraction, rotation) are then identified to generate motion data. Control commands may be mapped to the motion data to generate an input to a device.

Figure 4:
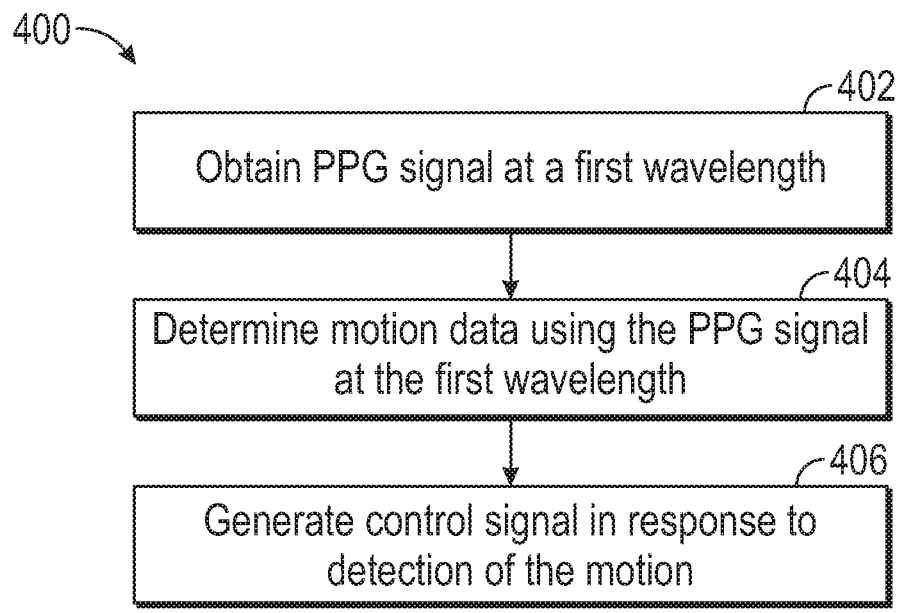
FIG. 4 illustrates a logical flow diagram of an embodiment of a method for motion detection using a PPG signal.

FIG. 4 illustrates a logical flow diagram of an embodiment of a method 400 for motion detection using a PPG signal. The biosensor 100 transmits light around a first wavelength from a light source at a first location. The biosensor 100 detects the light (reflected from the skin or transmitted through the skin) and determines a PPG signal at the first wavelength at 402.

Photoplethysmography (PPG) is used to measure time-dependent volumetric properties of blood in blood vessels due to the cardiac cycle. For example, the heartbeat generates a pressure pulse that affects the volume of blood flow and the vasodilation of vessels. For example, incident light $I_O$ is directed at a tissue site at one or more wavelengths. The reflected/transmitted light I is detected by a photodetector or sensor array in a camera. At a peak of blood flow or volume, the reflected light $I_L$ 414 is at a minimum due to absorption by the pulsating blood, non-pulsating blood, other tissue, etc. At a minimum of blood flow or volume during the cardiac cycle, the Incident or reflected light $I_H$ 416 is at a maximum due to lack of absorption from the pulsating blood volume. Since the light I is reflected or traverses through a different volume of blood at the two measurement times, the measurement provided by a PPG sensor is said to be a 'volumetric measurement' descriptive of the differential volumes of blood present at a certain location within the user's vessels at different times during the cardiac cycle. These principles described herein may be applied to venous blood flow and arterial blood flow.

In addition to the time-dependent volumetric properties of blood in blood vessels due to the cardiac cycle, the PPG signal also reflects movement due to changing optical properties of the underlying tissue and motion artifacts. Even with minimal or no movement, a neural stimulation affects vasodilation of surrounding vessels that may be detected by the PPG signal. Digital signal processing may be performed on the PPG signal, such as amplification, filtering of heart rate or respiration rate, etc. For example, responses in the PPG signals greater than a 10 Hz rate of the typical cardiac cycle may be due to neural activity.

The moving body part and the type of movement (horizontal, vertical, extension, retraction, rotation) are then identified to generate motion data at 404. Pattern classification and recognition algorithms may be used in conjunction with predetermined PPG patterns to obtain the motion data. Alternatively, a neural network or Artificial Intelligence (AI) device may be used to analyze the PPG signal using training vectors to determine the motion data.

Control commands may be mapped to the motion data to generate an input to a device at 406. For example, a corresponding hand gestures or finger movements may be mapped into various control commands to achieve a conventional input similar to a mouse, a keyboard, a touch screen, etc. The control commands may be used as inputs to any type of electronic device, such as a smart watch, phone, glasses, earbuds, tablet, laptop, television, IoT device, manned or unmanned vehicle, a medical device, such as an artificial limb or wheelchair, etc.

FIG. 5-11 are provided herein to show an example of the PPG signals during no movement and movement of various body parts. The examples illustrate the replicative PPG patterns due to a movement.

Figure 5:
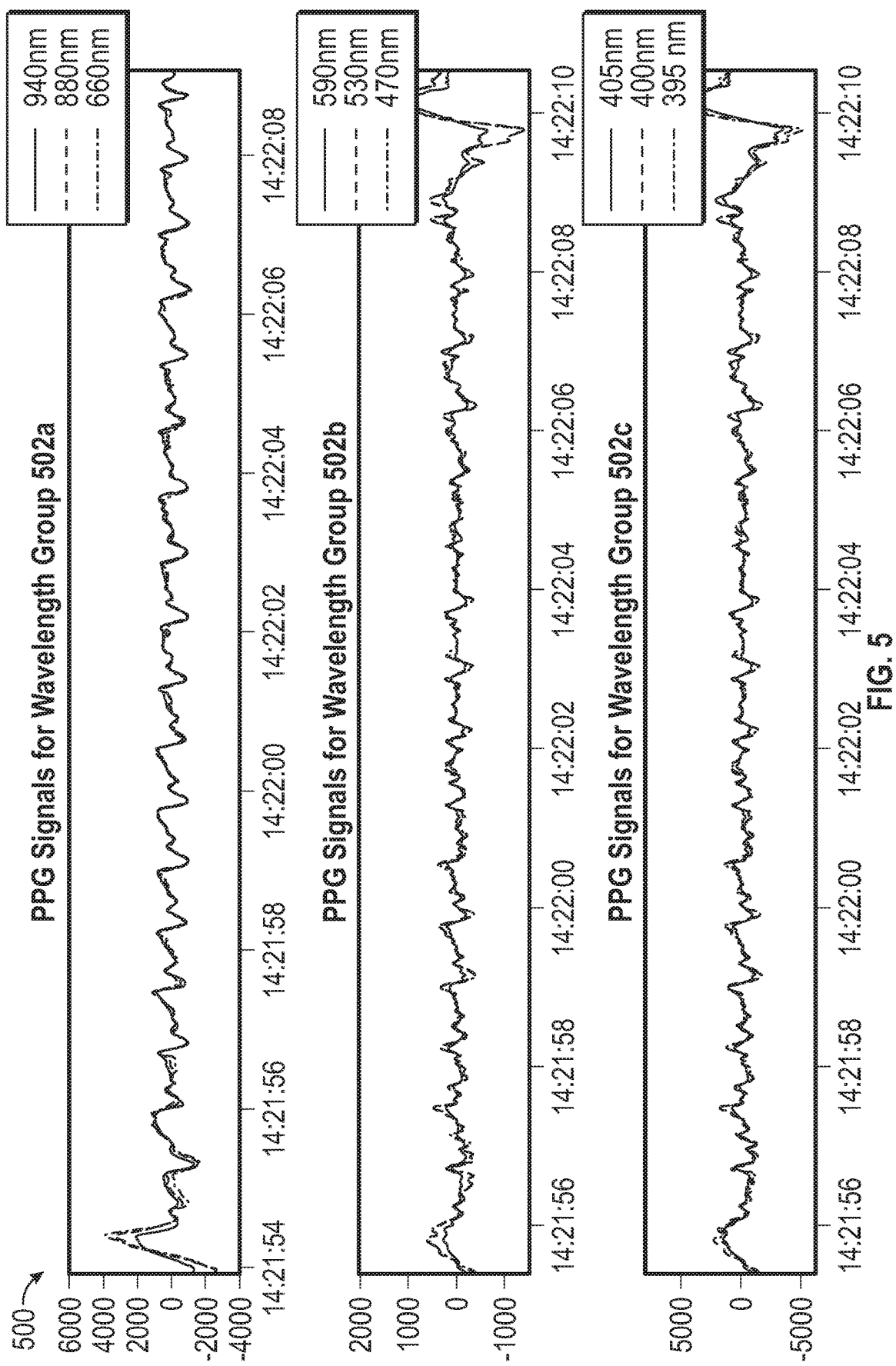
FIG. 5 illustrates a schematic diagram of a graph of spectral responses obtained using an embodiment of the biosensor during a period of little to no motion.

FIG. 5 illustrates a schematic diagram of a graph 500 of spectral responses obtained using an embodiment of the biosensor 100 during a period of little to no motion. In this embodiment, the biosensor 100 is positioned on a wrist of a right hand of a user, as shown in further detail with respect to FIG. 29. In one aspect, the biosensor 100 is configured to emit or pulse light at a plurality of wavelengths during a measurement period. The light at each wavelength (or range of wavelengths) may be emitted concurrently or sequentially. The intensity of the reflected light at each of the wavelengths (or range of wavelengths) is detected, and a graph 500 of the spectral responses is shown over the measurement period. In this example, the PPG signals at the plurality of wavelengths were obtained concurrently during a period of little to no motion of the wrist, hand and fingers.

In this example, the biosensor 100 obtained a PPG signal around a wavelength at 940 nm, a wavelength at 880 nm and a wavelength at 660 nm 412 as shown in the PPG Signals for Wavelength Group 502a. The biosensor 100 also obtained the spectral response for a wavelength at 590 nm, a wavelength at 530 nm and a wavelength at 470 nm as shown in the PPG Signals for Wavelength Group 502b. The biosensor 100 further obtained the spectral response for a wavelength at 405 nm, a wavelength at 400 nm and a wavelength at 395 nm as shown in the PPG Signals for Wavelength Group 502c.

The PPG signals at the plurality of wavelengths include a response to the pressure pulse wave through the vessels from the cardiac cycle. There is little to no indication of movement of the hand or fingers in the PPG signals.

Figure 6:
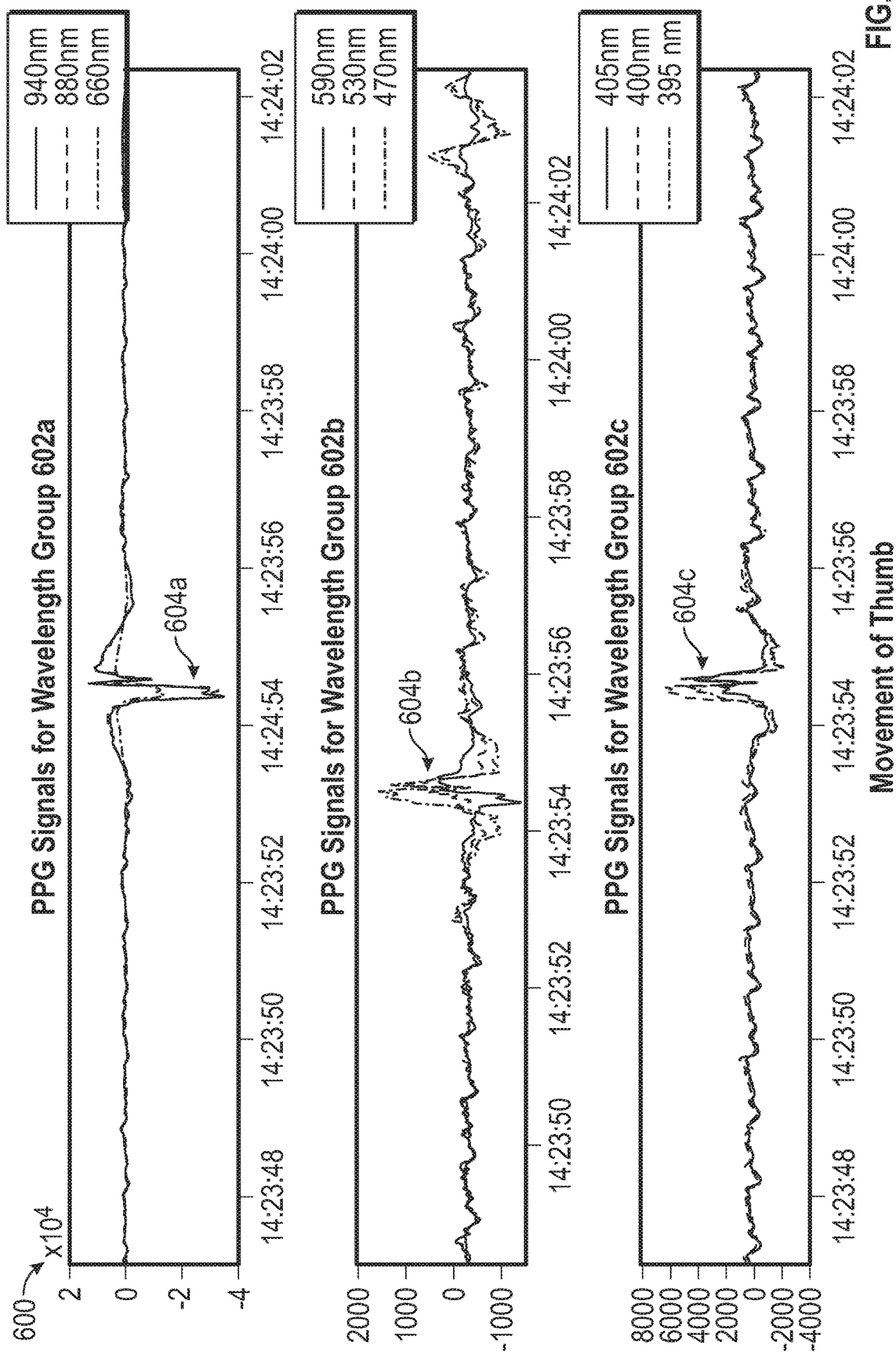
FIG. 6 illustrates a schematic diagram of a graph of spectral responses obtained using an embodiment of the biosensor during movement of a thumb on a right hand of the user.

FIG. 6 illustrates a schematic diagram of a graph 600 of spectral responses obtained using an embodiment of the biosensor 100 during movement of a thumb on a right hand of the user. The biosensor 100 is still positioned on the wrist of the right hand of the user and has not been repositioned. During this measurement period, the thumb on the right hand is moved.

Again, in this example, the biosensor 100 obtained a PPG signal around a wavelength at 940 nm, a wavelength at 880 nm and a wavelength at 660 nm 412 as shown in the PPG Signals for Wavelength Group 602a. The biosensor 100 also obtained the spectral response for a wavelength at 590 nm, a wavelength at 530 nm and a wavelength at 470 nm as shown in the PPG Signals for Wavelength Group 602b. The biosensor 100 further obtained the spectral response for a wavelength at 405 nm, a wavelength at 400 nm and a wavelength at 395 nm as shown in the PPG Signals for Wavelength Group 602c.

The PPG signals at the plurality of wavelengths include a response to the pressure pulse wave through the vessels from the cardiac cycle. In addition, at approximately the time of 14.23.54 seconds, there is an indication of movement of the thumb in the PPG signals as shown in responses 604a-c. The PPG signals at each wavelength have a similar pattern in response to the movement of the thumb, though the pattern 604a in the wavelength group 602a is inverted in this graph. For example, the pattern of the response 604a is similar to the pattern of the response 604b and the pattern of the response at 604c. These patterns 604a-c in the PPG signal are not present in the PPG signals with little to no movement shown in FIG. 5.

Figure 7:
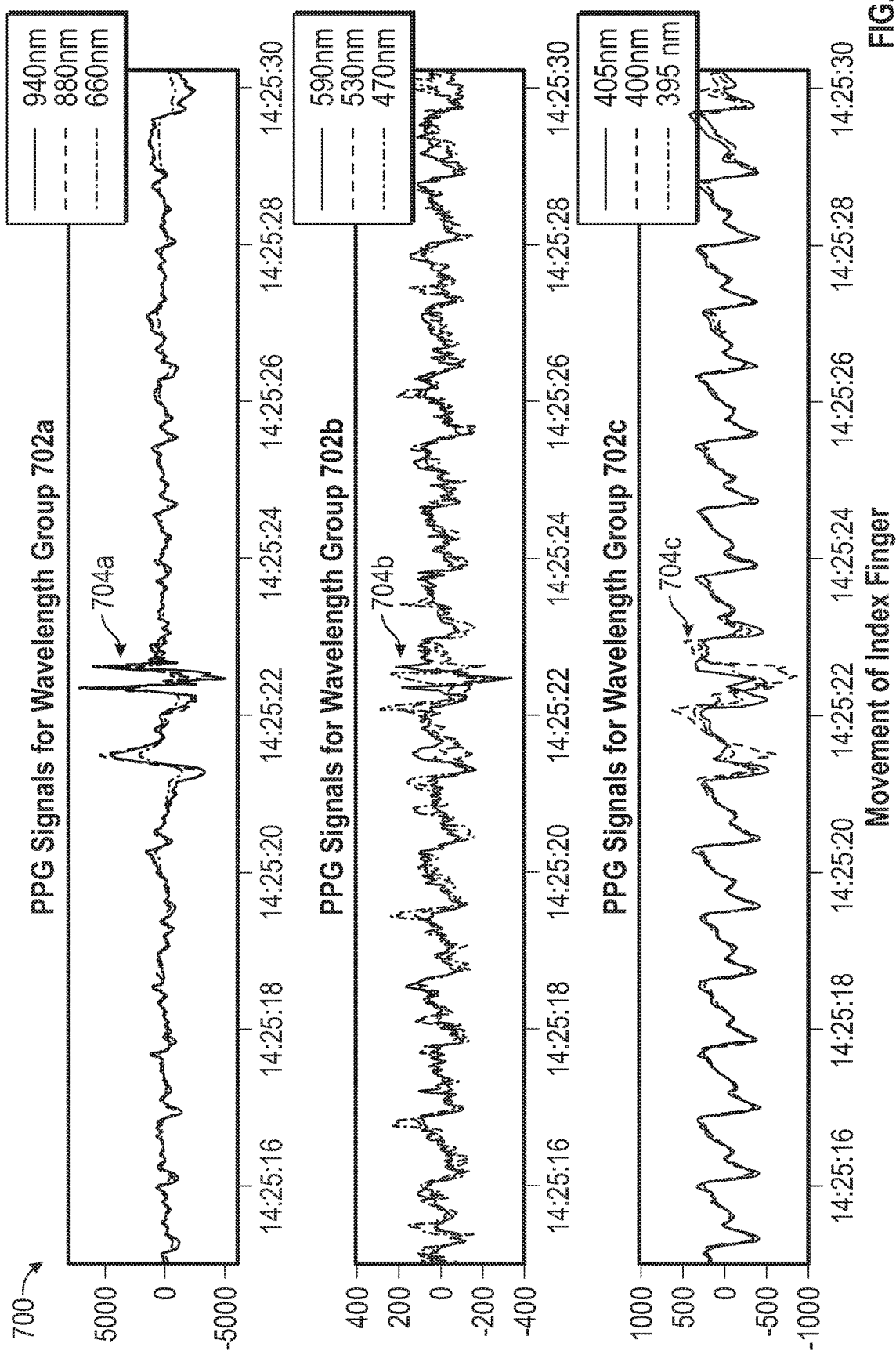
FIG. 7 illustrates a schematic diagram of a graph of spectral responses obtained using an embodiment of the biosensor during movement of an index finger on a right hand of the user.

FIG. 7 illustrates a schematic diagram of a graph 700 of spectral responses obtained using an embodiment of the biosensor 100 during movement of an index finger on a right hand of the user. The biosensor 100 is still positioned on the wrist of the right hand of the user and has not been repositioned. During this measurement period, the index finger on the right hand is moved.

Again, in this example, the biosensor 100 obtained a PPG signal around a wavelength at 940 nm, a wavelength at 880 nm and a wavelength at 660 nm as shown in the PPG Signals for Wavelength Group 702a. The biosensor 100 also obtained the spectral response for a wavelength at 590 nm, a wavelength at 530 nm and a wavelength at 470 nm as shown in the PPG Signals for Wavelength Group 702b. The biosensor 100 further obtained the spectral response for a wavelength at 405 nm, a wavelength at 400 nm and a wavelength at 395 nm as shown in the PPG Signals for Wavelength Group 702c.

The PPG signals at the plurality of wavelengths include a response to the pressure pulse wave through the vessels from the cardiac cycle. In addition, at approximately the time of 14.25.21, there is an indication of movement of the index finger in the PPG signals. The PPG signals at each wavelength have a similar pattern in response to the movement of the index finger, though the pattern 704c is less defined at the lower wavelengths in wavelength group 702c. These patterns 704a-c in the PPG signal are not present in the PPG signals with little to no movement shown in FIG. 5. In addition, these patterns 704a-c are different from the patterns 604a-c in the PPG signals due to movement of the thumb shown in FIG. 6.

Figure 8:
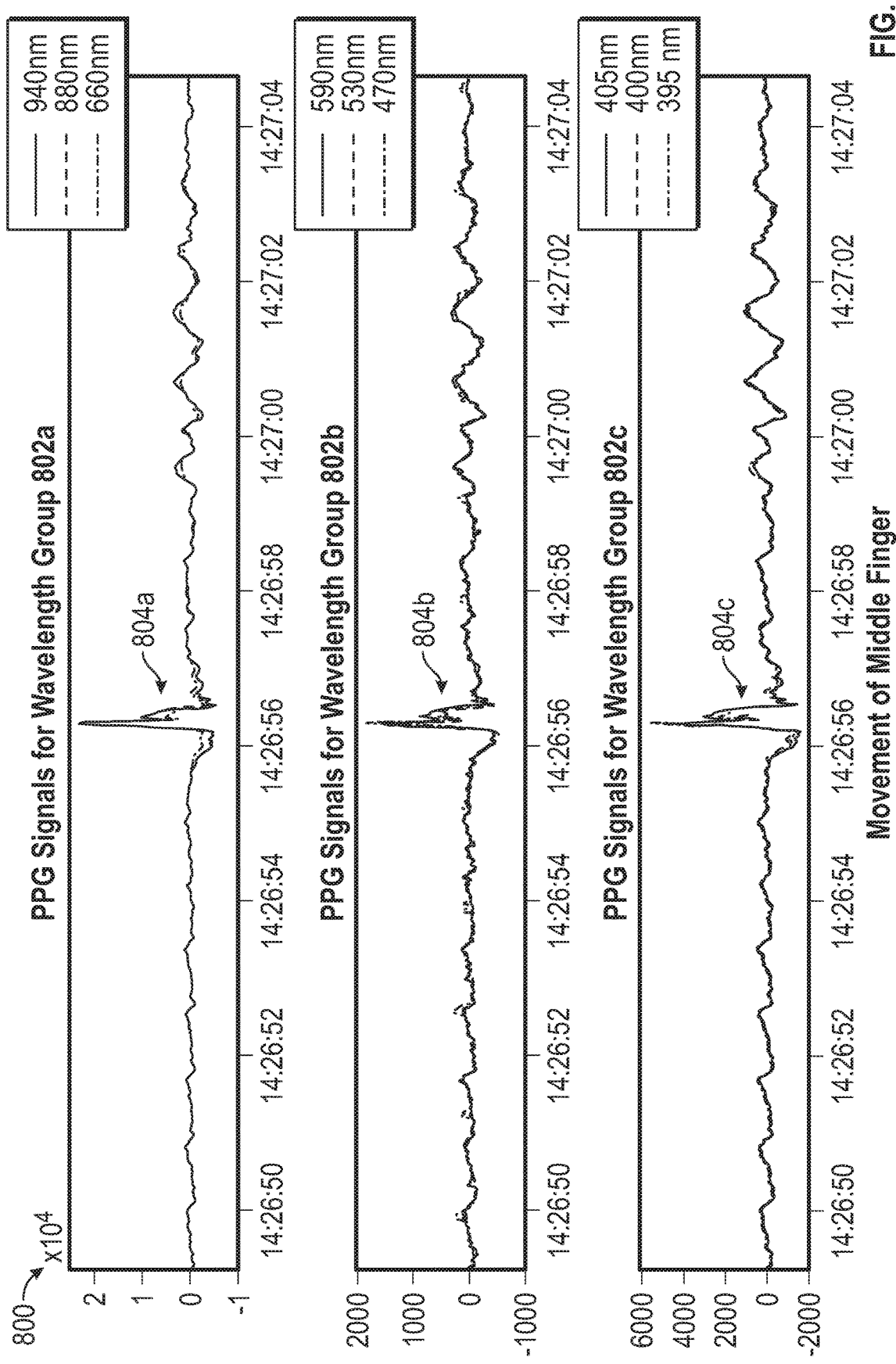
FIG. 8 illustrates a schematic diagram of a graph of spectral responses obtained using an embodiment of the biosensor during movement of a middle finger on a right hand of the user.

FIG. 8 illustrates a schematic diagram of a graph 800 of spectral responses obtained using an embodiment of the biosensor 100 during movement of a middle finger on a right hand of the user. The biosensor 100 is still positioned on the wrist of the right hand of the user and has not been repositioned. During this measurement period, the middle finger on the right hand is moved.

Again, in this example, the biosensor 100 obtained a PPG signal around a wavelength at 940 nm, a wavelength at 880 nm and a wavelength at 660 nm as shown in the PPG Signals for Wavelength Group 802a. The biosensor 100 also obtained the spectral response for a wavelength at 590 nm, a wavelength at 530 nm and a wavelength at 470 nm as shown in the PPG Signals for Wavelength Group 802*b*. The biosensor 100 further obtained the spectral response for a wavelength at 405 nm, a wavelength at 400 nm and a wavelength at 395 nm as shown in the PPG Signals for Wavelength Group 802*c*.

The PPG signals at the plurality of wavelengths include a response to the pressure pulse wave through the vessels from the cardiac cycle. In addition, at approximately the time of 14.26.56, there is an indication of movement of the middle finger in the PPG signals. The PPG signals at each wavelength have a similar pattern in response to the movement of the middle finger. These patterns 804*a-c* in the PPG signal are not present in the PPG signals with little to no movement shown in FIG. 5. In addition, these patterns 804*a-c* are different from the patterns 604*a-c* in the PPG signals due to movement of the thumb shown in FIG. 6 and from the patterns 704*a-c* in the PPG signals due to movement of the index finger shown in FIG. 7.

Figure 9:
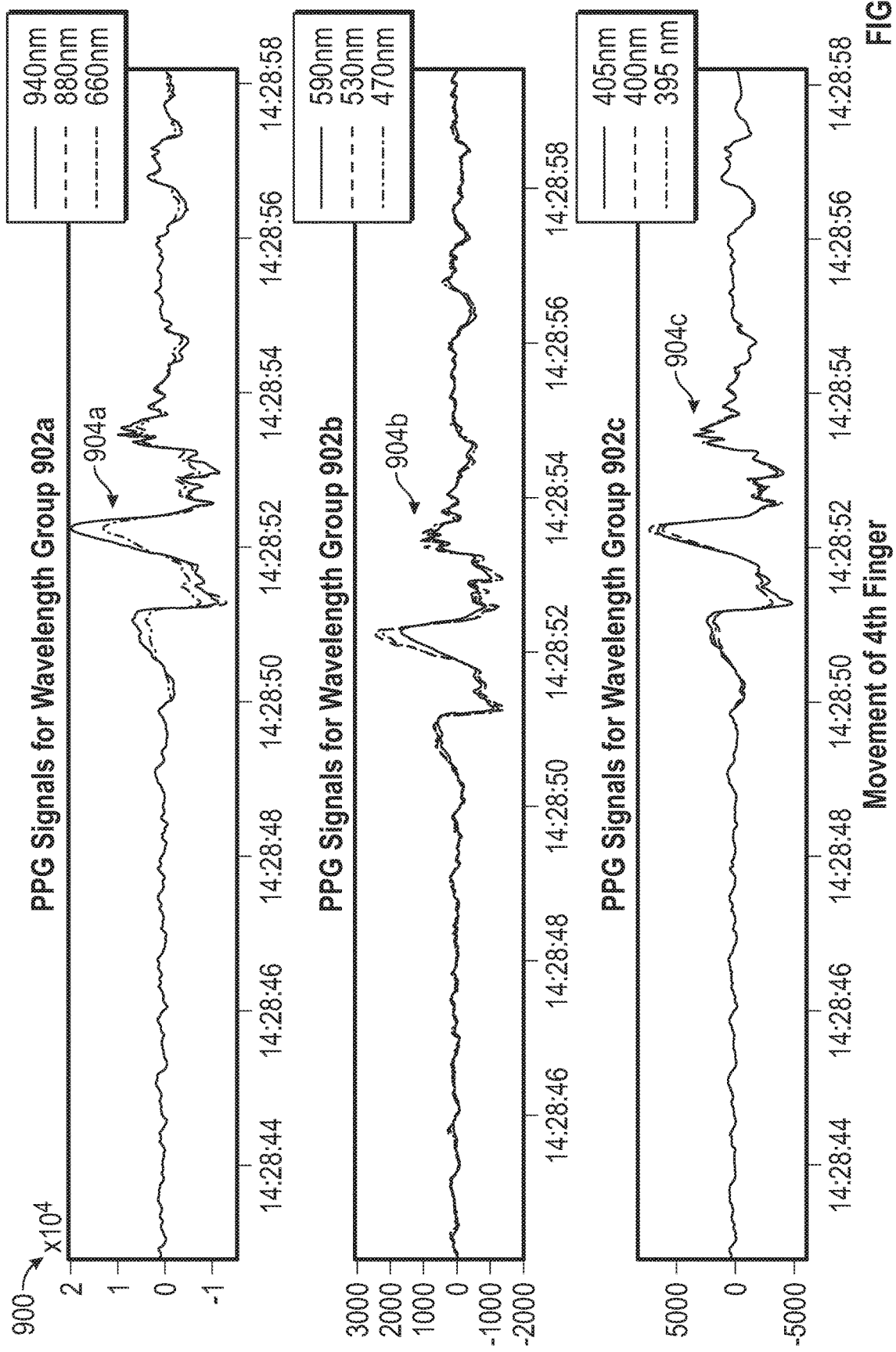
FIG. 9 illustrates a schematic diagram of a graph of spectral responses obtained using an embodiment of the biosensor during movement of a fourth finger on a right hand of the user.

FIG. 9 illustrates a schematic diagram of a graph 900 of spectral responses obtained using an embodiment of the biosensor 100 during movement of a fourth finger on a right hand of the user. The biosensor 100 is still positioned on the wrist of the right hand of the user and has not been repositioned. During this measurement period, the fourth finger on the right hand is moved.

Again, in this example, the biosensor 100 obtained a PPG signal around a wavelength at 940 nm, a wavelength at 880 nm and a wavelength at 660 nm as shown in the PPG Signals for Wavelength Group 902*a*. The biosensor 100 also obtained the spectral response for a wavelength at 590 nm, a wavelength at 530 nm and a wavelength at 470 nm as shown in the PPG Signals for Wavelength Group 902*b*. The biosensor 100 further obtained the spectral response for a wavelength at 405 nm, a wavelength at 400 nm and a wavelength at 395 nm as shown in the PPG Signals for Wavelength Group 902*c*.

The PPG signals at the plurality of wavelengths include a response to the pressure pulse wave through the vessels from the cardiac cycle. In addition, at approximately the time of 14.28.51, there is an indication of movement of the fourth finger in the PPG signals. The PPG signals at each wavelength have a similar pattern 904*a*, 904*b*, 904*c* in response to the movement of the fourth finger. These patterns 904*a-c* in the PPG signal are not present in the PPG signals with little to no movement shown in FIG. 5. In addition, these patterns 904*a-c* are different from the patterns 604*a-c* in the PPG signals due to movement of the thumb shown in FIG. 6 and from the patterns 704*a-c* in the PPG signals due to movement of the index finger shown in FIG. 7 and from the patterns 804*a-c* in the PPG signals due to movement of the middle finger shown in FIG. 8.

Figure 10:
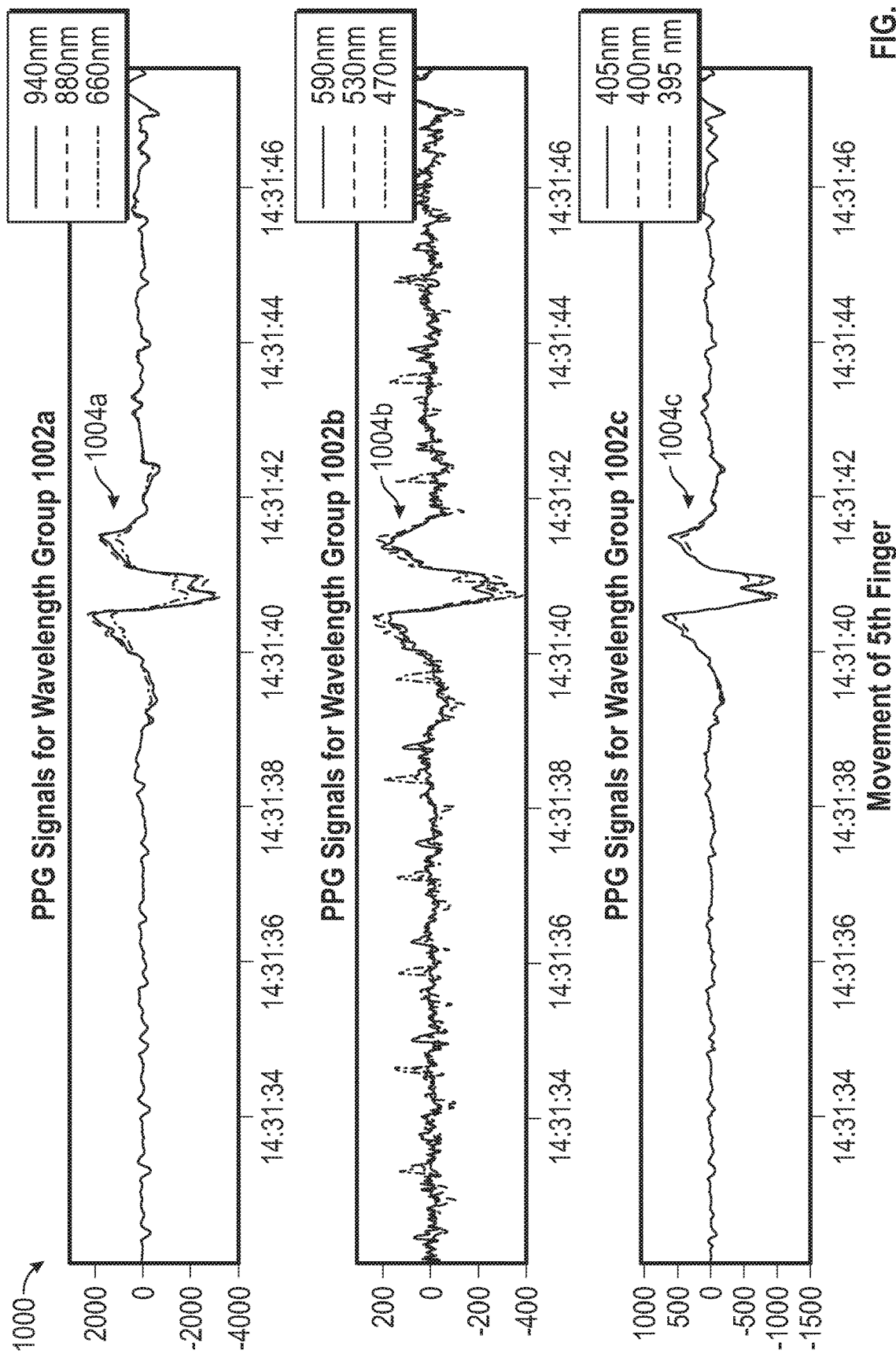
FIG. 10 illustrates a schematic diagram of a graph of spectral responses obtained using an embodiment of the biosensor during movement of a fifth finger on a right hand of the user.

FIG. 10 illustrates a schematic diagram of a graph 1000 of spectral responses obtained using an embodiment of the biosensor 100 during movement of a fifth finger on a right hand of the user. The biosensor 100 is still positioned on the wrist of the right hand of the user and has not been repositioned. During this measurement period, the fifth finger on the right hand is moved.

Again, in this example, the biosensor 100 obtained a PPG signal around a wavelength at 940 nm, a wavelength at 880 nm and a wavelength at 660 nm as shown in the PPG Signals for Wavelength Group 1002*a*. The biosensor 100 also obtained the spectral response for a wavelength at 590 nm, a wavelength at 530 nm and a wavelength at 470 nm as shown in the PPG Signals for Wavelength Group 1002*b*. The biosensor 100 further obtained the spectral response for a wavelength at 405 nm, a wavelength at 400 nm and a wavelength at 395 nm as shown in the PPG Signals for Wavelength Group 1002*c*.

The PPG signals at the plurality of wavelengths include a response to the pressure pulse wave through the vessels from the cardiac cycle. In addition, at approximately the time of 14.31.40, there is an indication of movement of the fifth finger in the PPG signals. The PPG signals at each wavelength have a similar pattern 1004*a*, 1004*b*, 1004*c* in response to the movement of the fifth finger. These patterns 1004*a-c* in the PPG signal are not present in the PPG signals with little to no movement shown in FIG. 5. In addition, these patterns 1004*a-c* are different from the patterns 604*a-c* in the PPG signals due to movement of the thumb shown in FIG. 6 and from the patterns 704*a-c* in the PPG signals due to movement of the index finger shown in FIG. 7 and from the patterns 804*a-c* in the PPG signals due to movement of the middle finger shown in FIG. 8 and from the patterns 904*a-c* in the PPG signals due to the movement of the fourth finger shown in FIG. 9.

Figure 11:
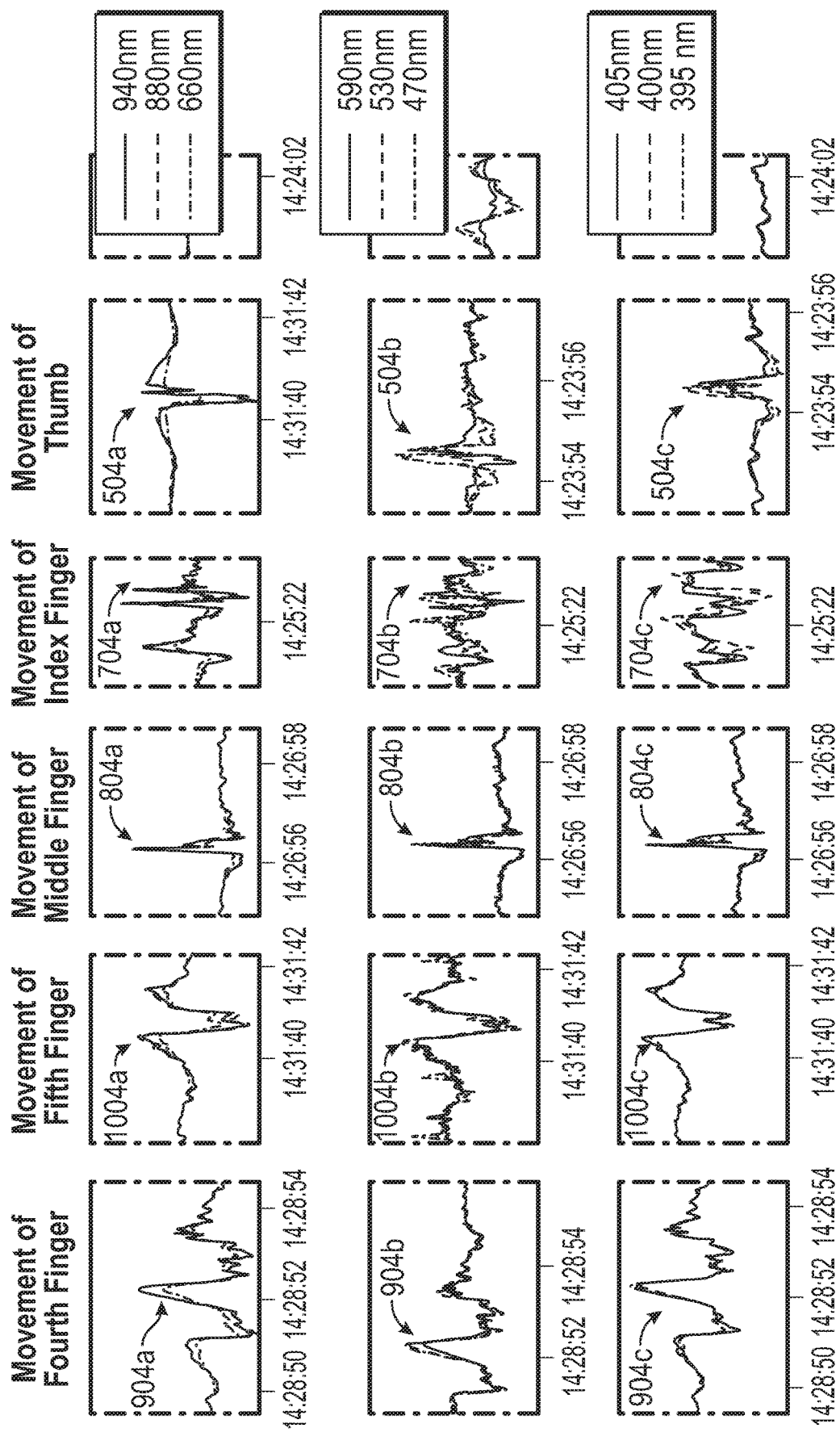
FIG. 11 illustrates a schematic diagram of a comparison of PPG signals obtained during movement of the fingers on the right hand.

FIG. 11 illustrates a schematic diagram of a comparison of PPG signals obtained during movement of the fingers on the right hand. The graphs 1100*a-e* illustrate the unique patterns in the PPG signal due to movement of the different fingers. The graphs 1100*a-e* provide a comparison of the PPG signal patterns and that the PPG signal patterns are unique and reproducible across a plurality of wavelengths.

The pattern in the PPG signal varies depending on the finger with movement. The PPG signal detected at the various wavelengths illustrate a unique pattern. Thus, the PPG signal at one or more wavelengths may be used to detect movement and determine a body part that is moving (e.g., identify one of the fingers that is moving). The PPG signals detected by the plurality of the LEDs may each be considered to determine a motion vector of a body part. For example, as shown in FIG. 11, different wavelengths may have unique PPG signal patterns for movement of a body part. The PPG pattern 704*a* due the movement of the index finger at 940 nm is different than the PPG pattern due to the movement of the index finger at 395 nm. The unique patterns at each of a plurality of wavelengths may be considered or at only a single wavelength.

Though the PPG signal was obtained by a biosensor 100 at a wrist, the PPG circuit may be positioned on the hand or above the wrist as well to detect movement and identify the specific finger that is moving. The PPG signal patterns at one or more wavelengths may thus be used to detect movement and identify the moving body part.

In addition, the PPG signal patterns vary depending on the type of movement of a body part. For example, when the index finger moves vertically up and down, a first PPG signal pattern is generated. When the index finger is retracted and extended, a second, different signal pattern is generated. The PPG signal pattern may thus be used to identify a motion vector or type of movement as well as identify the moving body part.

When we physically move our body parts, the PPG signal motion artifacts are due to neural activity (seen especially at initiation of the motion artifact), vasodilation, movement of tissue, and color hue changes due to movement/vasodilation, as explained in more detail herein. Different movements create different changes in the neural activity, vasodilation, tissue movement and color hue. As such unique PPG signal patterns are generated for different movements of a same body part. Similarly, unique PPG signal patterns are generated for a same movement of different body parts.

The biosensor may be placed on other body parts and the PPG signal may be obtained at the other body parts to detect motion data. For example, a PPG signal may be obtained from an ankle or foot region to detect movement of the foot or toes. A PPG signal may be obtained from an ear bud or glasses to detect facial movements. A biosensor implemented on a patch may be placed on any region of the body to detect movement, type of movement and identify the moving body part.

Figure 12:
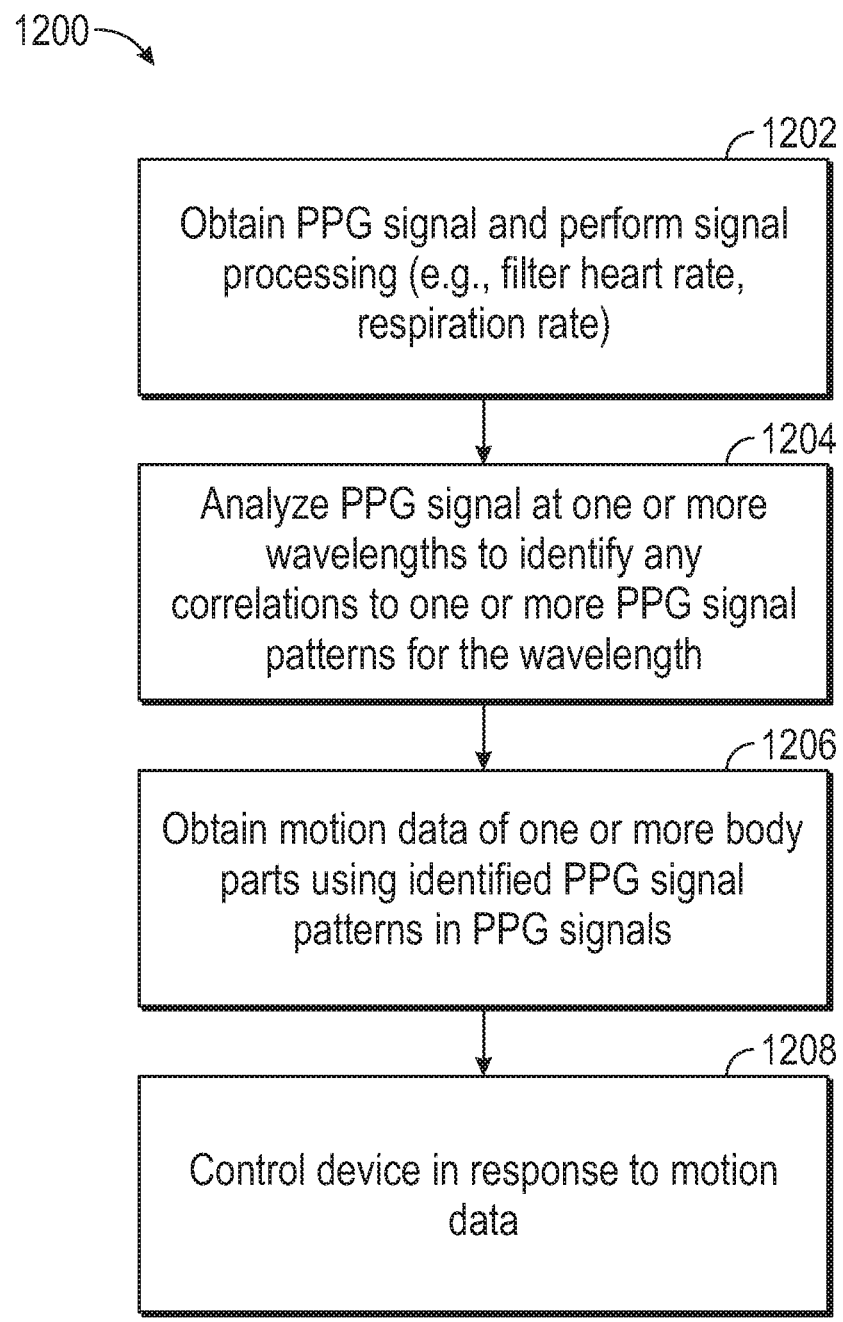
FIG. 12 illustrates a logical flow diagram of an embodiment of a method for obtaining motion data by the biosensor.

FIG. 12 illustrates a logical flow diagram of an embodiment of a method 1200 for obtaining motion data by the biosensor 100. In one aspect, the biosensor 100 emits and detects light at a plurality of predetermined frequencies or wavelengths, such as approximately 940 nm, 660 nm, 390 nm, 592 nm, and 468 nm or in ranges thereof. The light is pulsed for a predetermined period of time (such as 100 usec or 200 Hz) sequentially or simultaneously at each predetermined wavelength. In another aspect, light may be pulsed in a wavelength range of 1 nm to 50 nm around each of the predetermined wavelengths. For example, for the predetermined wavelength 390 nm, the biosensor 100 may transmit light directed at skin tissue of the user in a range of 360 nm to 410 nm including the predetermined wavelength 390 nm. For the predetermined wavelength of 940 nm, the biosensor 100 may transmit light directed at the skin tissue of the user in a range of 920 nm to 975 nm. In another embodiment, the light is pulsed simultaneously at least at each of the predetermined wavelengths (and in a range around the wavelengths).

The spectral responses are obtained around the plurality of wavelengths. This measurement process is repeated continuously, e.g., pulsing the light at 10-100 Hz and obtaining spectral responses over a desired measurement period for detection of motion. The spectral data obtained by the PPG circuit 110, such as the digital or analog spectral responses, may be processed locally by the biosensor 100 or transmitted to a central control module for processing. For example, the PPG circuit may be positioned on the skin and the PPG signals transmitted to a cell phone or other user device for processing.

The PPG signals are detected at one or more wavelengths and signal processing performed at 1202. During signal processing, the components of the PPG signal due to the cardiac cycle and respiration rate may be filtered. For example, the PPG signal at a wavelength when no motion is detected (as shown in FIG. 5) may be obtained. This PPG signal may then be filtered from subsequent PPG signals at the same wavelength.

This signal processing thus helps to isolate the motion artifacts in the PPG signal. The PPG signal patterns due to motion artifacts may have various causes. For example, the motion artifacts may be generated in response to a change in underlying tissue characteristics due to the moving tissue, changes in vasodilation due to neural stimulation or increased blood flow to the region.

The motion artifacts in the PPG signal at one or more wavelengths are compared and correlated to one or more of the predetermined PPG signal patterns for the one or more wavelengths at 1204. Pattern classification and recognition algorithms are used in conjunction with the predetermined PPG signal patterns. The PPG signals detected by a plurality of the LEDs may each be considered to determine a motion vector of a body part. For example, as shown in FIG. 11, different wavelengths may have unique PPG signal patterns for movement of a body part. The PPG pattern 704a due the movement of the index finger at 940 nm is different than the PPG pattern due to the movement of the index finger at 395 nm. A first PPG pattern at a first wavelength may correspond to a rotation of a hand while a second PPG pattern at a second wavelength may correspond to the same rotation of the hand. As such, for a more accurate detection of a motion vector, the PPG signals at a plurality of wavelengths may be analyzed to detect the unique PPG pattern for that wavelength.

In addition, a unique pattern is generated at a wavelength for movement of different body parts and different motion vectors or types of movement. For example, movement of the index finger creates a different unique pattern at a wavelength (such as 940 nm) from movement of the thumb or pinkie at the same wavelength (such as 940 nm). Unique PPG signal patterns at one or more wavelengths may be stored in a database with corresponding motion data of a body part. The motion data may include a type of movement (clenched fist, extension or retraction of finger), a motion vector (direction, speed, acceleration), etc. The PPG signal patterns at multiple wavelengths may be obtained and the corresponding motion data compared for verification.

One or more of the predetermined PPG signal patterns are recognized in the detected PPG signal. The PPG signal patterns are mapped to a moving body part as shown in FIG. 11 and may be mapped to a motion vector of a body part. For example, the motion artifact may be used to determine an acceleration of the motion or to determine a speed and direction of the movement of the body part. Thus, the motion data may include an identification of the moving body part and the type of movement (horizontal, vertical, extension, retraction, rotation, etc.) and motion vector, e.g. acceleration (speed and/or direction) data representative of an acceleration proximate to a portion of the user at 1206.

The PPG signal pattern or motion artifact is due to changes in optical properties of the underlying tissue. The changes may be due to one or more of neural activity, vasodilation of vessels, expansion and contraction of tissue (muscle skin), or change in hue of skin due to such expansion and contraction. A correlation of the motion induced artifact in the PPG signal to a corresponding muscular position may thus be performed. A DC level of the PPG signal or maximum amplitude of the motion artifact may also be measured to determine a force of the motion. Since neural activity/activation begins prior to vasodilation and muscle movement, the neural activity is superimposed on the PPG signal and is most visible at initiation of the motion artifact.

In addition to PPG signal patterns, the PPG signals may be analyzed to determine other metrics for obtaining the motion data. For example, the PPG signals may be used to determine a DC level, amplitude levels, a heart rate, respiration rate, or level of vasodilation. One or more of these metrics may also be used to obtain the motion data as well.

Control commands may be generated in response to the motion data for input to a device at 1208. The motion data may be mapped to predetermined control commands or the control commands may be determined based on a Graphical User Interface (GUI) and motion data. For example, the motion data may be used to operate a user device, such as a smart watch, smart glasses, laptop, smart tablet, smart phone, etc. The fingers may be moved to indicate typing on a virtual keyboard. Or the fingers may be moved to select icons on a GUI or move a cursor on a display without having to touch the display or device. Thus, a typical input device, such as a mouse, touchpad, keyboard, touchscreen or joystick, may be replaced using the motion detection of the biosensor 100.

The biosensor 100 may thus be used to operate a user device, such as a smart watch or smart glasses, that may otherwise be difficult to operate through a touchscreen. In one aspect, the biosensor 100 may be used to control a drone or other vehicle. The drone may be controlled intuitively by moving a hand up or down to control altitude or rotating the hand to control direction and tilt of the drone. A speed of the drone may be controlled by acceleration of the movements. The biosensor 100 using movement recognition may thus be used for providing instructions and control of a many different types of user devices or any type of electronic system needing man-machine interaction.

In another embodiment, the biosensor 100 may detect motion data relating to sign language. A biosensor 100 may be placed on both wrists of a user to determine movement and gestures of a user using PPG signals and the motion sensor. These movements may be translated to sign language, and the corresponding words reproduced to a word processing application. Thus, a person may "dictate" using sign language to the word processing application. The translation of sign language to written word using the biosensor 100 may also be used in communication applications or for translators.

Embodiment—Measuring a Level of Vasodilation

Vasodilation changes the way that the pressure wave in blood flow from the heart beat impulse propagates from the deeper, larger arteries to the shallower, smaller ones. In an embodiment described herein, this change in propagation of the pressure wave can be measured in the change in transfer function from a wavelength in the near-IR window, which penetrates the tissue deeply, to a wavelength not in the near-IR window, which penetrates tissue much less deeply. This means that by measuring the change in shape and time delay of PPG signals of two or more wavelengths, where at least one is in the near-IR window and one is not, information about vasodilation may be determined. Also, because the transfer function between the two depths of penetration is affected by blood pressure, blood viscosity, tissue absorption, and, in general, cardiovascular health, these other parameters can be characterized as well. Features or parameters of the PPG signal that can be examined to obtain a level of vasodilation include, but are not limited to, the time delay between the systolic points and diastolic points in different wavelengths and the difference in dichroitic notch suppression between wavelengths.

Figure 13:
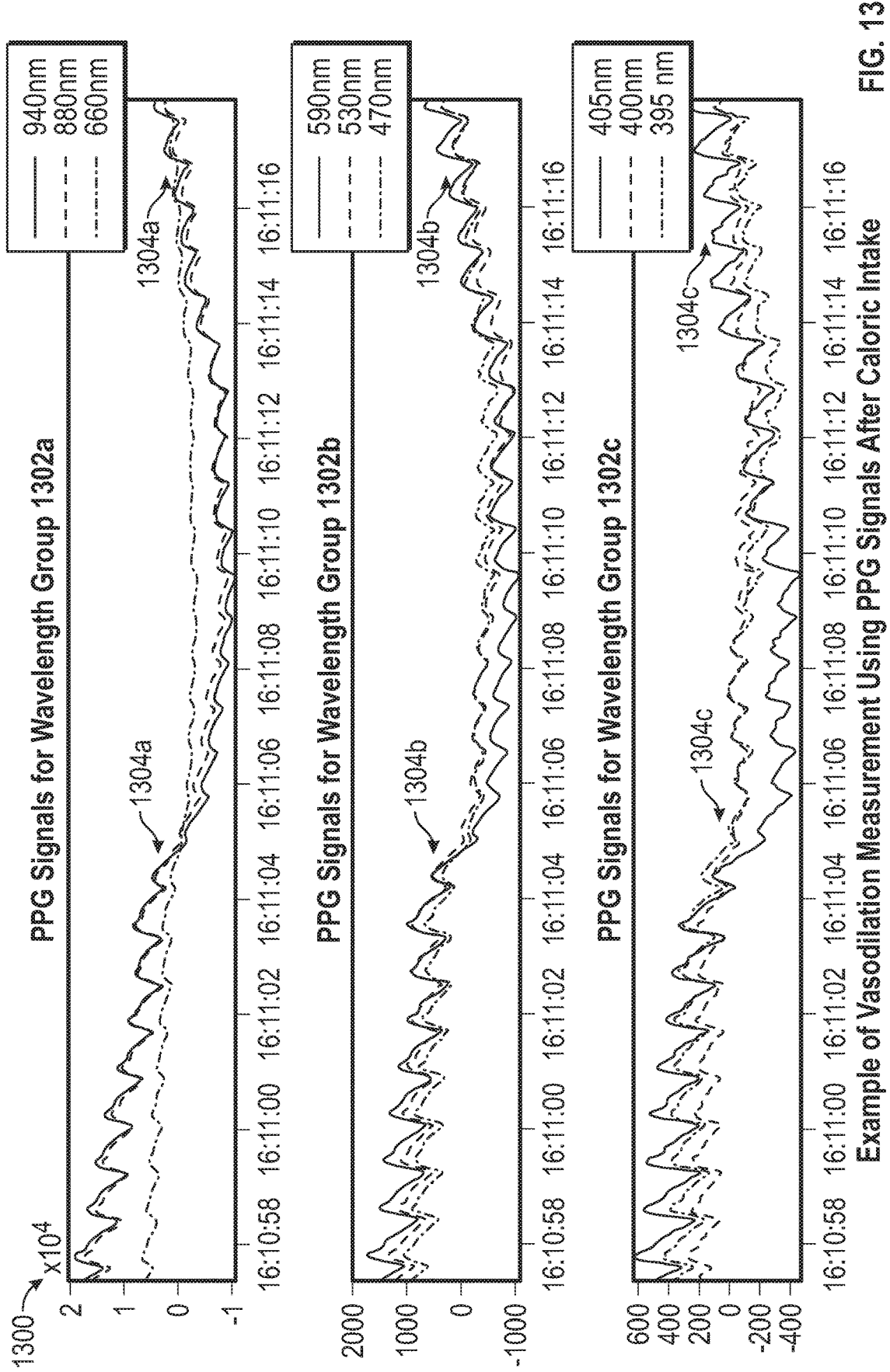
FIG. 13 illustrates a schematic diagram of a graph of PPG signals during a period of vasodilation in vessels.

FIG. 13 illustrates a schematic diagram of a graph 1300 of PPG signals during a period of vasodilation in vessels. At "rest", a body responds to caloric intake and vasodilation occurs normally as the body processes food, insulin is dispensed, and arteries expand due to Nitric Oxide (NO) causing the outer muscle of the arteries to expand temporarily. This vasodilation is reflected in the PPG signal, and highly visible in the signal to noise ratio.

The biosensor 100 obtained a PPG signal during vasodilation after caloric intake around a wavelength at 940 nm, a wavelength at 880 nm and a wavelength at 660 nm as shown in the PPG Signals for Wavelength Group 1302a. The biosensor 100 also obtained the spectral response for a wavelength at 590 nm, a wavelength at 530 nm and a wavelength at 470 nm as shown in the PPG Signals for Wavelength Group 1302b. The biosensor 100 further obtained the spectral response for a wavelength at 405 nm, a wavelength at 400 nm and a wavelength at 395 nm as shown in the PPG Signals for Wavelength Group 1302c.

As shown in the graphs, the PPG signals reflect a period of vasodilation 1304a, 1304b, 1304c of vessels. The vasodilation 1304a-c is reflected in the PPG signals during a time period between approximately 16.11.04 secs through approximately 16.11.17 secs. In particular, a lower frequency component of the PPG signals changes during the period of vasodilation 1304a-c. This lower frequency component of the PPG signals includes the lower frequencies not affected by the pulsating blood flow (pressure wave) due to the cardiac cycle.

During vasodilation, the arteries and other vessels widen changing the absorption properties of the vascular tissue. These changes in absorption properties are due, e.g., by the increase in blood in the vascular tissue and the compression of surrounding tissue due to the widening vessels. The PPG signals across wavelengths in the IR, visible and UV spectrums are affected by the changing absorption properties of the vascular tissue due to vasodilation.

The duration of the period of vasodilation and/or the intensity change of the PPG signals during the period of vasodilation may be obtained. This vasodilation data from the PPG signal may be correlated to a level of vasodilation. For example, the level of vasodilation may be expressed as a percentage change of the diameter of the artery or percentage increase in blood flow.

Figure 14:
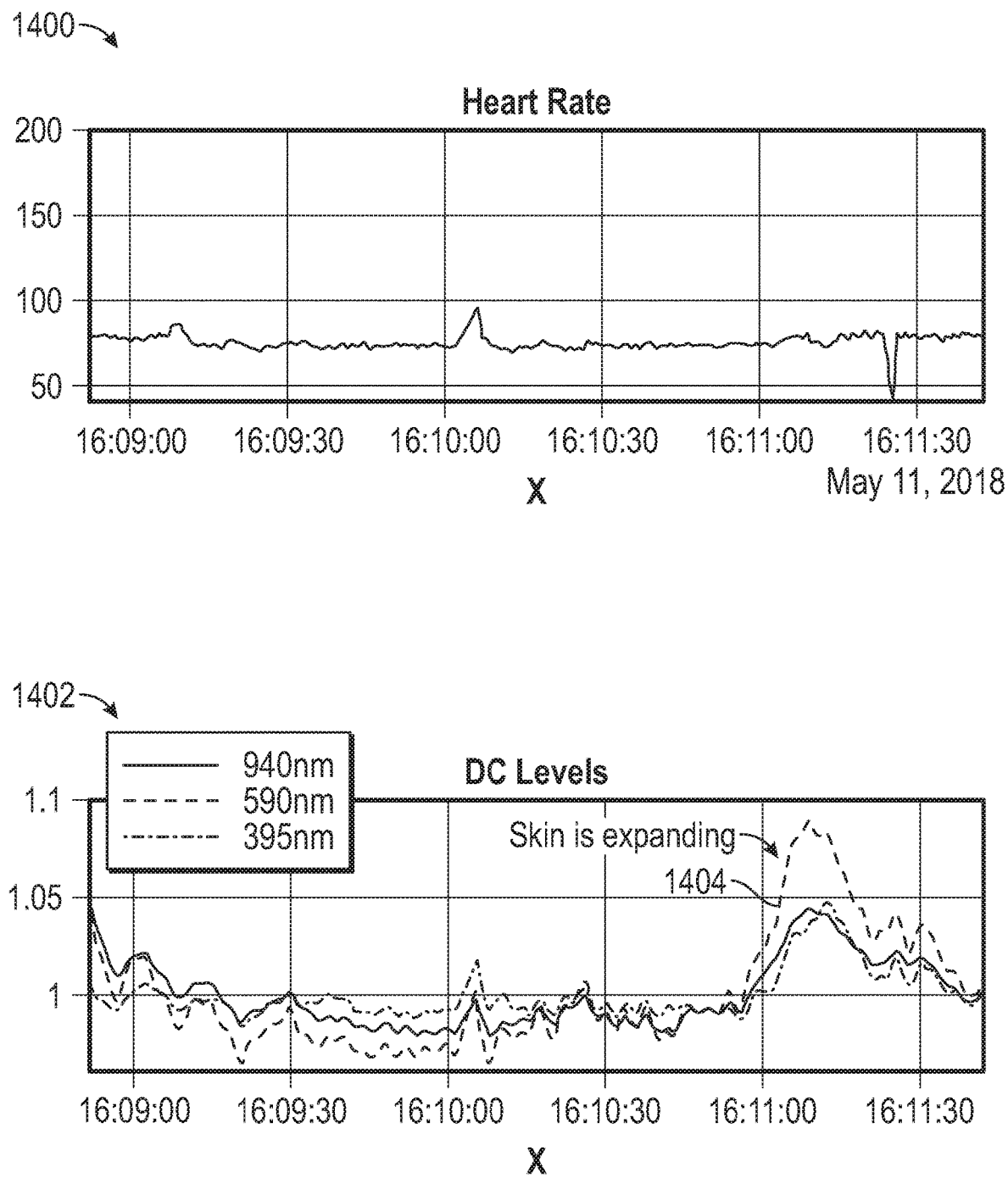
FIG. 14 illustrates a schematic diagram of heart rate and lower frequency components of PPG signals during a period of vasodilation.

FIG. 14 illustrates a schematic diagram of heart rate and lower frequency components of PPG signals during a period of vasodilation. The graph 1400 illustrates a heart rate obtained from higher frequency components of the PPG signals shown in FIG. 13. The spectral response may be filtered using digital signal processing techniques to eliminate noise and background interference to obtain a filtered spectral response. A heart rate may be determined from the spectral response. For example, the biosensor 100 may determine the time between diastolic points or between systolic points to determine a time period of a cardiac cycle. In another embodiment, to estimate the heart rate, the frequency spectrum of the PPG signal is obtained using a FFT algorithm over a predetermined period (hamming window). The pulse rate is estimated as the frequency that corresponds to the highest power in the estimated frequency spectrum. The frequency spectrum may be averaged or added over 5-10 second windows.

In addition, a respiration rate may be obtained by measuring a low frequency component of the filtered spectral response. From this low frequency component, the biosensor 100 may obtain a respiratory rate of a user from the spectral response.

The graph 1402 illustrates the lower frequency components (e.g. the frequencies not affected by pulsatile blood flow) of the PPG signals shown in FIG. 13 at 940 nm, 590 nm and 395 nm. The characteristics of the lower frequencies of the PPG signals change during the vasodilation period. The absorption properties of the vascular tissue vary due to changes in volume of blood and compression of tissue due to widening of the vessels.

In addition, the skin may expand in response to the widening vessels during vasodilation as reflected at 1404. The lower frequencies not affected by pulsatile blood flow of the 590 nm signal shows the skin pigmentation being slightly expanded. For example, the 590 nm (Yellow color) wavelength signal is a good signal to observe the melanin amount (pigment of skin). This change in skin hue due to expanding skin during vasodilation changes the absorption properties of the skin tissue around 590 nm. The PPG signals are thus affected by this change in absorption properties as seen in graph 1402.

The graph 1402 also illustrates that the PPG signals in different spectrums exhibit a time delay. For example, the PPG signal at 940 nm in the IR range, the PPG signal at 590 in the visible range, and the PPG signal at 395 in the UV range have timing differences. This time delay is due in part to the different penetration depths of the wavelengths.

The phase difference or the timing difference between PPG signals in different spectrums can be observed in similar fashion showing negative to positive timing which corresponds to the constrictions and expansion of the arteries. At a same input power, light at higher wavelengths (IR light) penetrates vascular tissue deeper than light at lower wavelengths (UV light). The optical properties of the tissue are affected by many factors, including but not limited to, skin-tone, tissue hydration, and tissue chemistry. In a sensor configuration where the light from the light source is backscattered to a sensor on the same surface, the optical signal at the sensor includes a sum of all light backscattered that makes it to the focal surface after interacting with the tissue. With the optical power being the same across all wavelengths, some of the light backscattered from the IR light penetrates deeper into the tissue than the UV light does. This means that the different wavelengths of light probe different depths of tissue.

When the heart beats, the arteries swell as fluid is pushed out of the heart. The leading edge of the swelling or pressure wave moves like a "bulge" through the arterial system. This system can be thought of as an elastically dampened hydraulic system. The pressure wave or bulge in the pulsatile blood flow will move from the lower tissue to the upper tissue. Thus, the deeper penetrating wavelengths (such as IR light) will detect a pressure wave first followed by the lesser penetrating wavelengths (such as visible then UV light). The time delay in the "bulge" or pressure wave moving from the lower tissue into the upper tissue thus creates a time delay in a pressure waveform seen in the PPG signals at different wavelengths. For example, as seen in FIG. 13, a waveform in the UV range has a time delay compared to a waveform in the IR range and visible range. This time delay in the different wavelengths is thus due to the depth of penetration into the skin of each wavelength.

Vasodilation changes the propagation of the pressure wave from the deeper, larger arteries to the shallower, smaller ones. In an embodiment described herein, this change in propagation of the pressure wave can be measured in the change in transfer function from a wavelength that penetrates the tissue deeply (e.g. in the IR range) to a wavelength that penetrates tissue much less deeply (e.g. in the visible or UV range). This means that by measuring the change in shape and time delay of PPG signals of two or more wavelengths with different penetration depths (e.g., wherein at least one is in the near-IR window and one is not), information about vasodilation may be determined. Also, because the transfer function between the two depths of penetration is affected by blood pressure, blood viscosity, tissue absorption, and, in general, cardiovascular health, these other parameters can be characterized as well. Features or parameters of the PPG signal that can be examined include, but are not limited to, the time delay between the systolic points and diastolic points in different wavelengths and the difference in dicrotic notch suppression between wavelengths.

Figure 15A:
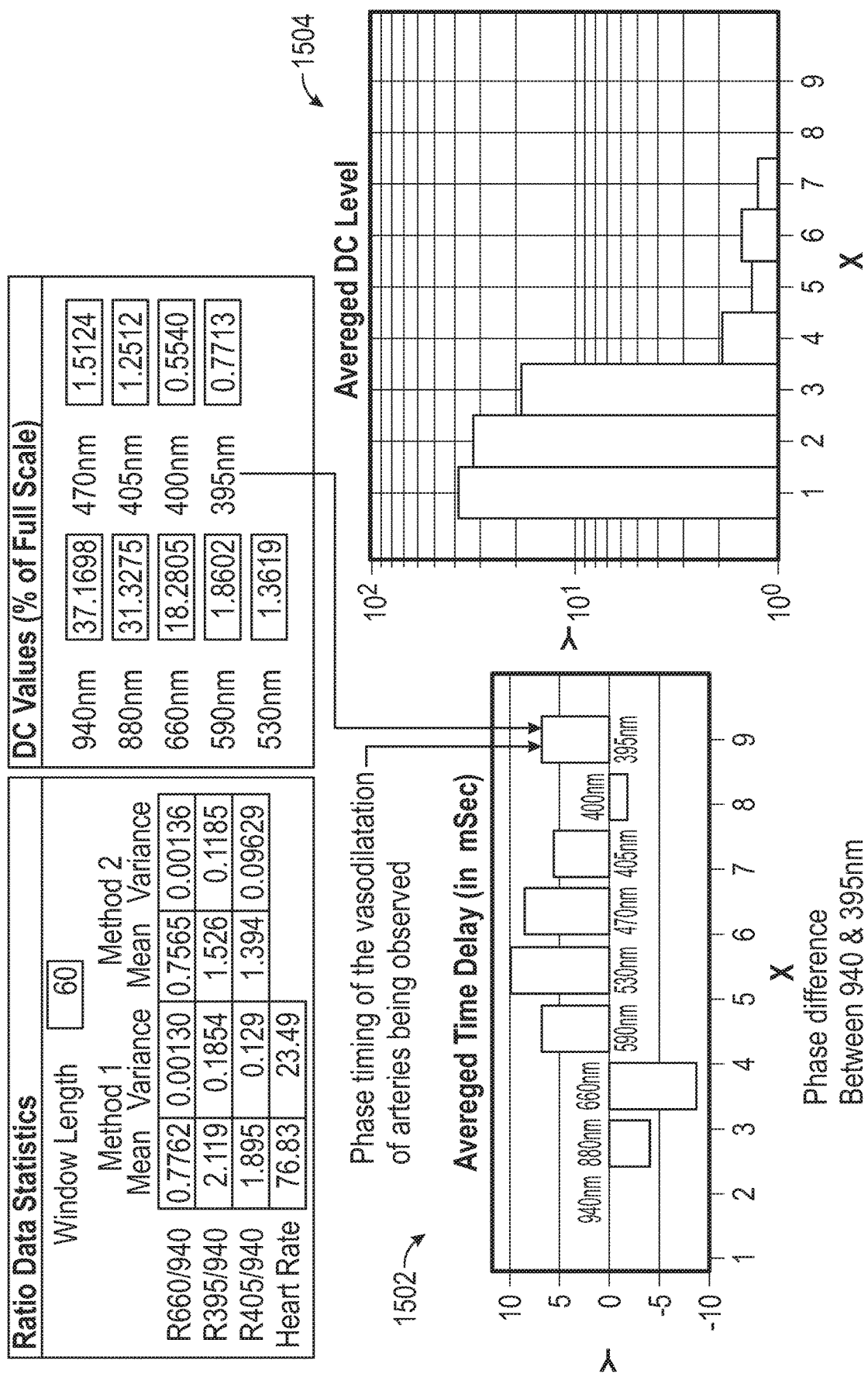
FIG. 15A illustrates a schematic diagram of graphs of the phase difference of the PPG signals at different wavelengths during a period of vasodilation.
Figure 15B:
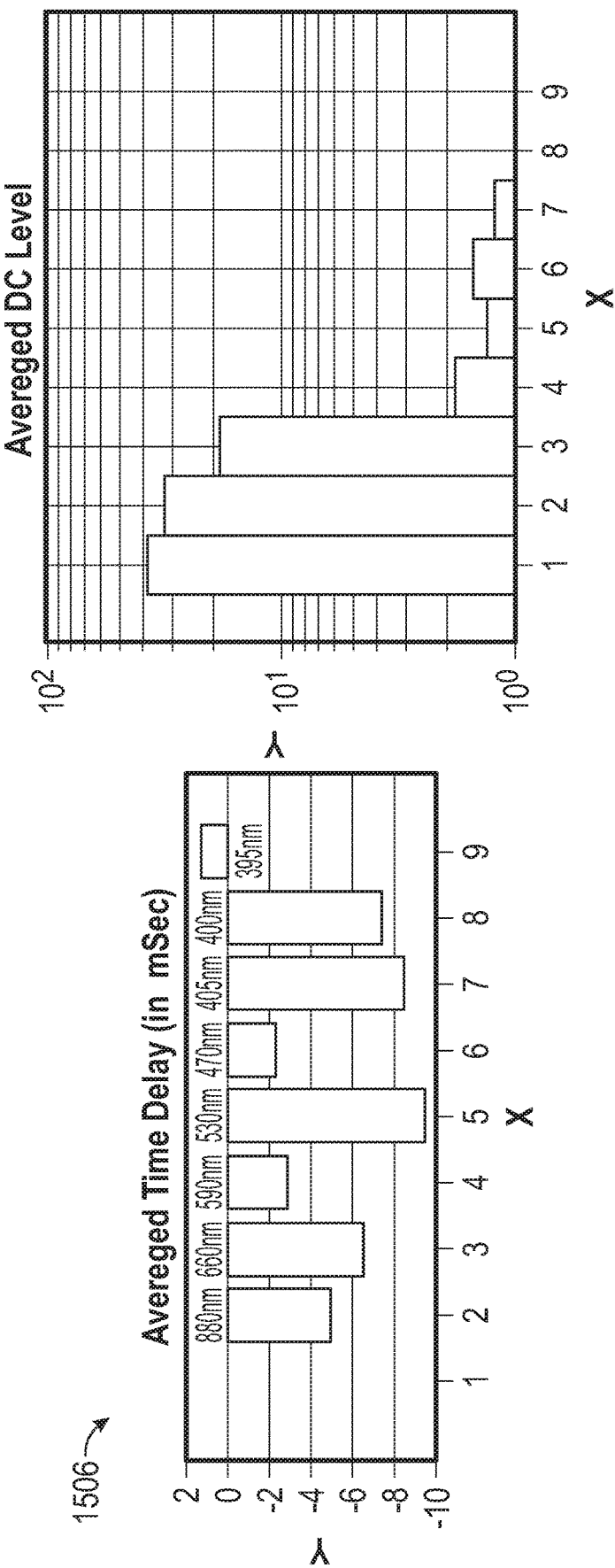
FIG. 15B illustrates a schematic diagram of graphs of the average phase difference between waveforms in PPG signals of various wavelengths after the period of vasodilation.

FIG. 15A and FIG. 15B illustrate schematic diagrams of graphs that illustrate time difference between PPG signals of various wavelengths during a period of vasodilation after caloric intake and a period with no vasodilation. FIG. 15A illustrates a schematic diagram of graphs of the phase difference of the PPG signals at different wavelengths during a period of vasodilation. In graph 1502, the phase difference is measured with respect to the PPG signal at 940 nm and so the phase delay shown is zero for 940 nm. The last shown phase difference is between PPG signals at 395 nm and 940 nm. The phase difference or the timing difference between PPG signals in graph 1502 illustrates a negative to positive timing which corresponds to the constrictions and expansion of the arteries during vasodilation. The phase delay between the PPG signals at different wavelengths is thus seen during a period of vasodilation.

The graph 1506 illustrates the average "DC values" in PPG signals of various wavelengths during the period of vasodilation. The "DC values" $I_{DC}$ may include low frequencies not generally affected by the pulsatile blood flow. The graph 1506 illustrates that the average DC values $I_{DC}$ are above a baseline normal during the period of vasodilation. The average DC values increase due to vasodilation, tissue characteristics of contracting or expanding muscles and is proportional to the force applied to the muscle. So, the DC value (low frequencies not generally affected by the pulsatile blood flow) can be used to determine a force applied during the movement.

FIG. 15B illustrates a graph 1506 of the average phase difference between waveforms in PPG signals of various wavelengths after the period of vasodilation. The phase difference is measured with respect to the PPG signal at 940 nm and so the phase delay shown is zero for 940 nm. The last shown time difference is between 395 nm and 940 nm. This graph 1506 illustrates that the baseline time differences return after the period of vasodilation. The change in phase difference between one or more different wavelengths may thus be used to determine a level of vasodilation and/or the period of vasodilation.

The graph 1508 illustrates the average DC values $I_{DC}$ PPG signals of various wavelengths after the period of vasodilation. The DC values $I_{DC}$ may include low frequencies not generally affected by the pulsatile blood flow. The graph 1508 illustrates that the average DC values $I_{DC}$ return to a baseline normal after the period of vasodilation. The change in $I_{DC}$ in one or more different wavelengths may thus be used to determine a level of vasodilation and/or the period of vasodilation. The U.S. Provisional Application No. 62/675, 151 entitled, "SYSTEM AND METHOD OF A BIOSENSOR FOR DETECTION OF VASODILATION," to Robert Newberry, filed May 22, 2018 provides additional details on measurement of a level of vasodilation and is hereby incorporated by reference herein.

Though these measurements in FIGS. 13-15 were obtained during rest after caloric intake, PPG signals after neural activation also reflect vasodilation. When a body part physically moves, the PPG signal motion artifacts are due to neural activity (at initiation), vasodilation, movement of tissue, and color hue changes due to movement/vasodilation. These factors generate the unique signal patterns or motion artifacts in the PPG signals.

Figure 16:
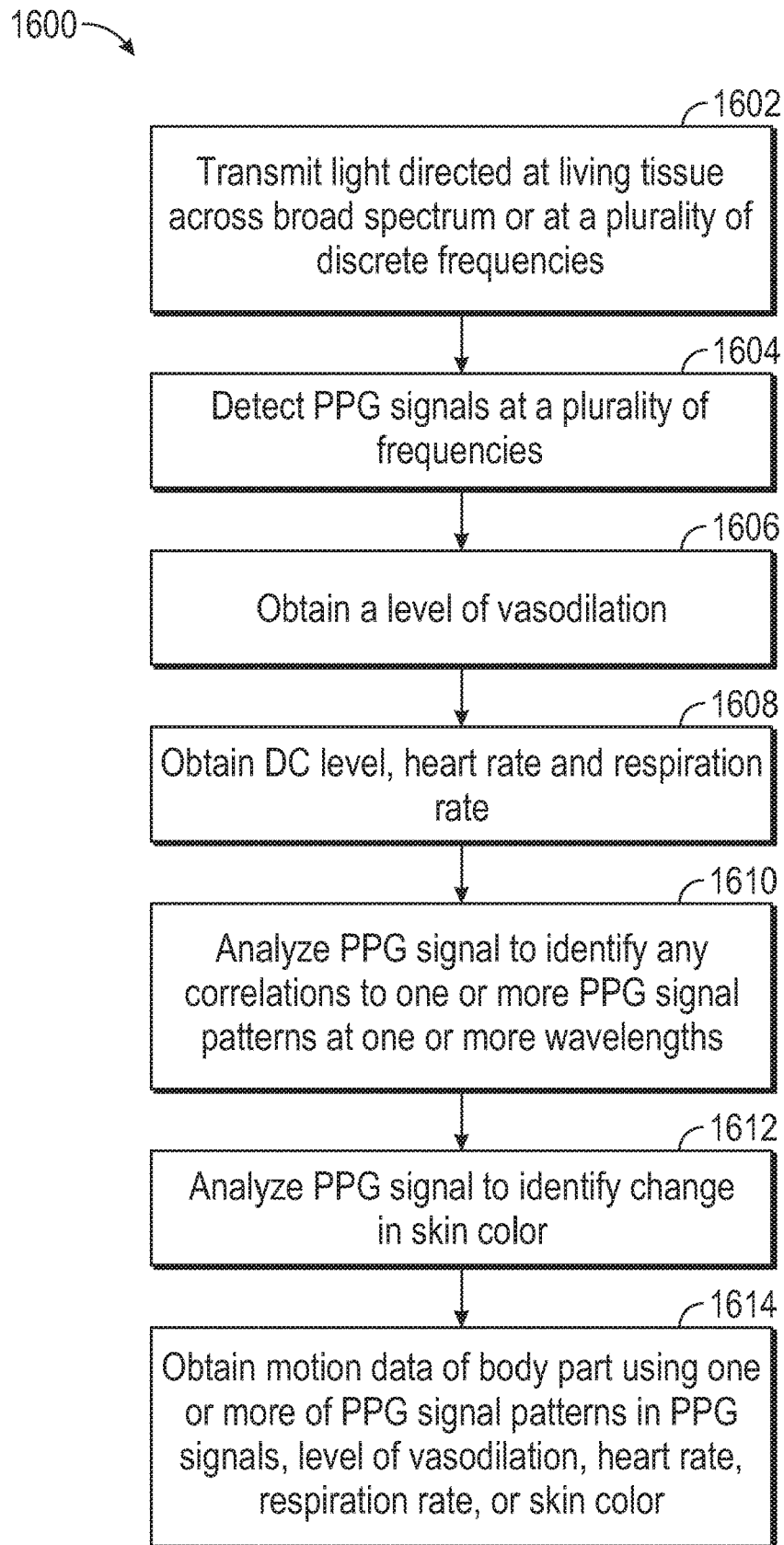
FIG. 16 illustrates a logical flow diagram of an embodiment of another method for obtaining motion data by the biosensor.

FIG. 16 illustrates a logical flow diagram of an embodiment of another method 1600 for obtaining motion data by the biosensor 100. The biosensor 100 transmits light at a plurality of discrete wavelengths at skin or living tissue of a user at 1602. Alternatively, the biosensor 100 may use a broad spectrum light source to emit light across one or more spectrums. The biosensor 100 detects light reflected from or transmitted through the tissue of the user and generates PPG signals at a plurality of wavelengths at 1604.

The biosensor 100 may use one or more types of data to detect motion and obtain motion data. For example, the biosensor 100 may process the PPG signals to obtain a level of vasodilation at 1606. The level of vasodilation may be indicative of movement or neural stimulation of a body part.

The biosensor 100 may also obtain a heart rate, respiration rate and DC level from the PPG signals at 1608. The biosensor 100 may also analyze the PPG signals to identify any correlations with a PPG signal pattern indicating movement at one or more wavelengths at 1610. The biosensor 100 may also analyze the PPG signal pattern at visible light ranges (yellow, red) to determine any change in the skin color or hue at 1612.

The biosensor 100 may then obtain motion data using one or more of the identified PPG signal patterns in the PPG signals, the level of vasodilation, DC level, the heart rate, the respiration rate or skin color at 1614. The motion data obtained by multiple means may be compared for verification.

Embodiment—Neural Network for Motion Detection

In an embodiment, an artificial neural network may be implemented to process the PPG signal for detection of movement. For example, neural networks may be used to determine movement and direction of movement from input data. The input includes for example, the PPG signals at one or more wavelengths. Neural network models can be viewed as simple mathematical models defining a function $f$ wherein $f:X\rightarrow Y$ or a distribution over X or both X and Y. Types of neural network engines or APIs currently available include, e.g. TensorFlow™, Keras™, Microsoft® CNTK™, Caffe™, Theano™ and Lasagne™.

Sometimes the various machine learning techniques are intimately associated with a particular learning rule. The function $f$ may be a definition of a class of functions (where members of the class are obtained by varying parameters, connection weights, thresholds, etc.). The neural network learns by adjusting its parameters, weights and thresholds iteratively to yield desired output. The training is performed using defined set of rules also known as the learning algorithm. Machine learning techniques include ridge linear regression, a multilayer perceptron neural network, support vector machines and random forests. For example, a gradient descent training algorithm is used in case of supervised training model. In case, the actual output is different from target output, the difference or error is determined. The gradient descent algorithm changes the weights of the network in such a manner to minimize this error. Other learning algorithms include back propagation, least mean square (LMS) algorithm, etc. A set of examples or a training set is used for learning by the neural network. The training set is used to identify the parameters [e.g., weights] of the network.

Figure 17:
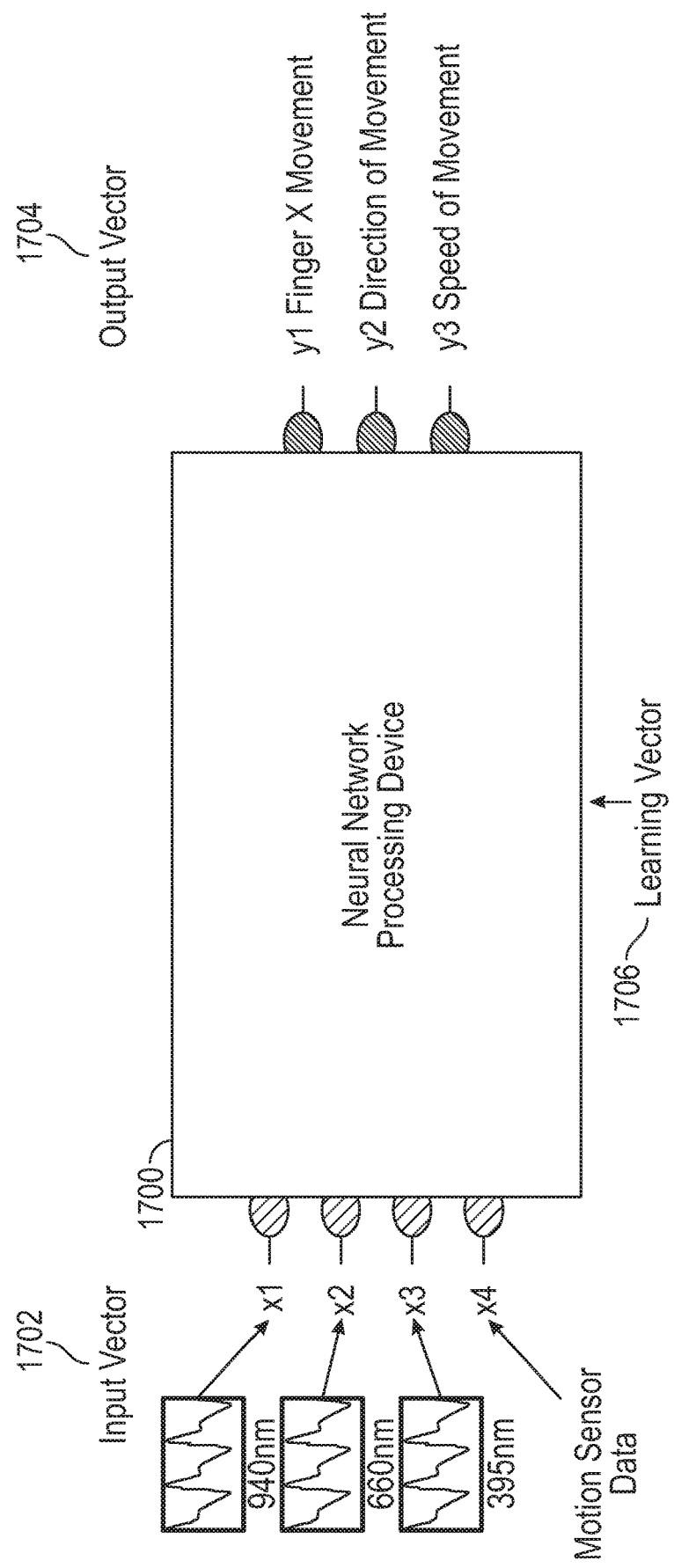
FIG. 17 illustrates a schematic block diagram of an embodiment of a neural network processing device.

FIG. 17 illustrates a schematic block diagram of an embodiment of a neural network processing device 1700. The neural network processing device 1700 obtains or generates an input vector 1702. In this embodiment, the input vector includes at least one or more PPG signals at one or more wavelengths. The input vector may also include a position of the biosensor on the user (wrist, ankle, etc.), an identification of the wavelengths of the PPG signals, an intensity level of the LED light sources, etc. The input vector may also include motion sensor data from an accelerometer or gyroscope, such as direction and velocity of detected movement or a plane of the hand.

The neural network processing device 1700 may be pre-configured with weights, parameters or other learning vectors 1706 derived from a training set. The training set preferably included sets with the same type of information in the input vector and known movements of various body parts in various combinations. For example, the PPG signals may be obtained while various finger movements are made. This training set is provided to a neural network training algorithm to generate the learning vector 1706. The training set may include further motion sensor data as well as a position of the biosensor, a body part from which the PPG signal is obtained, an identification of the wavelength, etc.

The neural network processing device 1700 then obtains an output vector 1704. The output vector includes motion data, such as an identification of movement of a body part (such as Finger X), or a type of movement or a direction of movement or acceleration and speed of the movement.

Figure 18:
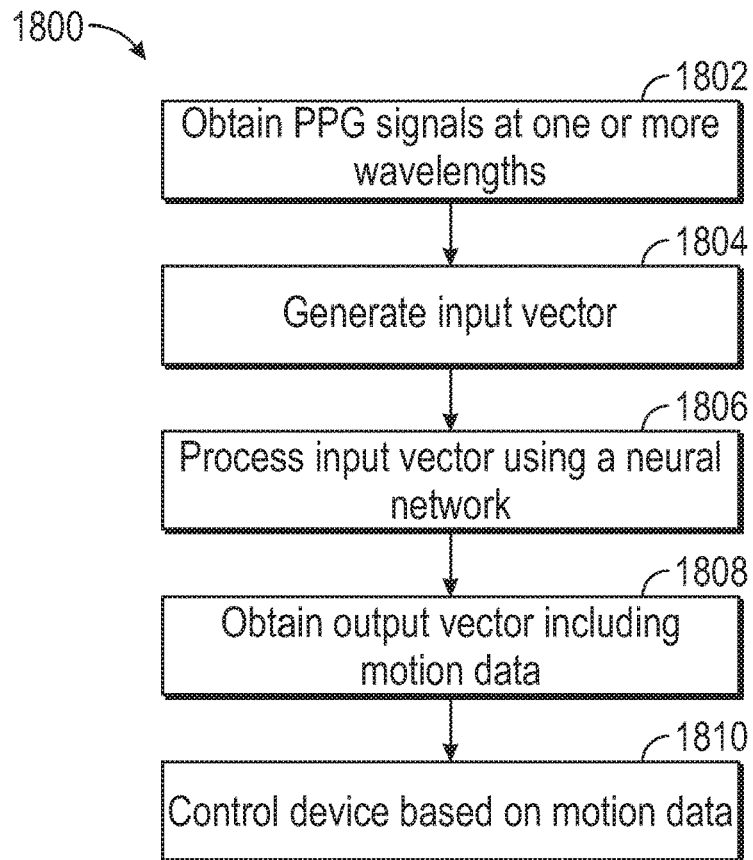
FIG. 18 illustrates a logical flow diagram of an embodiment of a method for using machine learning techniques for motion detection using PPG signals at one or more wavelengths.

FIG. 18 illustrates a logical flow diagram of an embodiment of a method 1800 for using machine learning techniques for motion detection using PPG signals at one or more wavelengths. PPG signals at one or more wavelengths are obtained at 1802. Various parameters of the PPG signals may be determined or measured. These parameters include the diastolic and systolic points, the L values, R values, pulse shape (measured by autoregression coefficients and moving averages), characteristic features of the shape of the PPG waveform, the average distance between pulses, variance, instant energy information, energy variance, etc. Other parameters may be extracted by representing the PPG signal as a stochastic auto-regressive moving average (ARMA). Parameters also may be extracted by modeling the energy of the PPG signal using the Teager-Kaiser operator, calculating the heart rate and cardiac synchrony of the PPG signal, and determining the zero crossings of the PPG signal. These and other parameters may be obtained from the one or more PPG signals and included as PPG input data.

An input vector is generated at 1804. The input vector includes the PPG input data, such as the PPG signals at one or more wavelengths and/or one or more parameters generated from the PPG signals at the one or more wavelengths. Since the PPG signal is of variable duration, a fixed dimension vector for a measurement of the PPG signal may be obtained. The input vector may also include motion sensor data.

The input vector is processed by a processing device executing a neural network (aka machine learning algorithm). The processing device executes the machine learning algorithm using the input vector at 1806 and determines motion data at 1808. The motion data includes one or more of: identification of a moving body part, direction of movement, speed/acceleration of movement, etc. The direction of the movement may be identified with respect to an identified plane or with respect to another body part. The obtained motion data may then be used to control a device at 1810.

Figure 19:
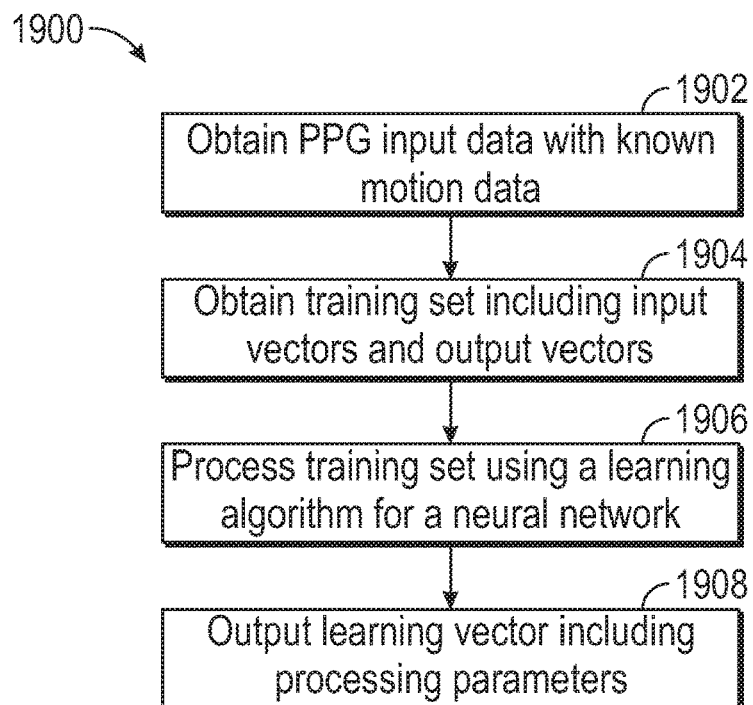
FIG. 19 illustrates a logical flow diagram of an embodiment of a method of generating a learning vector from a training set.

FIG. 19 illustrates a logical flow diagram of an embodiment of a method 1900 of generating a learning vector 1706 from a training set. During a learning stage, a neural network adjusts parameters, weights and thresholds iteratively to yield a known output vector from an associated input vector. The training is performed using defined set of rules also known as the learning algorithm. For example, a gradient descent training algorithm is used in case of supervised training model. In case, the actual output is different from target output, the difference or error is determined. The gradient descent algorithm changes the weights of the network in such a manner to minimize this error. Other learning algorithms include back propagation, least mean square (LMS) algorithm, etc. A set of examples or a training set is used for learning by the neural network. The training set is used to identify the parameters [e.g., weights] of the neural network.

The input vectors and known output vectors are included in the training set. In an embodiment, the training set is obtained in a clinical setting. For example, a biosensor or non-contact camera obtains one or more PPG signals of a body part. The body part is moved in a measured direction at a measured speed. Accelerometer data may also be obtained. The PPG input data and accelerometer data are thus obtained with known motion data at 1902.

The PPG input data is determined from the PPG signals, as described hereinabove. The input vector is then derived from the PPG input data and motion sensor data. The output vector is also generated from the motion data. The training set preferably includes a plurality of input vectors and corresponding output vectors. In an embodiment, the training is performed for each individual user. In another embodiment, training is performed from measurements of a general population.

The training set is processed at 1906 using a learning algorithm for a neural network. The neural network determines a learning vector, e.g. processing parameters. The estimator function system may work blindly, in the sense that no functional restriction is imposed on the relationship between the waveform shapes and movements. In an embodiment, the machine learning algorithm may include one or more of: a "random forest", deep belief network trained using restricted Boltzmann machines, or support vector machine. The analysis may use any known regression analysis technique, such as, for example and without limitation, random forests, support vector machines, or a deep belief network trained using restricted Boltzmann machines.

The learning vector 1706 is generated at 1908 and may include one or more processing parameters. The learning vector 1706 including processing parameters are provided to the biosensor 100 or neural network processing device 1700. The neural network processing device 1700 is configured with the processing parameters in the learning vector 1706. The neural network processing device may then process input vectors derived using PPG signals to obtain output vectors including motion data.

In an embodiment, the input vector is derived from one or more PPG signals at one or more wavelengths, such as of 390 nm, 660 nm, 440 nm, 468 nm, 530 nm, 550 nm, 592 nm, 880 nm, 940 nm or in a range of +/−20 nm from these wavelengths. The PPG signals are measured over a time period, such as 2-3 cardiac cycles. The light in the UV range, such as 390 nm or in a range of +/−20 nm, reflected from certain body parts provides an improved PPG signal. For example, UV light reflected from a face provides an improved PPG signal, especially in non-contact PPG imaging systems.

In an embodiment, the training set is continually updated, e.g. from user input. The learning vector 1706 may be periodically updated (such as hourly, daily, etc.). The updated learning vector 1706 may then be obtained and configured on the neural network processing device 1700 periodically as well (such as hourly, daily, etc.). In addition, a user may update a learning vector 1706 based on a tutorial or program that instructs a user to move certain body parts while PPG signals are measured. These measurements may be taken over a few minutes, hours, days or weeks to calibrate a neural network processing device 1700 to generate a user's training set. This training set may be used to update the learning vector 1706 for the user's neural network processing device 1700.

Figure 20:
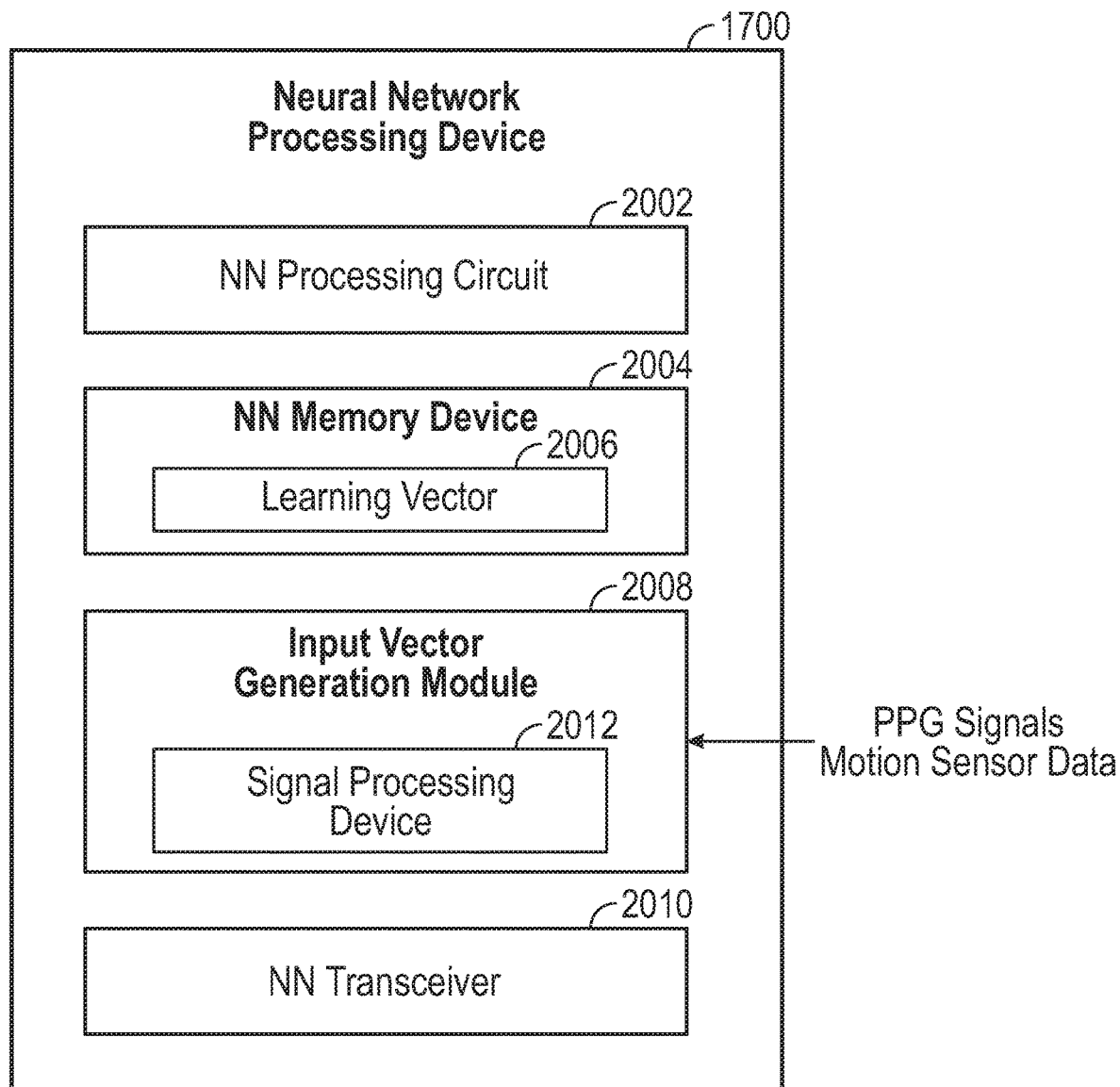
FIG. 20 illustrates a schematic block diagram of an embodiment of a neural network processing device in more detail.

FIG. 20 illustrates a schematic block diagram of an embodiment of a neural network processing device 1700 in more detail. The neural network (NN) processing device 1700 includes a NN processing circuit 2002 and NN memory device 2004. The NN memory device 2004 stores a learning vector 1706 and updates thereto. An input vector generation module 2008 is configured to generate the input vector 1702 from PPG signals and accelerometer data. The PPG signals may be obtained by a PPG circuit 110 or a non-contact camera. A signal processing circuit 2012 may be incorporated into the NN processing device 1700 to process the PPG signals to generate the PPG input data.

The input vector generation module 2008 generates an input vector 1702 including the PPG input data and/or the motion sensor data. The NN processing circuit 2002 is configured to implement a machine learning algorithm configured with the learning vector 1706. The NN processing circuit 2002 may also compare the output vector 1704 to thresholds in the output vector to calibrate or verify the results. The NN transceiver 2010 may transmit the output vector 1704 and input vector 1702 to another device, such as smart phone, smart watch, laptop, or other user device.

The NN processing device 1700 may be pre-configured with learning parameters, e.g. from a learning vector generated using a training set of a general population. The training set includes a similar data in an input vector and known results in an output vector. The learning vector may then be updated based on a user's PPG signals and indicated movements.

In another embodiment, the NN processing device 1700 may also determine a heart rate, e.g. from a high frequency component of the PPG signal or systolic and diastolic points of the PPG signal. In addition, the NN processing device 1700 may determine a low frequency component of a PPG signal to obtain a respiration rate or level of vasodilation. In another embodiment, characteristic features of the PPG waveform, such as amplitudes and phases of cardiac components, may be extracted and used to train the neural network to determine a blood pressure. See, e.g., Xing X, Sun M., "Optical blood pressure estimation with photoplethysmography and FFT-based neural networks." Biomedical Optics Express. 2016; 7(8):3007-3020, which is hereby incorporated by reference herein.

Figure 21:
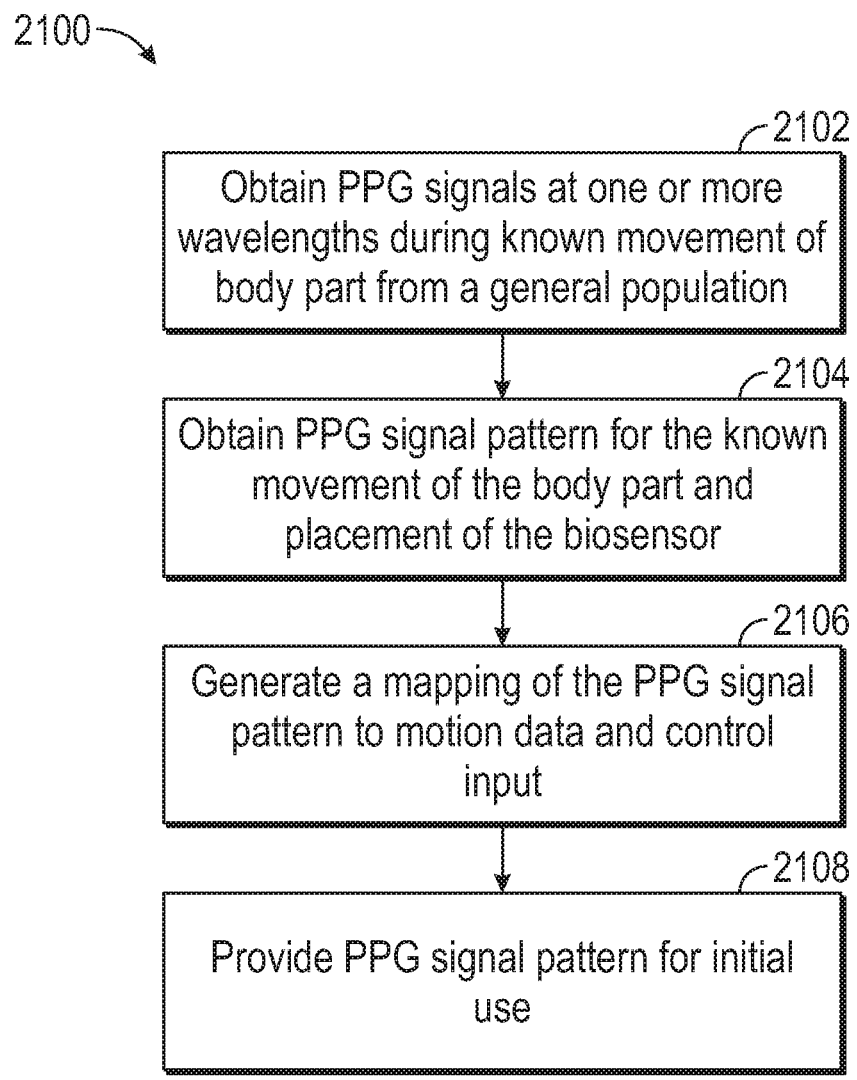
FIG. 21 illustrates a logical flow diagram of an embodiment of a method for generating PPG signal patterns.

FIG. 21 illustrates a logical flow diagram of an embodiment of a method 2100 for generating PPG signal patterns. PPG signals are obtained at one or more wavelengths during known movement of a body part at 2102. The PPG signals are collected from test subjects in the general population as test samples. Preferably, the PPG signals are detected at a same position during each test. A template for a PPG signal pattern is generated from the test samples at 2104. The PPG signal pattern is stored in a database or file with corresponding motion data, e.g. the known movement of the body part at 2106. The PPG signal pattern may also be associated with a command or instruction for controlling a device. The PPG signal pattern and associated data may be stored in a file or database and provided to the biosensor for initial use at 2108. For example, the PPG signal patterns may be used as a starting pattern to identify movement of a body part from PPG signals of a user.

Figure 22:
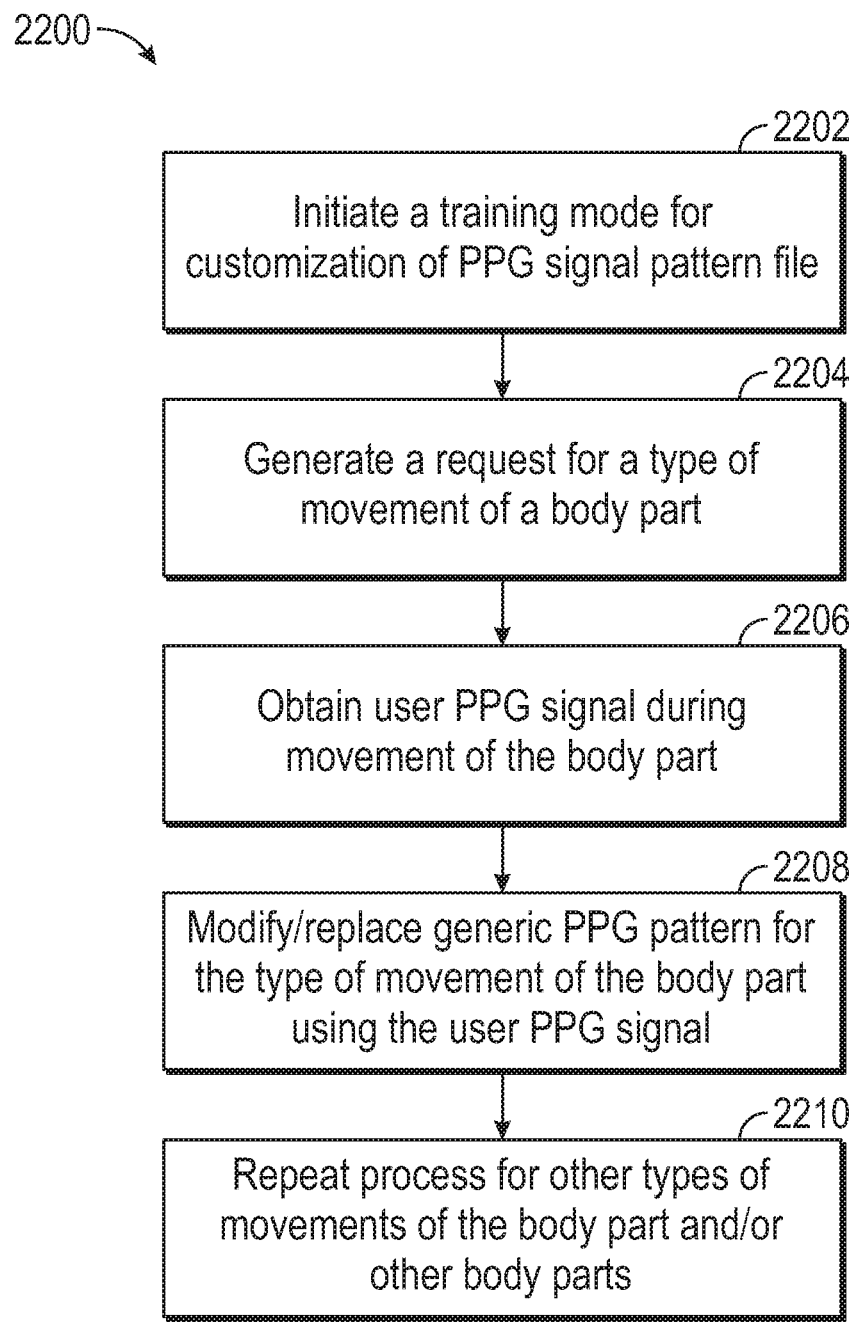
FIG. 22 illustrates a logical flow diagram of an embodiment of a method for a training mode to determine customized PPG signal patterns.

FIG. 22 illustrates a logical flow diagram of an embodiment of a method 2200 for a training mode to determine customized PPG signal patterns. A biosensor 100 may initiate a training mode for customization of the PPG signal patterns at 2202. The training mode may be initiated upon a first use or upon request of a user. During the training mode, a GUI of the biosensor or user device in communication with the biosensor requests movement of a particular body part at 2204. The request may also include a type of movement, such as move right finger up and down or rotate hand to the right. The biosensor 100 obtains PPG signals during the requested movement of the body part at 2206. The PPG signal pattern of the user is stored in the PPG signal pattern file and associated with the request movement. The PPG signal pattern of the user may be used to modify or replace the generic PPG signal pattern at 2208. The training mode continues for other types of movements of the same body part and/or for movements of other body parts at 2210.

In another embodiment, the training of the biosensor 100 may be performed using a 3-D motion capture or video analysis system. The 3-D motion capture or video analysis system obtains motion data while the biosensor 100 monitors PPG signals. The motion artifacts in the PPG signals at one or more wavelengths are mapped to the motion data to generate predetermined PPG signal patterns. The motion data may be input with the PPG signals into a neural network processing device to generate a learning vector as well.

Figure 23:
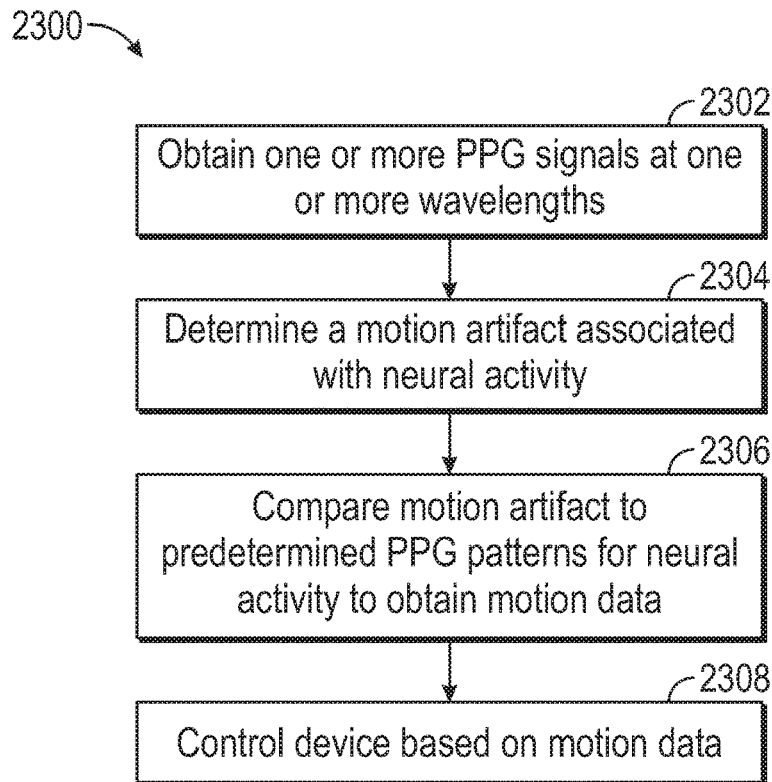
FIG. 23 illustrates a logical flow diagram of an embodiment of a method for detecting neural activity using PPG signals.

FIG. 23 illustrates a logical flow diagram of an embodiment of a method 2300 for detecting neural activity using PPG signals. Electrical activity is produced to stimulate and activate muscles. However, in some instances, these muscles are not operable or non-existent as in an amputated limb. The electrical stimulation of the muscle may occur with little to no movement. In another embodiment, a person may train the biosensor 100 to detect neural stimulation or activity with little to no movement of a body part. Even when little to no movement occurs, the electrical activity generates a change in potential of muscles and/or vasodilation of surrounding vessels and thus changes the optical properties of the underlying tissue. PPG signals may then detect this change in the optical properties.

PPG signals are obtained at one or more wavelengths at 2302. Though little or no movement occurs, the PPG signals reflect neural activity in underlying tissue. The neural activity is identified in the PPG and data associated with the neural activity is obtained at 2306. For example, the neural activity may be associated with an input command or type of movement of a body part. A device may be controlled based on the data associated with the neural activity at 2308. In one embodiment, the biosensor 100 is used to control a prosthetic limb using detection of neural activity. In another embodiment, the biosensor 100 is used to control a cursor or keyboard without movement based on detected neural activity.

Figure 24:
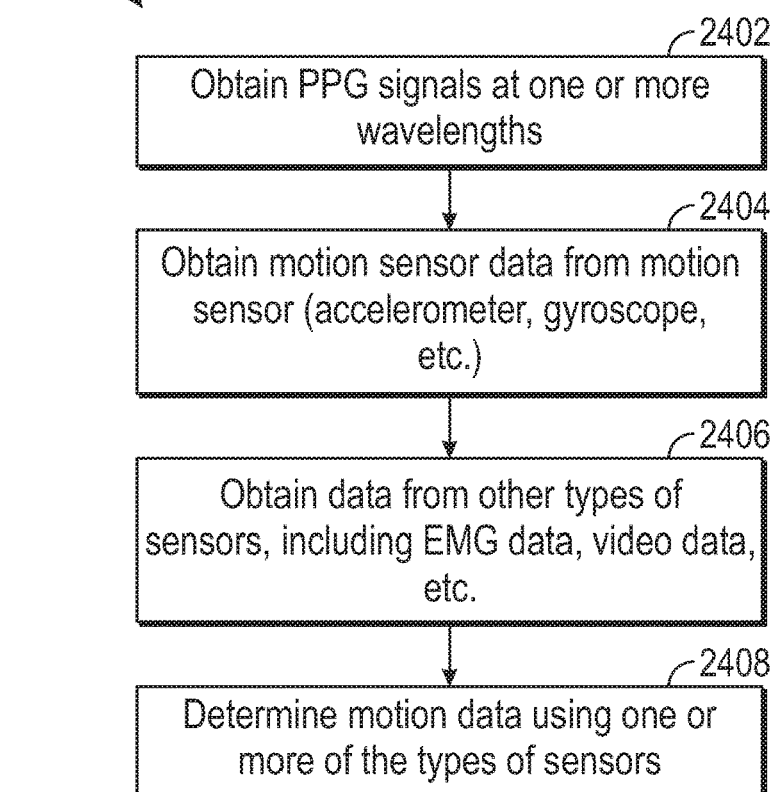
FIG. 24 illustrates a logical flow diagram of an embodiment of a method for detecting neural activity or movement of a body part using one or more types of sensors.

FIG. 24 illustrates a logical flow diagram of an embodiment of a method 2400 for detecting neural activity or movement of a body part using one or more types of sensors. PPG signals are obtained at one or more wavelengths at 2402. Motion sensor data from the motion sensor, such as an accelerometer or gyroscope, is obtained at 2404. The motion sensors may provide motion data relating to movement of the biosensor in three-dimensional (3D) space in relation to a portion of the user or to a control plane.

Data from other types of sensors for detecting motion may also be obtained at 2406. For example, an electromyography (EMG) sensor may detect neural activity for activation of muscles at one or more locations on the hand or at other parts of the body. A 3-D motion capture or video analysis system may be used to obtain motion data as well. Data obtained from an electrocardiogram sensor (ECG or EKG) or an electroencephalogram (EEG) sensor may also be used. The data from one or more of the types of sensors may be used to determine motion data at 2408.

Figure 25:
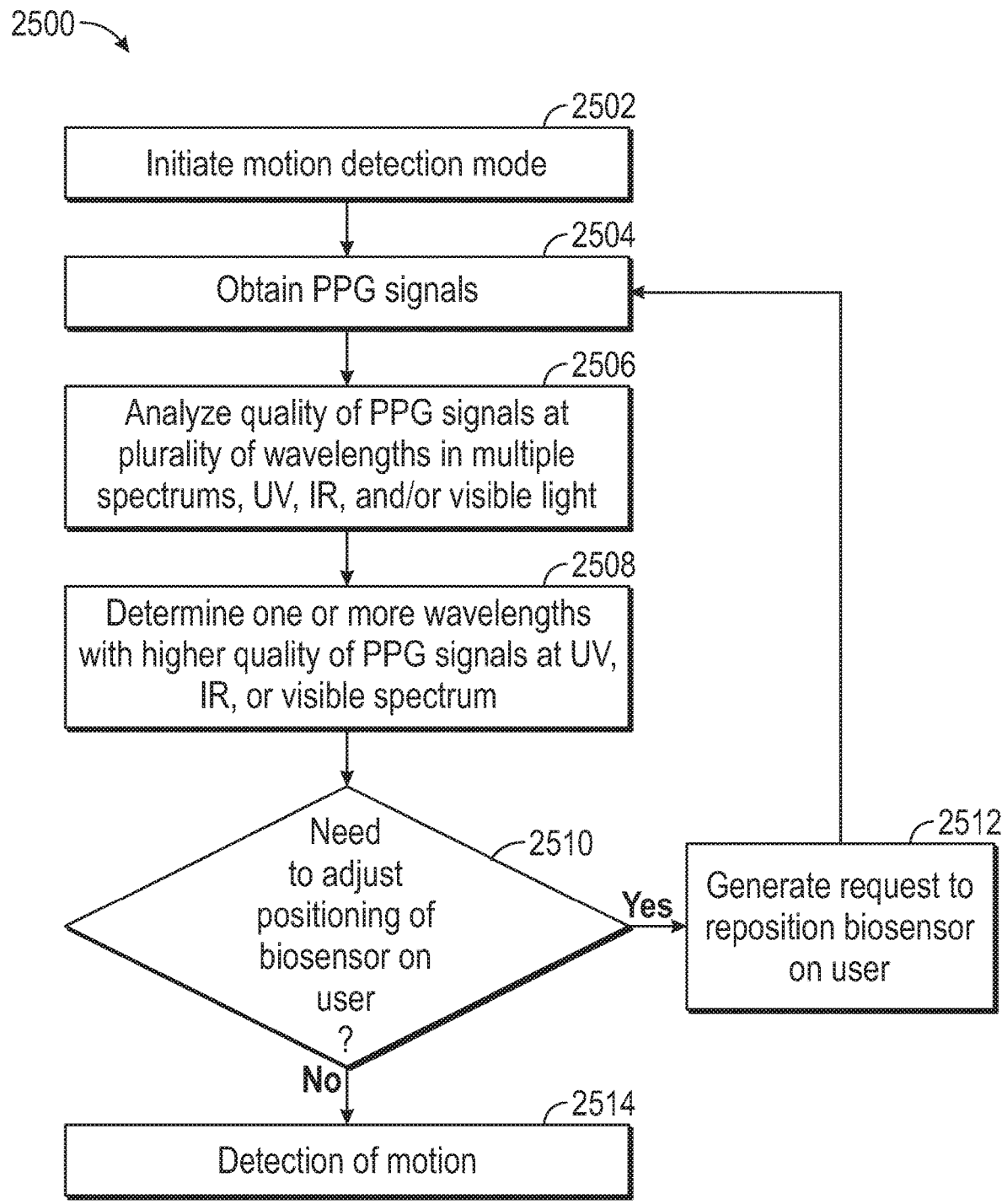
FIG. 25 illustrates a logical flow diagram of an embodiment of a method for positioning of a biosensor.

FIG. 25 illustrates a logical flow diagram of an embodiment of a method 2500 for positioning of a biosensor 100. The biosensor 100 may have different form factors, such as a watch, bracelet, patch, earbud, glasses, finger attachment, etc. In each form factor, the biosensor 100 is preferably positioned to emit light at the skin tissue of a user and detect light reflected from the skin tissue or light transmitted through the skin tissue. When the biosensor 100 is not properly positioned adjacent to skin tissue, the biosensor 100 may not be able to adequately detect the light from the skin. The PPG signals need to be detected with a sufficient quality for processing of the motion artifacts. In an embodiment, the biosensor 100 generates a request to a user to adjust a position of the form factor when the PPG signals have a low quality below a predetermined threshold.

The biosensor 100 initiates motion detection mode at 2502 and obtains PPG signals at 2504. The quality or noise in the PPG signals may be analyzed at one or more wavelengths at 2506. For example, the heart rate signal may be derived using the PPG signals, and the quality of the heart rate signal determined as a test of the quality of the PPG signal. In an embodiment, the quality of the PPG signal may be analyzed at multiple wavelengths in one or more spectrums, in IR, UV or visible spectrums. The quality of the PPG signals may differ depending on the wavelength and underlying tissue characteristics. At a same input power, light at higher wavelengths (IR light) penetrates vascular tissue deeper than light at lower wavelengths (UV light). The optical properties of the tissue are affected by many factors, including but not limited to, skin-tone, tissue hydration, and tissue chemistry. In a sensor configuration where the light from the light source is backscattered to a sensor on the same surface, the optical signal at the sensor includes a sum of all light backscattered that makes it to the focal surface after interacting with the tissue. With the optical power being the same across all wavelengths, some of the light backscattered from the IR light penetrates deeper into the tissue than the UV light does. This means that the different wavelengths of light probe different depths of tissue. Thus, depending on the type of vascular tissue and depth of the vessels, the IR light, visible light or UV light may result in a higher quality PPG signal.

The biosensor 100 may determine the one or more spectrums of light resulting in higher quality PPG signals, and the one or more wavelengths in the spectrums of light with higher quality PPG signals at 2508. The biosensor 100 may then utilize the determined one or more wavelengths in the spectrums with higher quality to obtain the PPG signals.

If the wavelengths fail to meet a predetermined threshold of quality (such as a signal to noise ratio) or the biosensor 100 may not reliably detect a heart rate in the PPG signals, the biosensor 100 may determine that the position of the biosensor 100 needs to be adjusted at 2510. For example, when the PPG signal at one or more wavelengths falls below a predetermined quality, the biosensor 100 may generate a request or indication to reposition the biosensor 100 on the user at 2512. The indication or request may simply be an LED that is red or green depending on the quality of the PPG signal. A sound may alert the user to reposition the biosensor. The biosensor 100 continues to monitor the PPG signal and indicate to reposition the biosensor 100 until the quality is sufficient to obtain motion data. The biosensor 100 then continues to obtain PPG signals and detect motion data at 2514.

FIG. 26-29 illustrate schematic block diagram of various form factors of the biosensor 100. The biosensor 100 may be integrated in a watch, patch, button, band, earpiece, earphones, ankle bracelet or other devices adjacent to skin of a patient.

Figure 26:
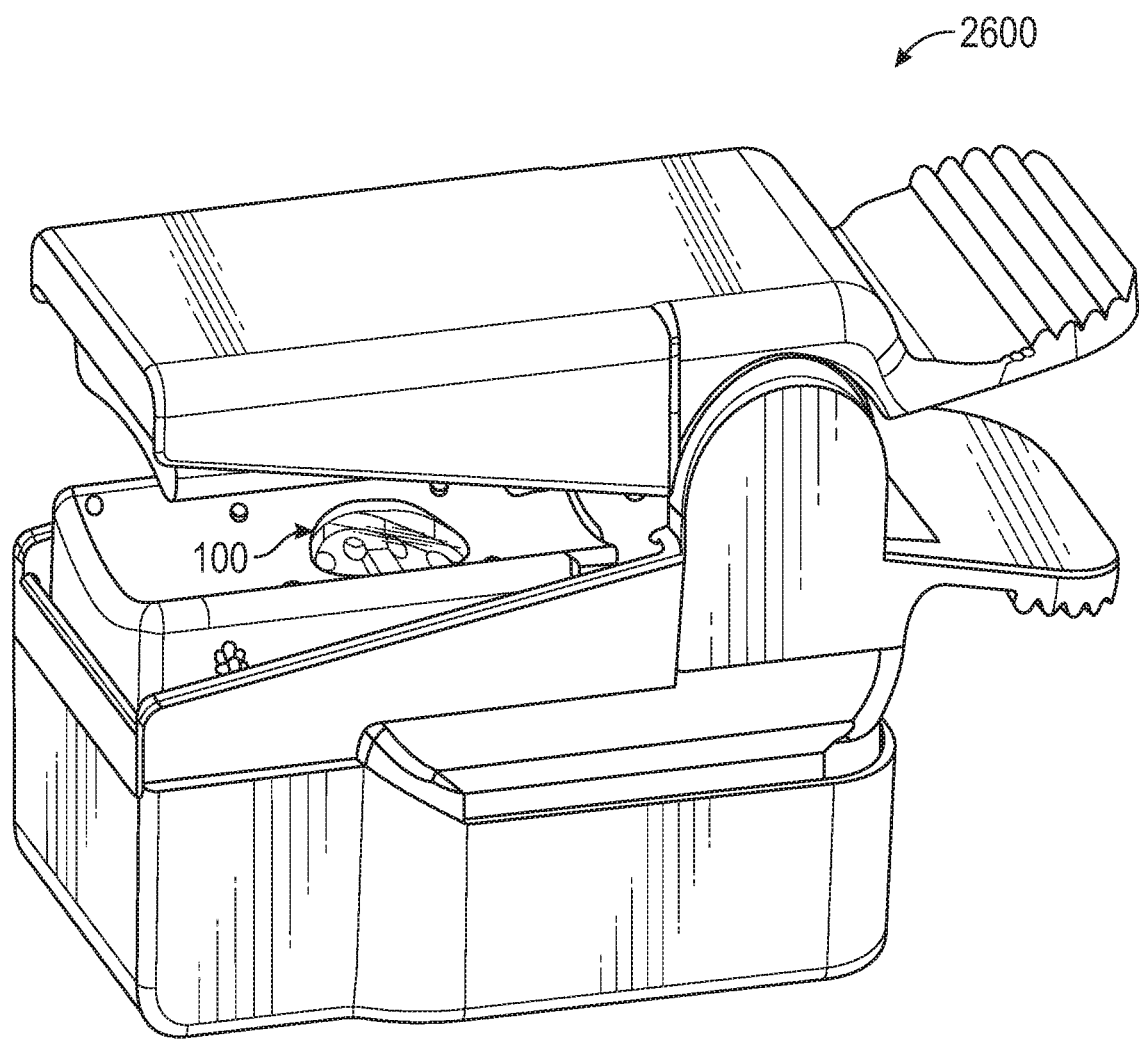
FIG. 26 illustrates a schematic block diagram of an embodiment of the biosensor integrated in a finger attachment.

FIG. 26 illustrates a schematic block diagram of an embodiment of the biosensor 100 integrated in a finger attachment 2600. The biosensor 100 is positioned such that the emitting light sources and photodetectors are adjacent to a fingertip positioned in the finger attachment. The finger attachment 2600 may also include one or more types of displays and/or one or more other types of user interfaces.

Figure 27A:
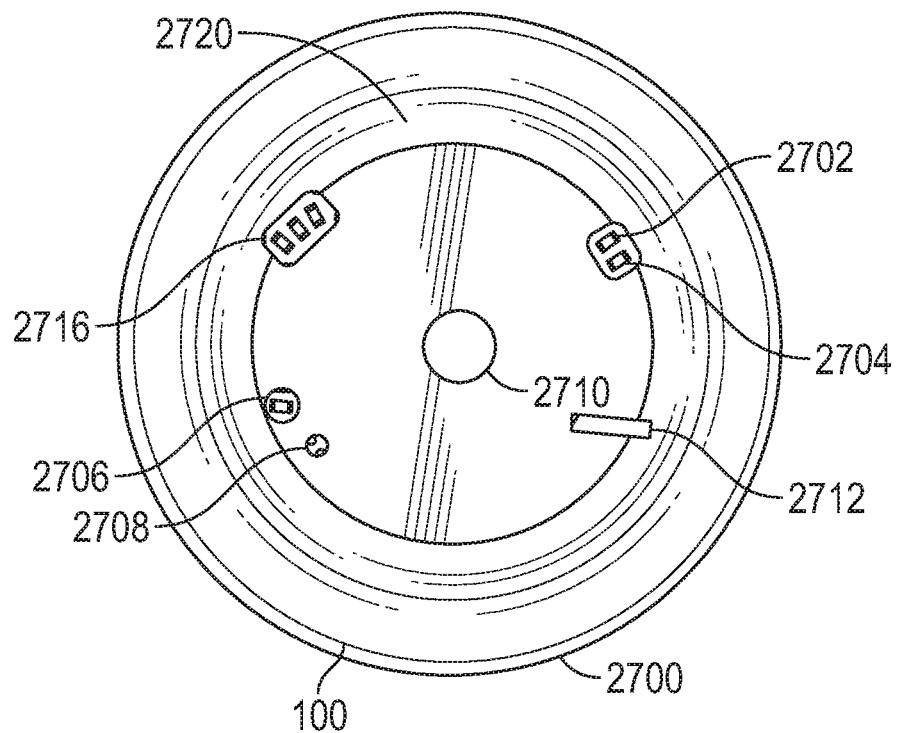
FIG. 27A illustrates a perspective view of a first side of another embodiment of the biosensor integrated in a patch.

FIG. 27A illustrates a perspective view of a first side of another embodiment of the biosensor 100 integrated in a patch 2700. The first side 2720 of the patch 2700 is configured to face upwards away from skin tissue of a patient. A user interface circuit 2710 is configured to provide a user with control to select one or more modes of operation. In one embodiment, the user interface circuit 2710 may include a push button or dial or touchscreen. A mode indicator 2704 is configured to indicate the mode of operation of the patch 2700. In an embodiment, the mode indicator 2704 may include one or more LEDs that illuminate to illustrate one or more modes of operation.

The patch 2700 may also include a position indicator 2716 that indicates that the biosensor 100 needs to be repositioned for improved detection of PPG signals. The patch 2700 may also include a health alert indicator 2706 to provide a warning or health alert. The health alert indicator 2706 in this embodiment includes a first LED that may illuminate to provide a status or indication of a health condition. For example, the LED may illuminate if a high heart rate, temperature or respiration rate above safe thresholds are detected. The patch 2700 may in addition to or alternatively include an audible indicator 2708 configured to provide audible or verbal indications or alerts. The visible indicator may also include a digital display.

The patch 2700 may also include a heart rate (bpm) indicator 2702. The heart rate indicator 2702 may include an LED that blinks or changes color upon detection of a heartbeat. A person may thus count a number of heartbeats using the flashing LED. Though LEDs are described herein to provide various types of information and alerts, the patch 2700 may implement other types of user interfaces, such as a display or touchscreen or a verbal interface, to provide such alerts and information. The patch 2700 may also include a transceiver 2712, wired or wireless, to communicate with another device. For example, the transceiver 2712 may include a USB port for a wired communication or an RFID or Bluetooth wireless transceiver. The transceiver 2712 may communicate configuration information to the patch 2700 or communicate motion data or commands from the patch 2700 to a user device or other type of device.

Figure 27B:
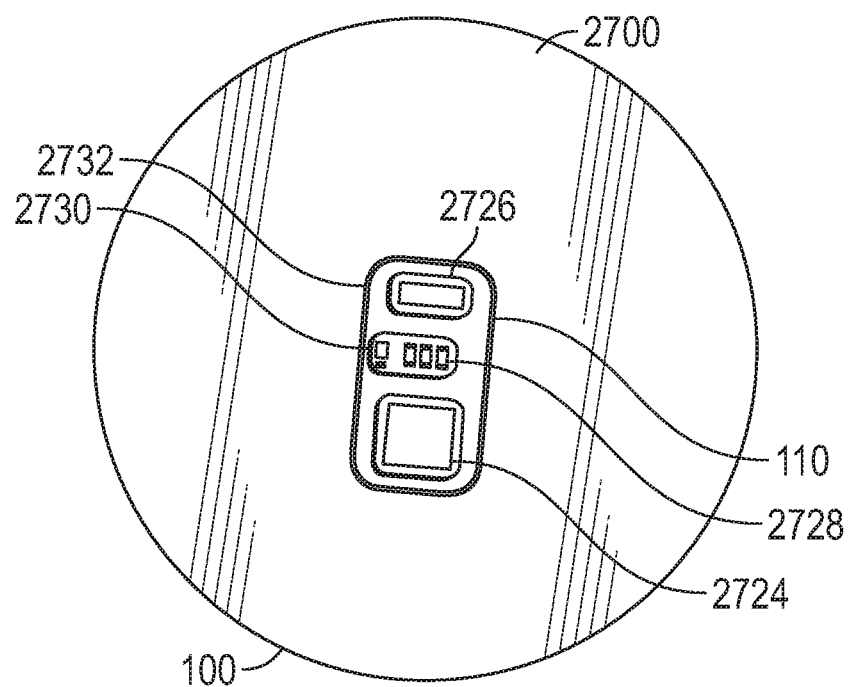
FIG. 27B illustrates a perspective view of a second side of an embodiment of the biosensor integrated in the patch.

FIG. 27B illustrates a perspective view of a second side of an embodiment of the biosensor 100 integrated in the patch 2700. The second side of the patch 2700 is configured to face towards skin tissue of a user. The PPG 110 includes at least a first photodiode 2724 and may also include a second photodiode 2726. The photodiodes 2724, 2726 are positioned on opposite sides of a plurality of LEDs 2728. The LEDs 2728 are configured to emit light at a plurality of wavelengths. For example, a first wavelength is in a UV range of 380-410 nm and is preferably 390 nm or 395 nm. A second wavelength is in an IR range, such as approximately 660 nm, and a third wavelength is an IR range, such as approximately 940 nm. Additional or alternative LEDs may be included that have different wavelengths. The patch 2700 may also include a temperature sensor 2730 configured to detect a skin temperature of the patent. A gasket 2732 is implemented to hold the PPG circuit 110 in position.

Figure 28A:
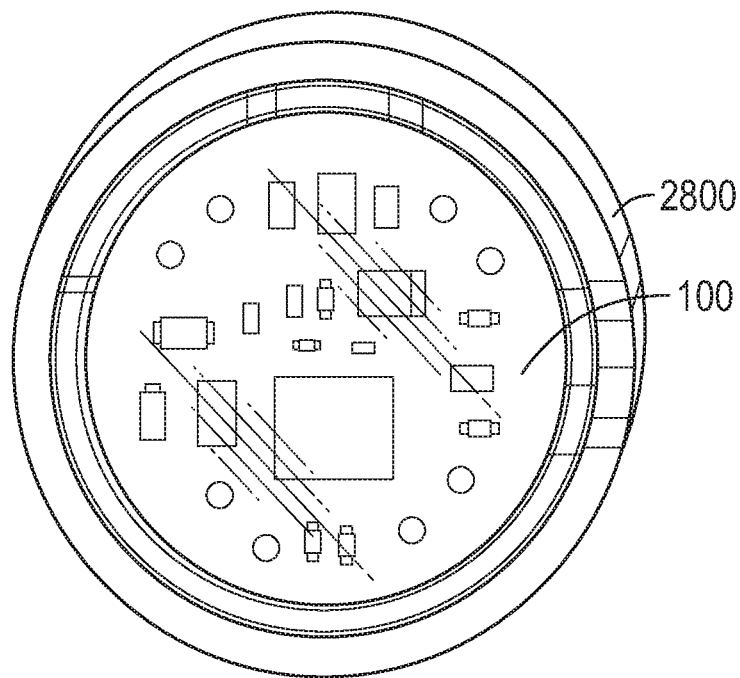
FIG. 28A illustrates a perspective view of an embodiment of the biosensor configured in an earpiece.
Figure 28B:
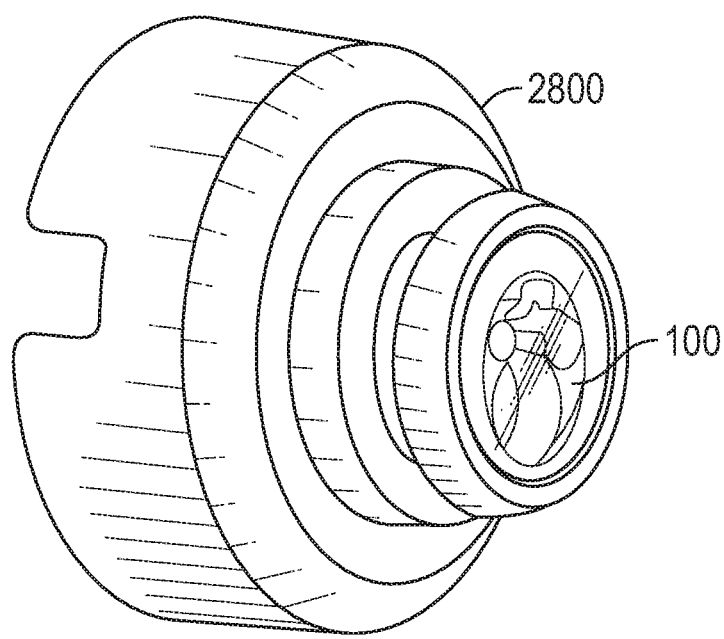
FIG. 28B illustrates another perspective view of the biosensor integrated in the earpiece.

FIG. 28A illustrates a perspective view of an embodiment of the biosensor 100 configured in an earpiece 2800. The earpiece 2800 is configured to fit within an ear canal of a user. FIG. 28B illustrates another perspective view of the biosensor 100 integrated in the earpiece 2800. The earpiece 2800 may be used to detect movement of facial muscles using PPG signals. The motion artifacts in the detected PPG signals are correlated with predetermined PPG signal patterns associated with facial movements or facial expressions. The earpiece 2800 may thus detect facial expressions or movements using PPG signals.

FIG. 29A and FIG. 29B illustrate a perspective view of another embodiment of a biosensor 100 integrated in a wristband 2900. FIG. 29A illustrates a bottom portion 2902 of the wristband 2900 with an integrated biosensor 100. The light sources and photodetector of the biosensor 100 is positioned adjacent to skin tissue of the user. In this embodiment, the biosensor 100 is implemented with an adjustable band 2908. The adjustable band 2900 may be configured to fit around a wrist, arm, leg, ankle, etc. The bottom portion 2902 of the biosensor 100 includes at least one opening for the PPG circuit 110 to emit light directed to the skin tissue and detect light reflected from the skin tissue of a user. A USB or other port 2906 may be implemented to transmit data to and from the biosensor 100. The biosensor 100 may also include a wireless transceiver.

FIG. 29B illustrates a perspective view of a top portion 2904 of the wristband 2900 including the biosensor 100. Though not shown, the top portion of the biosensor 100 may include a display or other user interface.

FIG. 29C illustrates the wristband 2900 positioned on a wrist of a user. The bottom portion 2902 is preferably positioned on a top part of the wrist of the user since the upper portion of the wrist includes a greater density of vessels near the surface of the underlying tissue. In an embodiment, the photodetector is more centrally located on the bottom portion 2902 with the light sources or LEDs arranged in positions around the photodiode. The spatially distributed LEDs on the bottom portion provide better detection of a range of motion of the hand. The LEDs do not need to be placed in specific positions, such as over tendons or muscles or nerves. A plurality of LEDs dispersed across the bottom portion 2902 of the biosensor 100 may detect movement of the hand and all the fingers. The PPG signals detected by a plurality of the LEDs may each be considered to determine a motion vector of a body part.

In an embodiment, an existing device, such as an activity monitoring device, a smart phone with camera, or a smart watch, may be implemented as the biosensor 100. These existing devices may already include an LED and photodetector and may be configured to obtain PPG signals from light reflected from the skin. The processing of the PPG signals may be performed by the existing devices (e.g., with new downloaded software upgrades) or the processing may be performed by a smart phone, laptop, central server or other secondary device in communication with the existing devices. The secondary devices may then communicate the results back to the existing device.

Figure 30:
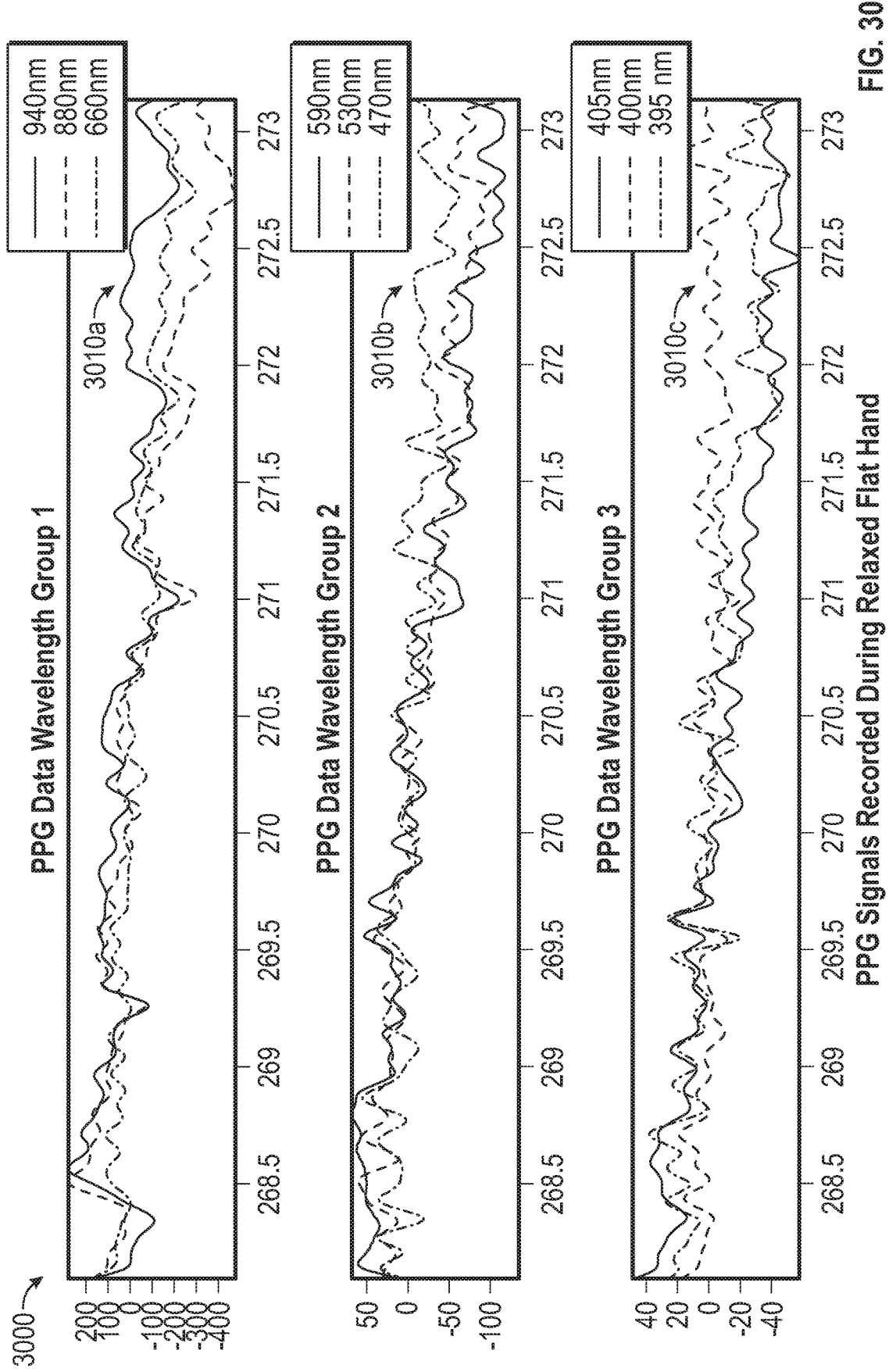
FIG. 30 illustrates a schematic diagram of a graph of spectral responses obtained using an embodiment of the biosensor while the hand is relaxed.

FIG. 30 illustrates a schematic diagram of a graph 3000 of spectral responses obtained using an embodiment of the biosensor 100 while the hand is relaxed. The biosensor 100 is positioned on the wrist of the right hand of the user as shown in FIG. 29C. The hand is flat, and fingers relaxed.

Again, in this example, the biosensor 100 obtained a PPG signal around a wavelength at 940 nm, a wavelength at 880 nm and a wavelength at 660 nm as shown in the PPG Signals for Wavelength Group 3010a. The biosensor 100 also obtained the spectral response for a wavelength at 590 nm, a wavelength at 530 nm and a wavelength at 470 nm as shown in the PPG Signals for Wavelength Group 3010b. The biosensor 100 further obtained the spectral response for a wavelength at 405 nm, a wavelength at 400 nm and a wavelength at 395 nm as shown in the PPG Signals for Wavelength Group 3010c.

The PPG signals at the plurality of wavelengths include a response to the pressure pulse wave through the vessels from the cardiac cycle. The cardiac cycle is more pronounced in the PPG signals for Wavelength Group 3010c. These wavelengths are in the UV range. Depending on placement of the biosensor 100, the wavelengths in one or more spectrums may be more sensitive to the heart rate or to motion artifacts. There is little to no indication of movement of the hand or fingers in the PPG signals.

Figure 31:
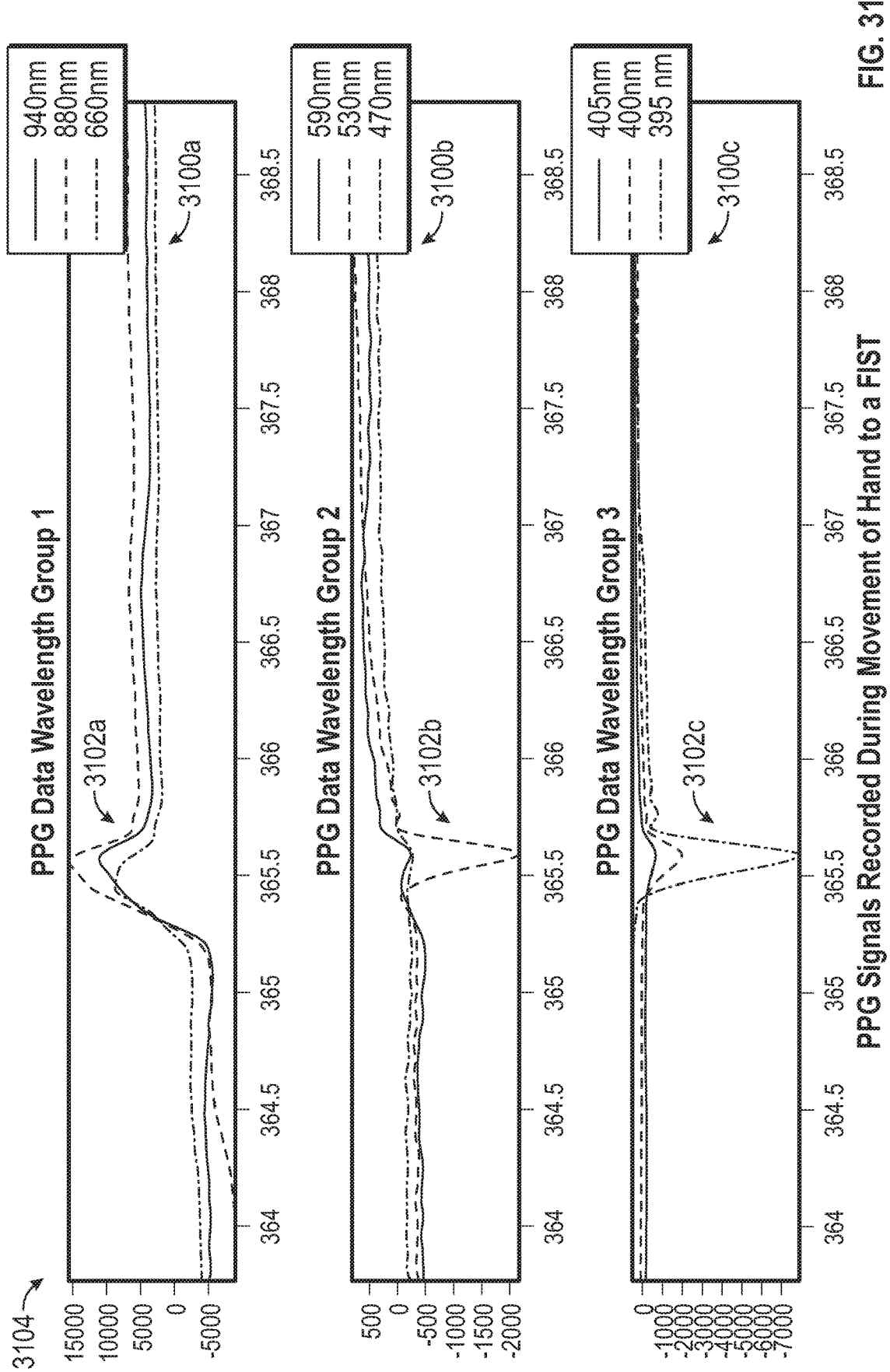
FIG. 31 illustrates a schematic diagram of a graph of spectral responses obtained using an embodiment of the biosensor during movement of the hand into a fist.

FIG. 31 illustrates a schematic diagram of a graph 3104 of spectral responses obtained using an embodiment of the biosensor 100 during movement of the hand into a fist. The biosensor 100 is still positioned on the wrist of the right hand of the user and has not been repositioned from FIG. 30. During this measurement period, the user moves the right hand from a relatively flat position into a fist.

Again, in this example, the biosensor 100 obtained a PPG signal around a wavelength at 940 nm, a wavelength at 880 nm and a wavelength at 660 nm as shown in the PPG Signals for Wavelength Group 3100a. The biosensor 100 also obtained the spectral response for a wavelength at 590 nm, a wavelength at 530 nm and a wavelength at 470 nm as shown in the PPG Signals for Wavelength Group 3100b. The biosensor 100 further obtained the spectral response for a wavelength at 405 nm, a wavelength at 400 nm and a wavelength at 395 nm as shown in the PPG Signals for Wavelength Group 3100c.

The PPG signals at the plurality of wavelengths include a response to the pressure pulse wave through the vessels from the cardiac cycle. In addition, at approximately the time of 365.5 seconds, there is an indication of movement of the hand in the PPG signals at 3102a, 3102b and 3102c. The PPG signals at each wavelength have a somewhat different or unique pattern in response to the movement of the hand. These patterns 3102a-c in the PPG signal are not present in the PPG signals with little to no movement shown in FIG. 30. The unique PPG signal pattern at each wavelength may be used to identify the movement of the hand to a fist in later obtained waveforms.

Figure 32:
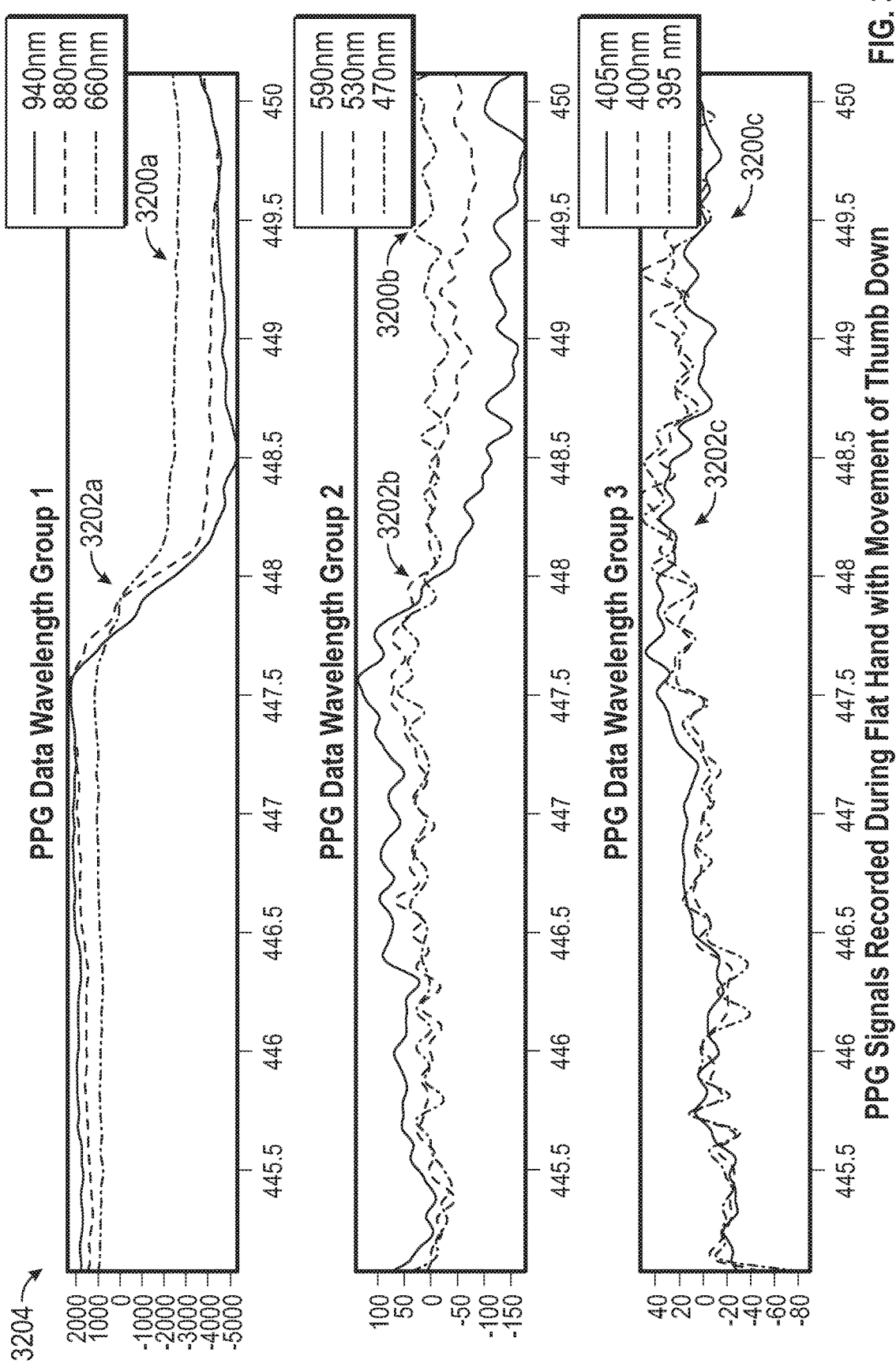
FIG. 32 illustrates a schematic diagram of a graph of spectral responses obtained using an embodiment of the biosensor during a downward thumb movement.

FIG. 32 illustrates a schematic diagram of a graph 3204 of spectral responses obtained using an embodiment of the biosensor 100 during a downward thumb movement. The biosensor 100 is still positioned on the wrist of the right hand of the user and has not been repositioned from FIG. 30. During this measurement period, the user holds the right hand relatively relaxed and level while moving the thumb downward.

Again, in this example, the biosensor 100 obtained a PPG signal around a wavelength at 940 nm, a wavelength at 880 nm and a wavelength at 660 nm as shown in the PPG Signals for Wavelength Group 3200a. The biosensor 100 also obtained the spectral response for a wavelength at 590 nm, a wavelength at 530 nm and a wavelength at 470 nm as shown in the PPG Signals for Wavelength Group 3200b. The biosensor 100 further obtained the spectral response for a wavelength at 405 nm, a wavelength at 400 nm and a wavelength at 395 nm as shown in the PPG Signals for Wavelength Group 3200c.

The PPG signals at the plurality of wavelengths include a response to the pressure pulse wave through the vessels from the cardiac cycle. In addition, at approximately the time of 447.5 seconds, there is an indication of movement of the hand in the PPG signals at 3202a, 3202b and 3202c. The PPG signals at each wavelength have a somewhat different or unique pattern in response to the movement of the thumb. These patterns 3202a-c in the PPG signal are not present in the PPG signals with little to no movement shown in FIG. 30. The unique PPG signal pattern at each wavelength may be used to identify the downward movement of the thumb.

Figure 33:
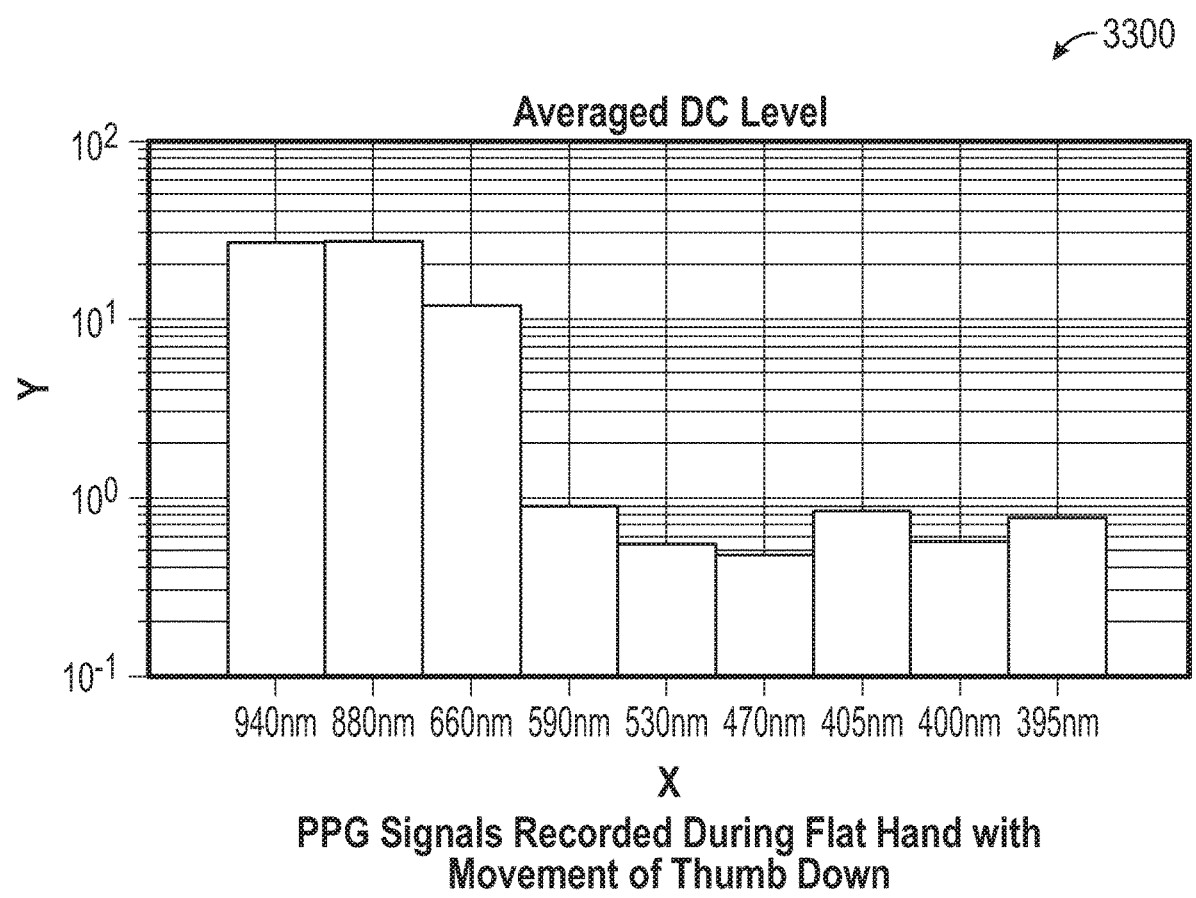
FIG. 33 illustrates a schematic diagram of a graph of data generated from the spectral responses obtained using an embodiment of the biosensor during the downward thumb movement.

FIG. 33 illustrates a schematic diagram of a graph 3300 of data generated from the spectral responses obtained using an embodiment of the biosensor 100 during the downward thumb movement shown in FIG. 32. In graph 3302, the average DC Level is shown for each of the wavelengths. The average DC level during motion artifacts are indicative of a force applied to a movement. A maximum amplitude of the motion artifact may also be used as an indication of force applied to a movement.

Figure 34:
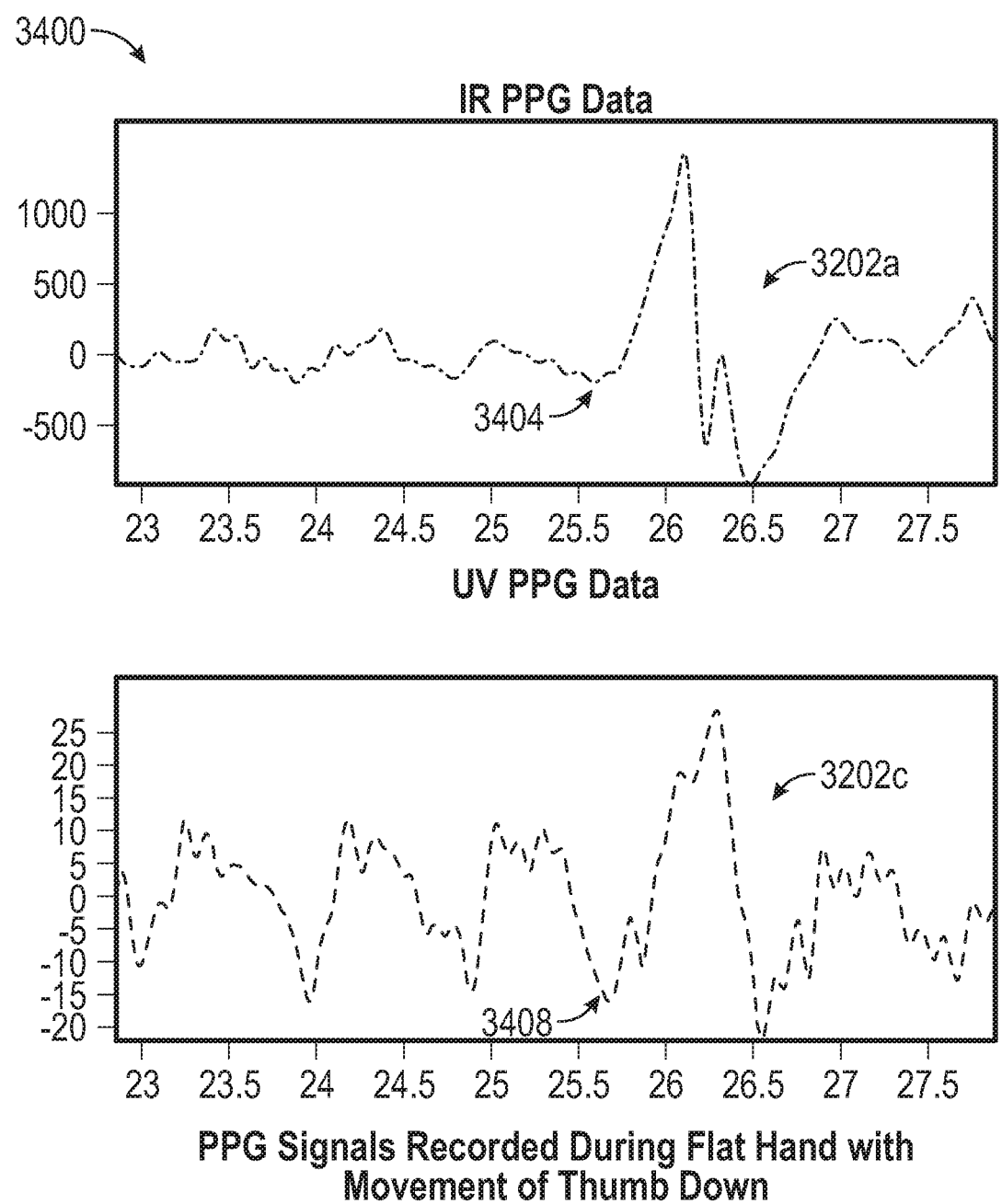
FIG. 34 illustrates a schematic diagram of a graph of additional data generated from the spectral responses obtained using an embodiment of the biosensor during the downward thumb movement.

FIG. 34 illustrates a schematic diagram of a graph 3400 of additional data generated from the spectral responses obtained using an embodiment of the biosensor 100 during the downward thumb movement shown in FIG. 32. In graph 3402, the motion artifact 3202a in the IR range of 940 nm is shown while the motion artifact 3202c in the UV range of 395 nm is shown. The cardiac cycle is more prevalent in the UV range, and the motion artifact 3202c is reflected in the PPG signal over the cardiac cycle. The depth of penetration of the light into tissue depends on the spectrum. Thus, the wavelengths in one or more spectrums may be more sensitive to the cardiac cycle or to the movement depending on the position of the biosensor 100. The motion artifacts at different wavelengths may thus be different and have unique PPG signal patterns for a same movement. The biosensor 100 may thus identify a motion artifact in multiple wavelengths occurring at a similar time. The motion artifacts at each wavelength may be compared to predetermined PPG signal patterns for their respective wavelength to determine motion data.

Neural activity or stimulation generates a muscular reaction during a movement of a body part. This neural activity is reflected in the PPG signal, especially at initiation of the motion artifact. For example, the motion artifact 3202a includes an initial change in the PPG signal 3404 in response to neural activity. The motion artifact 3202c also includes an initial change in the PPG signal 3408 in response to neural activity.

Figure 35:
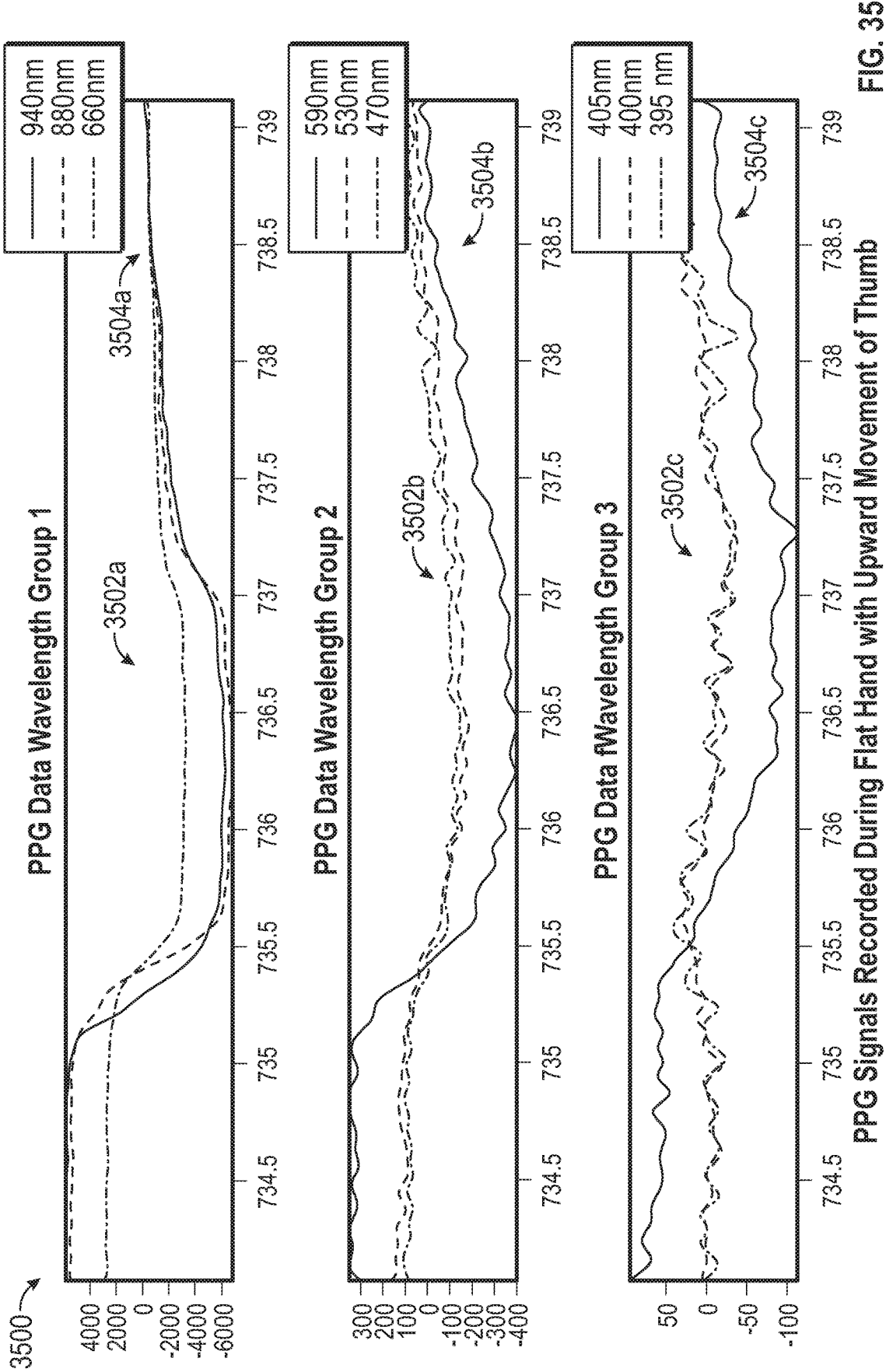
FIG. 35 illustrates a schematic diagram of a graph of spectral responses obtained using an embodiment of the biosensor during an upward thumb movement.

FIG. 35 illustrates a schematic diagram of a graph 3500 of spectral responses obtained using an embodiment of the biosensor 100 during an upward thumb movement. The biosensor 100 is still positioned on the wrist of the right hand of the user and has not been repositioned from FIG. 30. During this measurement period, the right hand is held relatively flat while the thumb is moved upward.

Again, in this example, the biosensor 100 obtained a PPG signal around a wavelength at 940 nm, a wavelength at 880 nm and a wavelength at 660 nm as shown in the PPG Signals for Wavelength Group 3504a. The biosensor 100 also obtained the spectral response for a wavelength at 590 nm, a wavelength at 530 nm and a wavelength at 470 nm as shown in the PPG Signals for Wavelength Group 3504b. The biosensor 100 further obtained the spectral response for a wavelength at 405 nm, a wavelength at 400 nm and a wavelength at 395 nm as shown in the PPG Signals for Wavelength Group 3504c.

The PPG signals at the plurality of wavelengths include a response to the pressure pulse wave through the vessels from the cardiac cycle. In addition, at approximately the time of 735.5 seconds, there is an indication of movement of the hand in the PPG signals at 3502a, 3502b and 3502c. The PPG signals at each wavelength have a somewhat different or unique pattern in response to the movement of the thumb. These patterns 3502a-c in the PPG signal are not present in the PPG signals with little to no movement shown in FIG.

30. The unique PPG signal pattern at each wavelength may be used to identify the upward movement of the thumb.

Figure 36:
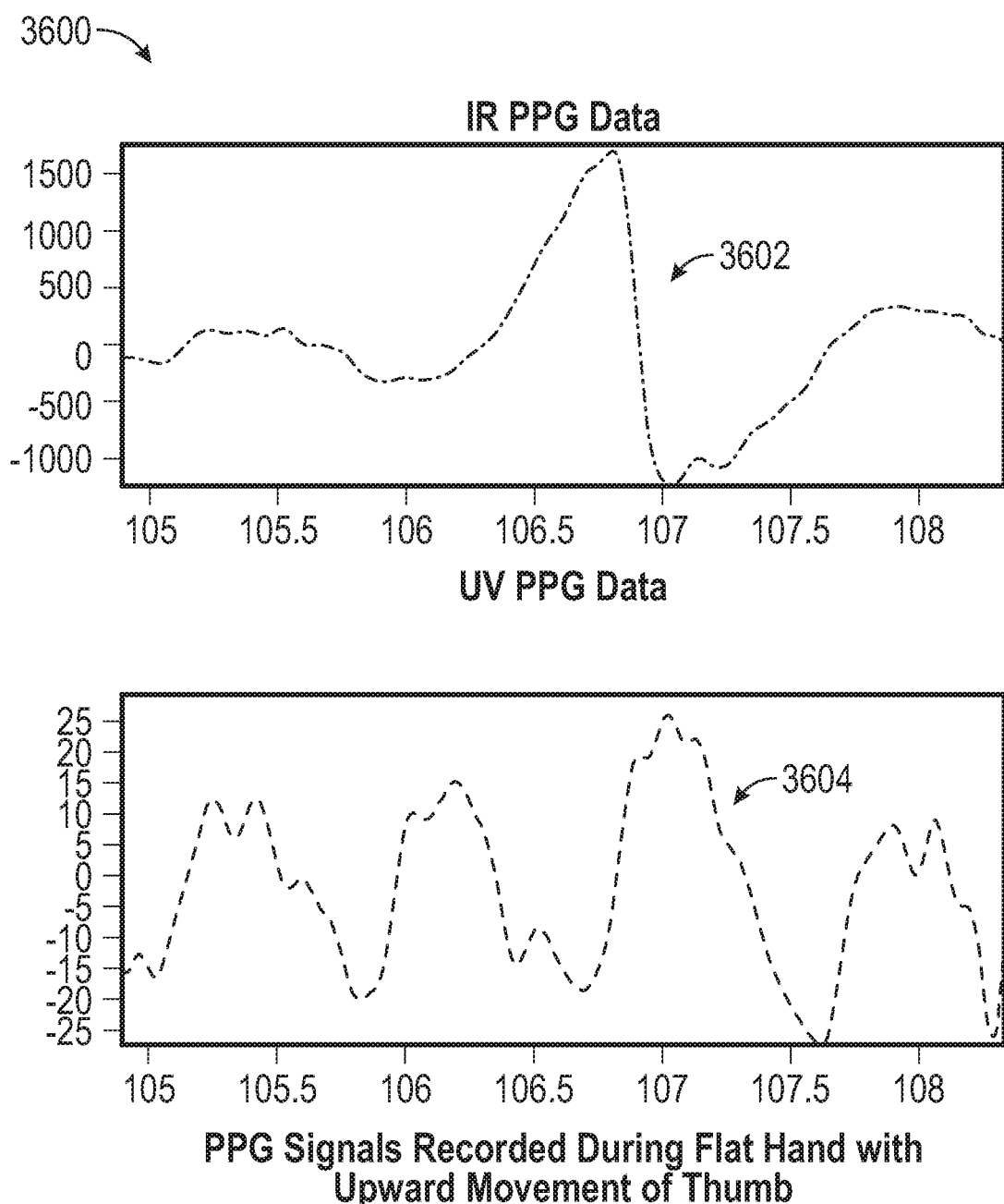
FIG. 36 illustrates a schematic diagram of a graph of additional data generated from the spectral responses obtained using an embodiment of the biosensor during the upward thumb movement.

FIG. 36 illustrates a schematic diagram of a graph 3600 of additional data generated from the spectral responses obtained using an embodiment of the biosensor 100 during the upward thumb movement shown in FIG. 35. The motion artifact 3502a in the IR range of 940 nm is shown in the top graph 3602 while the motion artifact 3502c in the UV range of 395 nm is shown in the bottom graph 3604. The cardiac cycle is more prevalent in the UV range, however the motion artifact 3502c is still reflected in the PPG signal over the cardiac cycle. The depth of penetration of the light into tissue depends on the spectrum, such as UV or IR light. Thus, the wavelengths in different spectrums may have different sensitivities to the cardiac cycle or to the movement depending on the position of the biosensor 100. The motion artifacts generated from a same movement may thus be different at different wavelengths and have unique PPG signal patterns. The biosensor 100 may identify motion artifacts in multiple wavelengths occurring at a similar time. The motion artifacts at each wavelength may be compared to predetermined PPG signal patterns for their respective wavelength to determine motion data.

Figure 37:
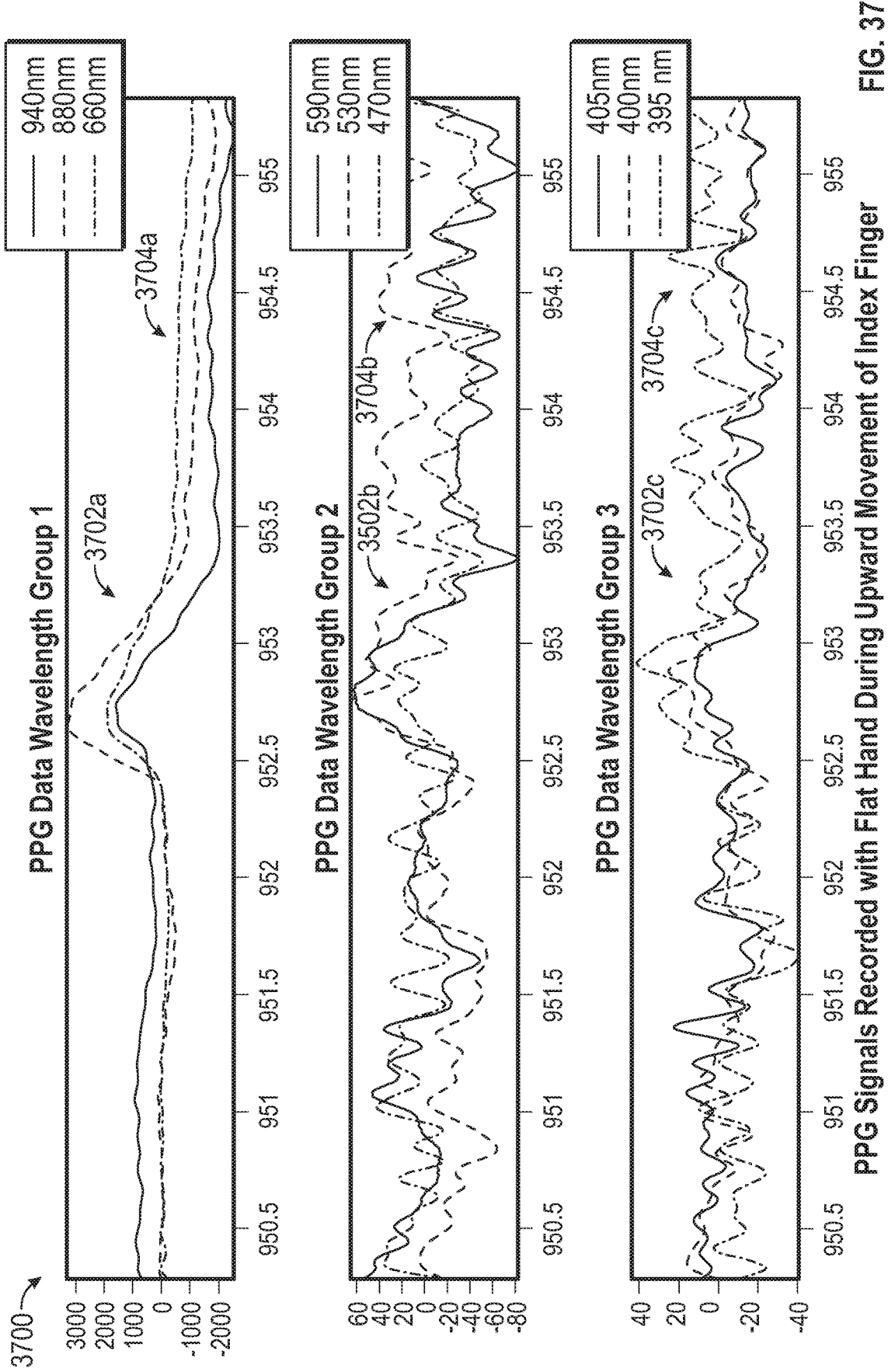
FIG. 37 illustrates a schematic diagram of a graph of spectral responses obtained using an embodiment of the biosensor during an upward movement of the index finger.

FIG. 37 illustrates a schematic diagram of a graph 3700 of spectral responses obtained using an embodiment of the biosensor 100 during an upward movement of the index finger. The biosensor 100 is still positioned on the wrist of the right hand of the user and has not been repositioned from FIG. 30. During this measurement period, the right hand is held flat with an upward movement of the index finger.

Again, in this example, the biosensor 100 obtained a PPG signal around a wavelength at 940 nm, a wavelength at 880 nm and a wavelength at 660 nm as shown in the PPG Signals for Wavelength Group 3704a. The biosensor 100 also obtained the spectral response for a wavelength at 590 nm, a wavelength at 530 nm and a wavelength at 470 nm as shown in the PPG Signals for Wavelength Group 3704b. The biosensor 100 further obtained the spectral response for a wavelength at 405 nm, a wavelength at 400 nm and a wavelength at 395 nm as shown in the PPG Signals for Wavelength Group 3704c.

The PPG signals at the plurality of wavelengths include a response to the pressure pulse wave through the vessels from the cardiac cycle. In addition, at approximately the time of 952.5 seconds, there is an indication of movement of the hand in the PPG signals at 3702a, 3702b and 3702c. The PPG signals at each wavelength have a somewhat different or unique pattern in response to the movement of the index finger. These patterns 3702a-c in the PPG signal are not present in the PPG signals with little to no movement shown in FIG. 30. The unique PPG signal pattern at each wavelength may be used to identify the upward movement of the index finger.

Figure 38:
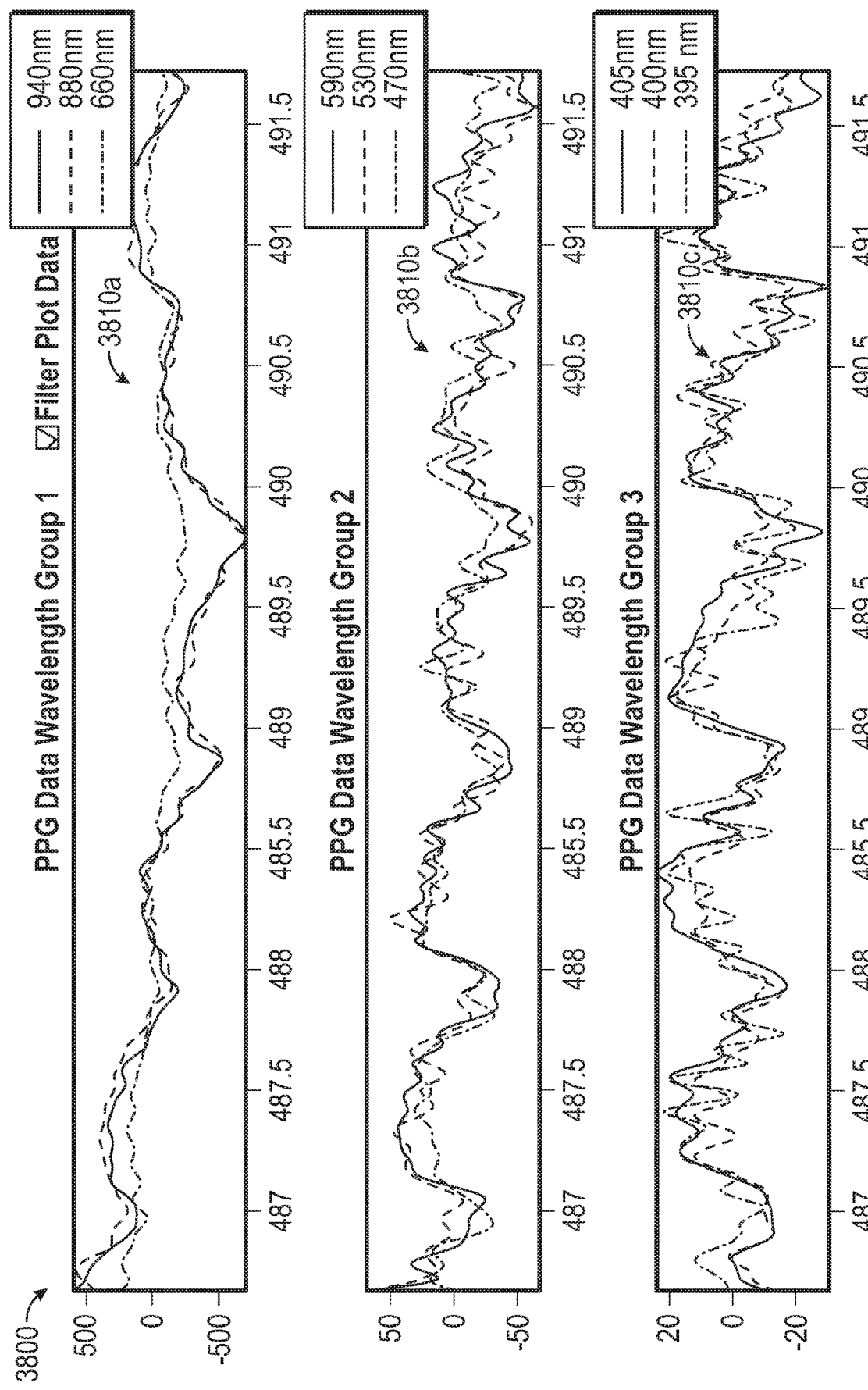
FIG. 38 illustrates a schematic diagram of a graph of spectral responses obtained using an embodiment of the biosensor while the left hand is relaxed.

FIG. 38 illustrates a schematic diagram of a graph 3800 of spectral responses obtained using an embodiment of the biosensor 100 while the left hand is relaxed. The biosensor 100 is positioned on the wrist of the left hand of the user. The hand is relatively level and fingers relaxed.

Again, in this example, the biosensor 100 obtained a PPG signal around a wavelength at 940 nm, a wavelength at 880 nm and a wavelength at 660 nm as shown in the PPG Signals for Wavelength Group 3810a. The biosensor 100 also obtained the spectral response for a wavelength at 590 nm, a wavelength at 530 nm and a wavelength at 470 nm as shown in the PPG Signals for Wavelength Group 3810b. The biosensor 100 further obtained the spectral response for a wavelength at 405 nm, a wavelength at 400 nm and a wavelength at 395 nm as shown in the PPG Signals for Wavelength Group 3810c.

The PPG signals at the plurality of wavelengths include a response to the pressure pulse wave through the vessels in response to the cardiac cycle. The cardiac cycle is more pronounced in the PPG signals for Wavelength Group 3810C. These wavelengths are in the UV range. Depending on placement of the biosensor 100, the wavelengths in one or more spectrums may be more sensitive to the heart rate or to motion artifacts. There is little to no indication of movement of the hand or fingers in the PPG signals.

Figure 39:
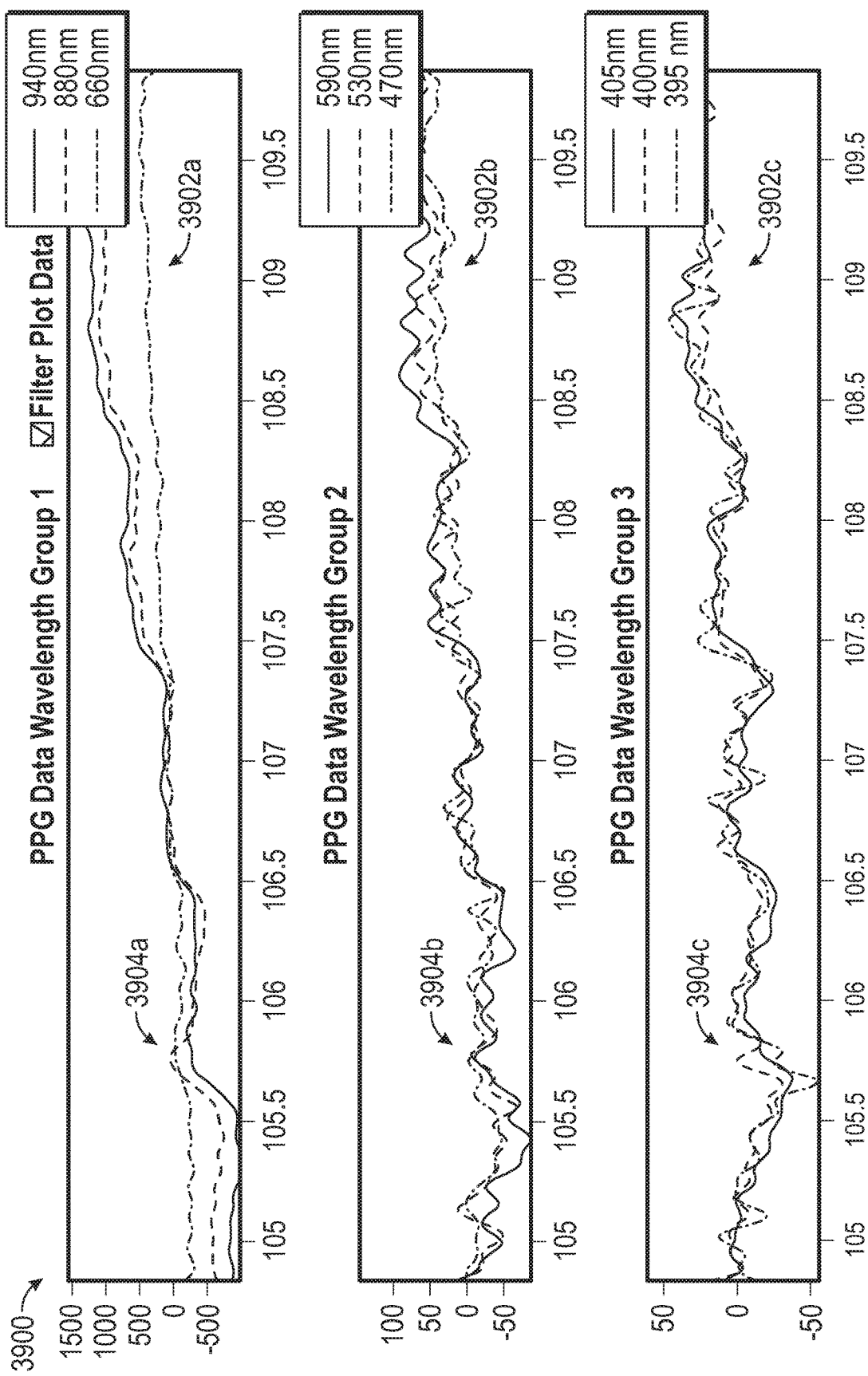
FIG. 39 illustrates a schematic diagram of a graph of spectral responses obtained using an embodiment of the biosensor during a mental intention to move a left index finger but with little to no actual movement.

FIG. 39 illustrates a schematic diagram of a graph 3900 of spectral responses obtained using an embodiment of the biosensor 100 during a mental intention to move a left index finger but with little to no actual movement. The biosensor 100 is still positioned on the wrist of the left hand of the user and has not been repositioned from FIG. 38. The PPG signals at the plurality of wavelengths include a response to the pressure pulse wave through the vessels from the cardiac cycle.

Again, in this example, the biosensor 100 obtained a PPG signal around a wavelength at 940 nm, a wavelength at 880 nm and a wavelength at 660 nm as shown in the PPG Signals for Wavelength Group 3902a. The biosensor 100 also obtained the spectral response for a wavelength at 590 nm, a wavelength at 530 nm and a wavelength at 470 nm as shown in the PPG Signals for Wavelength Group 3902b. The biosensor 100 further obtained the spectral response for a wavelength at 405 nm, a wavelength at 400 nm and a wavelength at 395 nm as shown in the PPG Signals for Wavelength Group 3902c.

During this measurement period, the left hand is still at rest or held relatively level with little to no movement. The user concentrates on mentally activating or initiating an upward movement of the index finger on the left hand but with little to no actual movement. The user may mentally envision moving the index finger or activating muscles in the index finger but with little to no movement. As a result, some neural activity, increased blood flow and vasodilation may occur. The PPG signals include a small fluctuation due to the neural activity and/or vasodilation as seen at 3904a, 3904b and 3904c. The small fluctuation occurs between approximately 105.5 to 106 seconds. The PPG signals at each wavelength have a somewhat different or unique pattern in response to the intended or mental movement of the index finger. These patterns 3904a-c in the PPG signal are not present in the PPG signals with little to no movement shown in FIG. 38. The unique PPG signal pattern at each wavelength may be used to identify the mental intention to move the left index finger with little to no movement. A user may train the biosensor 100 to detect these mental intentions of movement and so control a device with little to no actual movement.

Figure 40:
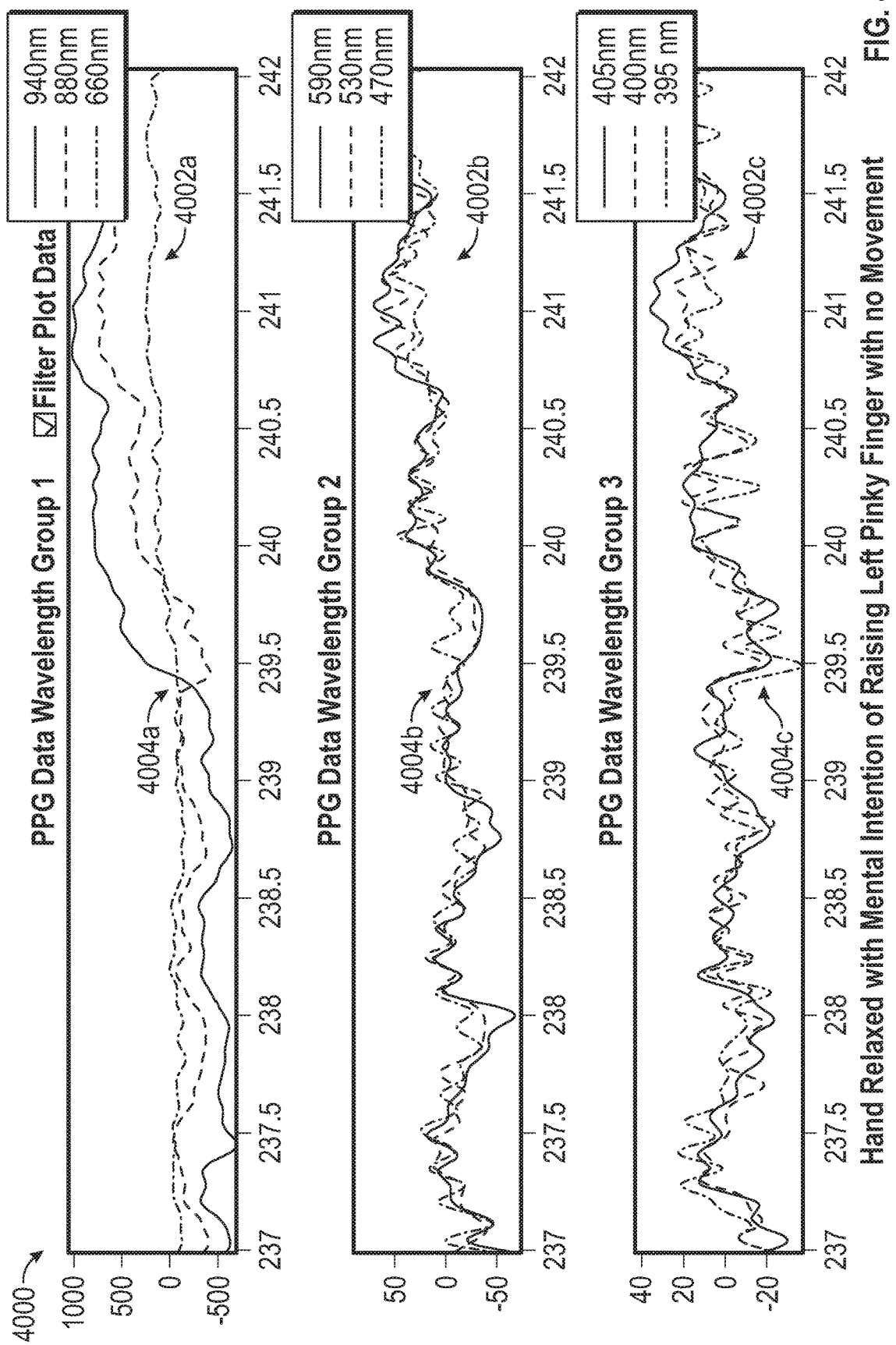
FIG. 40 illustrates a schematic diagram of a graph of spectral responses obtained using an embodiment of the biosensor during a mental intention to move a pinky finger upward but with little to no actual movement.

FIG. 40 illustrates a schematic diagram of a graph 4000 of spectral responses obtained using an embodiment of the biosensor 100 during a mental intention to move a pinky finger upward but with little to no actual movement. The biosensor 100 is still positioned on the wrist of the left hand of the user and has not been repositioned from FIG. 38. The PPG signals at the plurality of wavelengths include a response to the pressure pulse wave through the vessels from the cardiac cycle.

Again, in this example, the biosensor 100 obtained a PPG signal around a wavelength at 940 nm, a wavelength at 880 nm and a wavelength at 660 nm as shown in the PPG Signals for Wavelength Group 4002a. The biosensor 100 also obtained the spectral response for a wavelength at 590 nm, a wavelength at 530 nm and a wavelength at 470 nm as shown in the PPG Signals for Wavelength Group 4002b. The biosensor 100 further obtained the spectral response for a wavelength at 405 nm, a wavelength at 400 nm and a wavelength at 395 nm as shown in the PPG Signals for Wavelength Group 4002c.

During this measurement period, the left hand is still at rest or held relatively level with little to no movement. The user concentrates on mentally activating or initiating an upward movement of the pinky finger on the left hand but with little to no actual movement. The user may mentally envision moving the pinky finger or activating muscles in the pinky finger but with little to no movement. As a result, some neural activity, increased blood flow and vasodilation may occur. The PPG signals include a small fluctuation due to the neural activity and/or vasodilation as seen at the PPG signal patterns 4004a, 4004b and 4004c. The small fluctuation occurs around 239.5 seconds. The PPG signals at each wavelength have a somewhat different or unique pattern in response to the intended or mental movement of the pinky finger. These patterns 4004a-c in the PPG signal are not present in the PPG signals with little to no movement shown in FIG. 38. The unique PPG signal pattern at each wavelength may be used to identify the mental intention to move the pinky finger (but with little to no movement). A user may train the biosensor 100 to detect these mental intentions of movement and so control a device with little to no actual movement.

Figure 41:
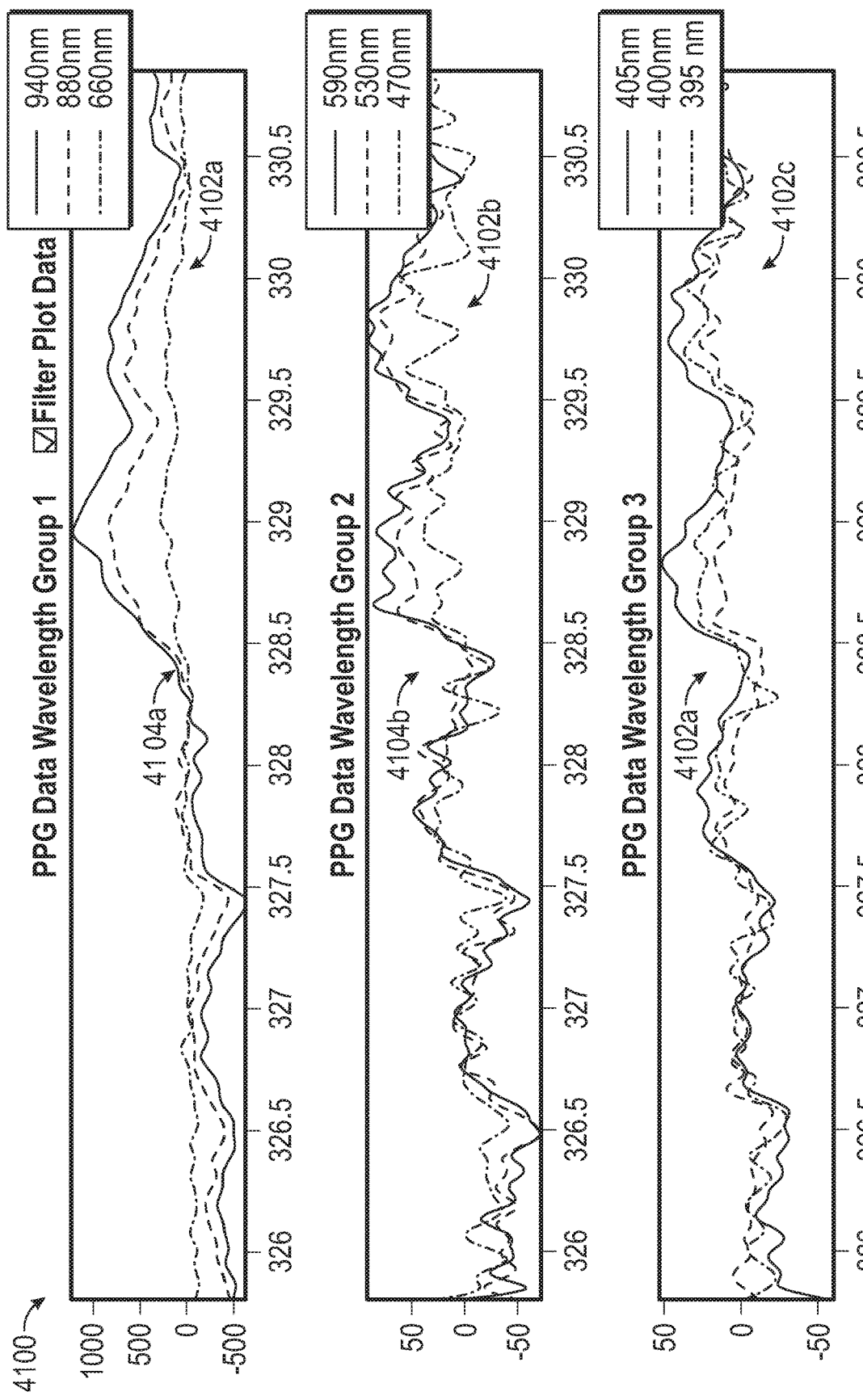
FIG. 41 illustrates a schematic diagram of a graph of spectral responses obtained using an embodiment of the biosensor during a mental intention to move a left thumb upward but with little to no actual movement.

FIG. 41 illustrates a schematic diagram of a graph 4100 of spectral responses obtained using an embodiment of the biosensor 100 during a mental intention to move a left thumb upward but with little to no actual movement. The biosensor 100 is still positioned on the wrist of the left hand of the user and has not been repositioned from FIG. 38. The PPG signals at the plurality of wavelengths include a response to the pressure pulse wave through the vessels from the cardiac cycle.

Again, in this example, the biosensor 100 obtained a PPG signal around a wavelength at 940 nm, a wavelength at 880 nm and a wavelength at 660 nm as shown in the PPG Signals for Wavelength Group 4102a. The biosensor 100 also obtained the spectral response for a wavelength at 590 nm, a wavelength at 530 nm and a wavelength at 470 nm as shown in the PPG Signals for Wavelength Group 4102b. The biosensor 100 further obtained the spectral response for a wavelength at 405 nm, a wavelength at 400 nm and a wavelength at 395 nm as shown in the PPG Signals for Wavelength Group 4102c.

During this measurement period, the left hand is still at rest or held relatively level with little to no movement. The user concentrates on mentally activating or initiating an upward movement of the thumb on the left hand but with little to no actual movement. The user may mentally envision moving the thumb or activating muscles in the thumb but with little to no movement. As a result, some neural activity, increased blood flow and vasodilation may occur. The PPG signals include a small fluctuation due to the neural activity and/or vasodilation as seen at the PPG signal patterns 4104a, 4104b and 4104c. The small fluctuation occurs around 328.5 seconds. The PPG signals at each wavelength have a somewhat different or unique pattern in response to the intended or mental movement of the thumb. These patterns 4104a-c in the PPG signal are not present in the PPG signals with little to no movement shown in FIG. 38. The unique PPG signal pattern at each wavelength may be used to identify the mental intention to move the pinky finger (but with little to no movement). A user may train the biosensor 100 to detect these mental intentions of movement and so control a device with little to no actual movement.

The biosensor 100 may thus obtain PPG signals at a plurality of wavelengths to identify a motion artifact or fluctuation due to a mental or intended movement but with little to no actual movement. The biosensor 100 may then correlate the motion artifact in the PPG signal to a predetermined PPG signal pattern for intended movements. These signal patterns associated with intended movements will be different from the PPG signal patterns associated with actual movements.

The PPG signal patterns for intended movements are associated with motion data and stored in a database. The motion data includes the intended movement, such as the body part and direction of movement (up, down, left, right, retraction or extension or tensing of muscles) or type of movement (fist, rotation, etc.). The motion data may then be used to control operation of a device.

To obtain the PPG signal patterns for intended movement, the biosensor 100 may operate in a training mode. The training mode is initiated, and a request (verbal or nonverbal) is generated to a user to mentally envision movement of a body part and type or direction of movement. The user is instructed to not actually move the body part but only concentrate on mentally initiating or intending to perform the movement. The PPG signals are then obtained while the user concentrates on the intended movement. A motion artifact in the PPG signal is identified and associated with motion data. The motion data includes an identification of the body part and the intended movement of the body part. A user may thus train the biosensor 100 to detect these mental intentions of movement using the PPG signals and so control a device with little to no actual movement.

Figure 42:
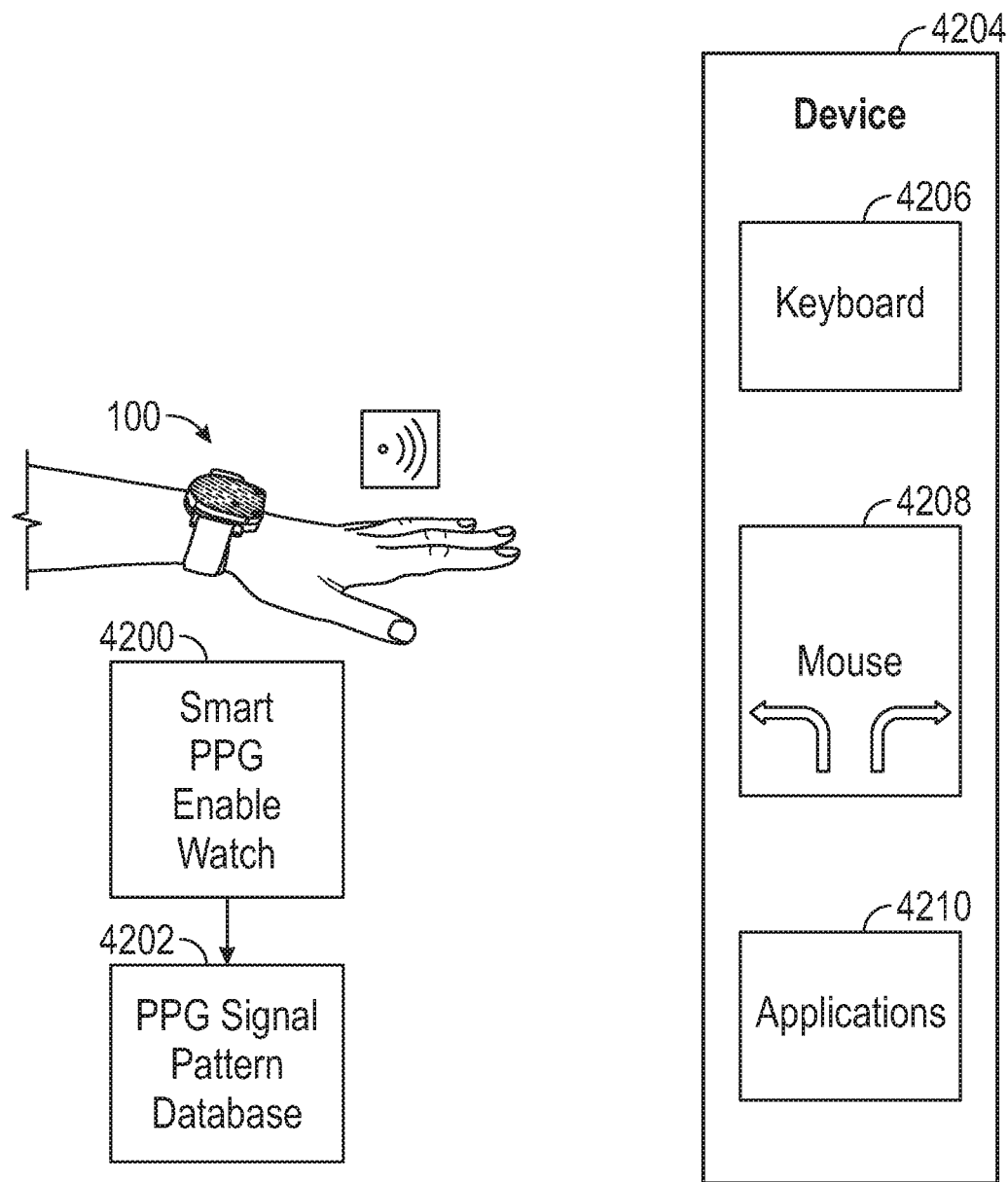
FIG. 42 illustrates a schematic block diagram of an embodiment of the biosensor configured to control a device using PPG signals.

FIG. 42 illustrates a schematic block diagram of an embodiment of the biosensor 100 configured to control a device 4204 using PPG signals. The biosensor 100 may be implemented in a smart PPG enabled watch 4200 or activity monitoring type device such as a Fitbit. The biosensor 100 may include a PPG signal pattern database 4202 or communicate with a central server that provides access to or updates to the PPG signal pattern database 4202. The PPG signal pattern database 4202 includes a plurality of PPG signal patterns at each of a plurality of wavelengths. The plurality of PPG signal patterns is associated with motion data.

The biosensor 100 detects movement using PPG signals. The biosensor 100 obtains motion data and communicates the motion data or control signals to a device 4204. The device 4204 may be a user device, medical device, or any other type of device requiring a man-machine interface. The motion data may be used to control a user interface type device, such as virtual keyboard 4206 for texting or typing. Predictive typing, word suggestion or spell checking may be included with the virtual keyboard 4206. The motion data may also be used to control a virtual mouse 4208, touchpad, touchscreen, joystick, game controller or cursor on a GUI. A wireless USB device may be implemented as the user interface type device, such as the virtual keyboard, touchpad, touchscreen, joystick, etc. The USB device communicates with the biosensor 100 and generates commands to the device 4204 in response to the motion data.

The motion data may also be used to control applications 4210, such as gaming applications, word processing, web browsers, email, etc. For example, moving an index finger left or right against a surface or in the air may move a cursor left or right on a screen. A double tap of an index finger may select a control command or menu item.

FIG. 43 illustrates a schematic block diagram of another embodiment of the biosensor 100 configured to control a device 4300 using PPG signals. In this embodiment, the device may include a television. In an embodiment, the motion data may be associated with predetermined commands. For example, motion data including a fist may be associated with the command "turn off TV". A movement of a thumb down may be associated with the command "Change channel on the TV." The commands associated with the motion may be preprogrammed or programmed by a user. The gesture remote controller 4302 controls the television 4300 based on the motion data and the associated command. The device 4300 may also include a vehicle and motion data may be used to control navigation, climate, entertainment systems, or other operations of the vehicle.

In an embodiment, the biosensor 100 may obtain a stress level using the PPG signals. The tension and duration of tension in muscles may be measured over an extended time period using the PPG signals. The biosensor 100 may then obtain a stress level using the information.

In one or more aspects herein, a processing module or circuit includes at least one processing device, such as a microprocessor, micro-controller, digital signal processor, microcomputer, central processing unit, field programmable gate array, programmable logic device, state machine, logic circuitry, analog circuitry, digital circuitry, and/or any device that manipulates signals (analog and/or digital) based on hard coding of the circuitry and/or operational instructions. A memory is a non-transitory memory device and may be an internal memory or an external memory, and the memory may be a single memory device or a plurality of memory devices. The memory may be a read-only memory, random access memory, volatile memory, non-volatile memory, static memory, dynamic memory, flash memory, cache memory, and/or any non-transitory memory device that stores digital information.

As may be used herein, the term "operable to" or "configurable to" indicates that an element includes one or more of circuits, instructions, modules, data, input(s), output(s), etc., to perform one or more of the described or necessary corresponding functions and may further include inferred coupling to one or more other items to perform the described or necessary corresponding functions. As may also be used herein, the term(s) "coupled", "coupled to", "connected to" and/or "connecting" or "interconnecting" includes direct connection or link between nodes/devices and/or indirect connection between nodes/devices via an intervening item (e.g., an item includes, but is not limited to, a component, an element, a circuit, a module, a node, device, network element, etc.). As may further be used herein, inferred connections (i.e., where one element is connected to another element by inference) includes direct and indirect connection between two items in the same manner as "connected to".

As may be used herein, the terms "substantially" and "approximately" provides an industry-accepted tolerance for its corresponding term and/or relativity between items. Such an industry-accepted tolerance ranges from less than one percent to fifty percent and corresponds to, but is not limited to, frequencies, wavelengths, component values, integrated circuit process variations, temperature variations, rise and fall times, and/or thermal noise. Such relativity between items ranges from a difference of a few percent to magnitude differences.

Note that the aspects of the present disclosure may be described herein as a process that is depicted as a schematic, a flowchart, a flow diagram, a structure diagram, or a block diagram. Although a flowchart may describe the operations as a sequential process, many of the operations can be performed in parallel or concurrently. In addition, the order of the operations may be re-arranged. A process is terminated when its operations are completed. A process may correspond to a method, a function, a procedure, a subroutine, a subprogram, etc. When a process corresponds to a function, its termination corresponds to a return of the function to the calling function or the main function.

The various features of the disclosure described herein can be implemented in different systems and devices without departing from the disclosure. It should be noted that the foregoing aspects of the disclosure are merely examples and are not to be construed as limiting the disclosure. The description of the aspects of the present disclosure is intended to be illustrative, and not to limit the scope of the claims. As such, the present teachings can be readily applied to other types of apparatuses and many alternatives, modifications, and variations will be apparent to those skilled in the art.

In the foregoing specification, certain representative aspects of the invention have been described with reference to specific examples. Various modifications and changes may be made, however, without departing from the scope of the present invention as set forth in the claims. The specification and figures are illustrative, rather than restrictive, and modifications are intended to be included within the scope of the present invention. Accordingly, the scope of the invention should be determined by the claims and their legal equivalents rather than by merely the examples described. For example, the components and/or elements recited in any apparatus claims may be assembled or otherwise operationally configured in a variety of permutations and are accordingly not limited to the specific configuration recited in the claims.

Furthermore, certain benefits, other advantages and solutions to problems have been described above with regard to particular embodiments; however, any benefit, advantage, solution to a problem, or any element that may cause any particular benefit, advantage, or solution to occur or to become more pronounced are not to be construed as critical, required, or essential features or components of any or all the claims.

As used herein, the terms "comprise," "comprises," "comprising," "having," "including," "includes" or any variation thereof, are intended to reference a nonexclusive inclusion, such that a process, method, article, composition or apparatus that comprises a list of elements does not include only those elements recited, but may also include other elements not expressly listed or inherent to such process, method, article, composition, or apparatus. Other combinations and/or modifications of the above-described structures, arrangements, applications, proportions, elements, materials, or components used in the practice of the present invention, in addition to those not specifically recited, may be varied or otherwise particularly adapted to specific environments, manufacturing specifications, design parameters, or other operating requirements without departing from the general principles of the same.

Moreover, reference to an element in the singular is not intended to mean "one and only one" unless specifically so stated, but rather "one or more." Unless specifically stated otherwise, the term "some" refers to one or more. All structural and functional equivalents to the elements of the various aspects described throughout this disclosure that are known or later come to be known to those of ordinary skill in the art are expressly incorporated herein by reference and are intended to be encompassed by the claims. Moreover, nothing disclosed herein is intended to be dedicated to the public regardless of whether such disclosure is explicitly recited in the claims. No claim element is intended to be construed under the provisions of 35 U.S.C. § 112(f) as a "means-plus-function" type element, unless the element is expressly recited using the phrase "means for" or, in the case of a method claim, the element is recited using the phrase "step for."

The invention claimed is:

1. A biosensor, comprising:
    a memory configured to store a database including a plurality of predetermined patterns and associated control commands for a device;
    a sensor configured for positioning over an area of tissue of a user and configured to obtain an optical signal, wherein the optical signal includes a spectral response around a first wavelength of light reflected from the area of the tissue of the user;
    a processing device configured to:
        process the optical signal at the first wavelength to identify a first motion artifact at a first time interval;
        correlate the first motion artifact to a first predetermined pattern of the plurality of predetermined patterns in the database and determine a first control command for the device associated with the first predetermined pattern using the database;
        process the optical signal at the first wavelength to identify a second motion artifact at a second time interval; and
        correlate the second motion artifact to a second predetermined pattern of the plurality of predetermined patterns in the database and determine a second control command for the device associated with the second predetermined pattern using the database.

2. The biosensor of claim 1, wherein the first and second control commands are input to the device, wherein the device includes a user device or vehicle.

3. The biosensor of claim 2, wherein the associated control commands include at least one of: selection of a key on a virtual keyboard, selection of an icon on a GUI, control movement of a cursor on a display of the user device, or control movement of the vehicle.

4. The biosensor of claim 1, wherein the first motion artifact reflects changes in blood flow through vessels in the area of the tissue due to movement of a first body part at the first time interval and wherein the second motion artifact reflects changes in blood flow through vessels in the area of the tissue due to the movement of a second body part at the second time interval.

5. The biosensor of claim 4, wherein the database further includes motion data of a body part associated with each of the plurality of predetermined patterns.

6. The biosensor of claim 5, wherein the processing device is further configured to:
    obtain first motion data for the first body part associated with the first predetermined pattern; and
    obtain second motion data for the second body part associated with the second predetermined pattern.

7. The biosensor of claim 6, wherein the first motion data includes an identification of the first body part, a direction of movement of the first body part and a speed of the movement of the first body part; and wherein the second motion data includes an identification of the second body part, a direction of movement of the second body part and a speed of the movement of the second body part.

8. The biosensor of claim 7, wherein the processing device is configured to:
    obtain a direct current (DC) level or a maximum amplitude of the first motion artifact; and
    determine a force of movement of the first body part using the DC level or the maximum amplitude of the first motion artifact.

9. The biosensor of claim 1, wherein the sensor is included in a band configured for positioning over the area of the tissue of a wrist or arm of the user and comprises:
    a photodetector configured to detect light from the area of the tissue of the wrist or arm of the user; and
    at least one light source configured to emit light at the first wavelength.

10. The biosensor of claim 1, wherein the processing device is configured to:
    obtain a heart rate signal using the optical signal;
    determine a quality factor of the optical signal; and
    process the optical signal when the quality factor exceeds a predetermined threshold.

11. The biosensor of claim 1, wherein the processing device is a neural network processing device.

12. A wearable device, comprising:
    a sensor configured for positioning over an area of tissue of a user and configured to obtain an optical signal, wherein the optical signal includes a spectral response around a first wavelength of light reflected from the area of the tissue of the user;
    a processing circuit in communication with the sensor and configured to:
        determine a heart rate signal from the optical signal;
        determine a quality factor of the heart rate signal;
        when the quality factor exceeds a predetermined threshold, identify a first motion artifact at a first time interval in the optical signal and a second motion artifact at a second time interval in the optical signal;
        compare the first and second motion artifacts to a plurality of predetermined patterns in a database, wherein each of the plurality of predetermined patterns is associated with a control command;
        correlate the first motion artifact to a first predetermined pattern of the plurality of predetermined patterns in the database and determine a first control command associated with the first predetermined pattern using the database;
        correlate the second motion artifact to a second predetermined pattern of the plurality of predetermined patterns in the database and determine a second control command associated with the second predetermined pattern using the database; and
    a transmitter configured to transmit the first and second control commands to a user device for controlling the user device.

13. The wearable device of claim 12, wherein the processing circuit is further configured to:
    control the wearable device in response to the first and second control commands.

14. The wearable device of claim 12, wherein the processing circuit is further configured to:
    initiate a training mode for customization of the first predetermined pattern in a database;
    request movement of a first body part of the user;

obtain an optical signal of the user during the requested movement of the first body part;

identify a motion artifact in the optical signal due to the requested movement of the body part; and update the first predetermined pattern in the database using the motion artifact in the optical signal.

15. The wearable device of claim 12, wherein the first motion artifact reflects changes in blood flow through vessels in the area of the tissue due to movement of a first body part at the first time interval and wherein the second motion artifact reflects changes in blood flow through vessels in the area of the tissue due to the movement of a second body part at the second time interval.

16. The wearable device of claim 12, wherein the processing circuit is further configured to:

when the quality factor of the heart rate signal is not within the predetermined threshold, generate a request to reposition the wearable device.

17. The wearable device of claim 12, wherein each of the plurality of predetermined patterns in the database is further associated with motion data of a body part, wherein the motion data includes an identification of the body part, a direction of movement of the body part and a speed of the movement of the body part.

18. A biosensor, comprising:

a sensor configured to obtain an optical signal, wherein the optical signal includes a spectral response around a wavelength of light detected from tissue of a user;

a processing device configured to:

identify a fluctuation in the optical signal, wherein the fluctuation in the optical signal reflects neural activity or vasodilation of vessels in the tissue of the user;

correlate the fluctuation in the optical signal to a predetermined signal pattern, wherein the predetermined signal pattern is associated with an intended movement of a body part due to a mental initiating of movement with little to no actual movement of the body part;

determine a control command associated with the intended movement of the body part; and control operation of a device in response to the control command.

19. The biosensor of claim 18, wherein the processing circuit is configured to obtain the predetermined signal pattern by:

initiating a training mode for the biosensor;

generating by the device a request to the user to mentally intend to move the body part without actual movement of the second body part;

obtaining a training optical signal around the wavelength of light in response to the request;

identifying a fluctuation in the training optical signal; and update the predetermined signal pattern using the fluctuation.

* * * * *